US007923014B2

(12) United States Patent
Hooper et al.

(10) Patent No.: US 7,923,014 B2
(45) Date of Patent: Apr. 12, 2011

(54) EXPRESSION AND PURIFICATION OF HIP/PAP AND USES THEREFOR

(75) Inventors: Lora V. Hooper, Dallas, TX (US); Heather L. Cash, Owens Cross Roads, AL (US); Cecilia V. Whitham, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 459 days.

(21) Appl. No.: 12/026,010

(22) Filed: Feb. 5, 2008

(65) Prior Publication Data

US 2010/0172922 A1 Jul. 8, 2010

Related U.S. Application Data

(60) Provisional application No. 60/889,424, filed on Feb. 12, 2007, provisional application No. 60/970,462, filed on Sep. 6, 2007.

(51) Int. Cl.
*A61K 39/00* (2006.01)

(52) U.S. Cl. .................................. 424/185.1; 424/192.1

(58) Field of Classification Search ........................ None
See application file for complete search history.

(56) References Cited

U.S. PATENT DOCUMENTS

| | | | | |
|---|---|---|---|---|
| 5,110,795 | A | 5/1992 | Hahn | 514/17 |
| 5,112,856 | A | 5/1992 | Gaginella et al. | 514/456 |
| 5,216,002 | A | 6/1993 | Gidda et al. | 514/369 |
| 5,238,931 | A | 8/1993 | Yoshikawa et al. | 514/184 |
| 5,292,771 | A | 3/1994 | Backstrom et al. | 514/472 |
| 5,312,818 | A | 5/1994 | Rubin et al. | 514/161 |
| 5,324,738 | A | 6/1994 | Dinan et al. | 514/325 |
| 5,331,013 | A | 7/1994 | Ahlman et al. | 514/626 |
| 5,340,801 | A | 8/1994 | Ewing et al. | 514/18 |
| 5,368,854 | A | 11/1994 | Rennick | 424/85.2 |
| 5,391,555 | A | 2/1995 | Marshall et al. | 514/311 |
| 5,552,439 | A | 9/1996 | Panetta | 514/534 |
| 5,569,680 | A | 10/1996 | Wu | 514/786 |
| 5,599,795 | A | 2/1997 | McCann et al. | 424/93.4 |
| 5,604,231 | A | 2/1997 | Smith et al. | 514/256 |
| 5,691,343 | A | 11/1997 | Sandborn | 514/263.3 |
| 5,693,645 | A | 12/1997 | Sharpe et al. | 514/278 |
| 2005/0277593 | A1* | 12/2005 | Dieckgraefe et al. | 514/12 |

OTHER PUBLICATIONS

Abergel et al., "Crystallization and preliminary crystallographic study of HIP/PAP, a human C-lectin overexpressed in primary liver cancers," *D. Biol. Crystallogr.*, 55(Pt 8):1487-1489, 1999.

Ayabe et al., "Secretion of microbicidal alpha-defensins by intestinal Paneth cells in response to bacteria," *Nat. Immunol.*, 1:113-8, 2000.

Bertrand et al., "Crystal structure of human lithostathine, the pancreatic inhibitor of stone formation," *Embo J.*, 15:2678-2684, 1996.

Cash et al., "Refolding, purification, and characterization of human and murine RegIII proteins expressed in *Escherichia coli," Protein Expr. Purif.*, 48:151-159, 2006.

Christa et al., "HIP/PAP is an adhesive protein expressed in hepatocarcinoma, normal Paneth, and pancreatic cells," *Am. J. Physiol.*, 271:G993-1002, 1996.

Christa et al., "High expression of the human hepatocarcinoma-intestine-pancreas/pancreatic-associated protein (HIP/PAP) gene in the mammary gland of lactating transgenic mice. Secretion into the milk and purification of the HIP/PAP lectin," *Eur. J. Biochem.*, 267:1665-1671, 2000.

Christa et al., "The human HIP gene, overexpressed in primary liver cancer encodes for a C-type carbohydrate binding protein with lactose binding activity," *FEBS Lett.*, 337:114-118, 1994.

Dieckgraefe et al., "Expression of the regenerating gene family in inflammatory bowel disease mucosa: Reg Ialpha upregulation, processing, and antiapoptotic activity," *J. Investig. Med.*, 50:421-434, 2002.

Ezekowitz, "Role of the mannose-binding lectin in innate immunity," *J. Infect. Dis.*, 187:S335-339, 2003.

Girardin et al., "Nod1 detects a unique muropeptide from gram-negative bacterial peptidoglycan," *Science*, 300:1584-7, 2003.

Hooper et al., "How host-microbial interactions shape the nutrient environment of the mammalian intestine," *Annu. Rev. Nutr.*, 22:283-307, 2002.

Inohara et al., "Host recognition of bacterial muramyl dipeptide mediated through NOD2. Implications for Crohn's disease," *J. Biol. Chem.*, 278:5509-12, 2003.

Keilbaugh et al., "Activation of RegIIIbeta/gamma and interferon gamma expression in the intestinal tract of SCID mice: an innate response to bacterial colonisation of the gut," *Gut.*, 54:623-629, 2005.

Livesey et al., "A Schwann cell mitogen accompanying regeneration of motor neurons," *Nature*, 390:614-8, 1997.

Macpherson et al., "A primitive T cell-independent mechanism of intestinal mucosal IgA responses to commensal bacteria," *Science*, 288:2222-6, 2000.

Narushima et al., "Structure, chromosomal localization and expression of mouse genes encoding type III Reg, RegIII alpha, RegIII beta, RegIII gamma," *Gene*, 185:159-168, 1997.

Ogawa et al., "Increased expression of HIP/PAP and regenerating gene III in human inflammatory bowel disease and a murine bacterial reconstitution model," *Inflamm. Bowel Dis.*, 9:162-170, 2003.

Ogawa et al., "Identification of genes involved in mucosal defense and inflammation associated with normal enteric bacteria," *Am. J. Physiol. Gastrointest. Liver Physiol.*, 279:G492-499, 2000.

Pull et al., "Activated macrophages are an adaptive element of the colonic epithelial progenitor niche necessary for regenerative responses to injury," *Proc. Natl. Acad. Sci. USA*, 102:99-104, 2005.

Swidsinski et al., "Mucosal flora in inflammatory bowel disease," *Gastroenterology*, 122:44-54, 2002.

Syder et al., "The impact of parietal cells on *Helicobacter pylori* tropism and host pathology: an analysis using gnotobiotic normal and transgenic mice," *Proc. Natl. Acad. Sci. USA*, 100:3467-72, 2003.

Terazono et al., "A novel gene activated in regenerating islets," *J. Biol. Chem.*, 263:2111-2114, 1988.

Weis et al., "Structure of a C-type mannose-binding protein complexed with an oligosaccharide," *Nature*, 360:127-134, 1992.

* cited by examiner

*Primary Examiner* — Mark Navarro
(74) *Attorney, Agent, or Firm* — Fulbright & Jaworski

(57) ABSTRACT

The present invention relates to methods of compositions comprising RegIII and HIP/PAP proteins, including the use of such proteins as diagnostic and therapeutic targets.

2 Claims, 22 Drawing Sheets

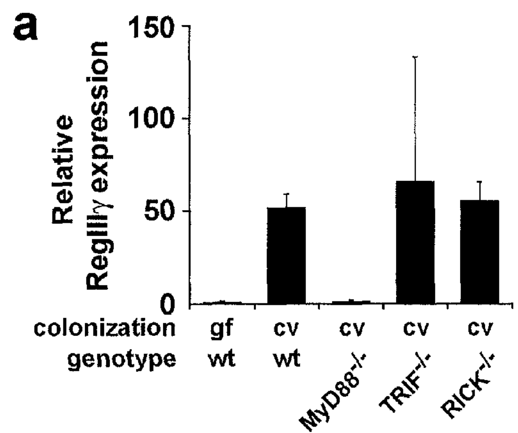
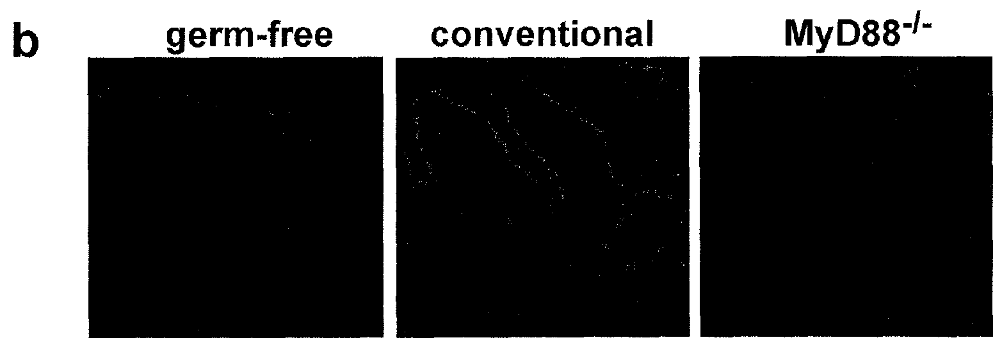
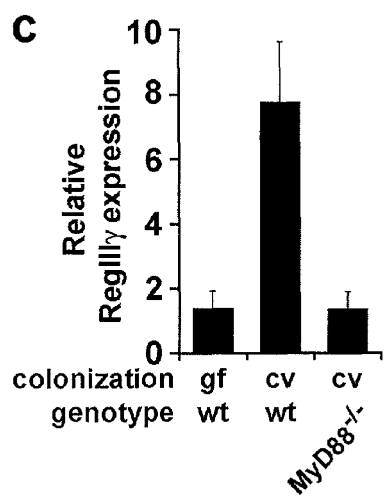
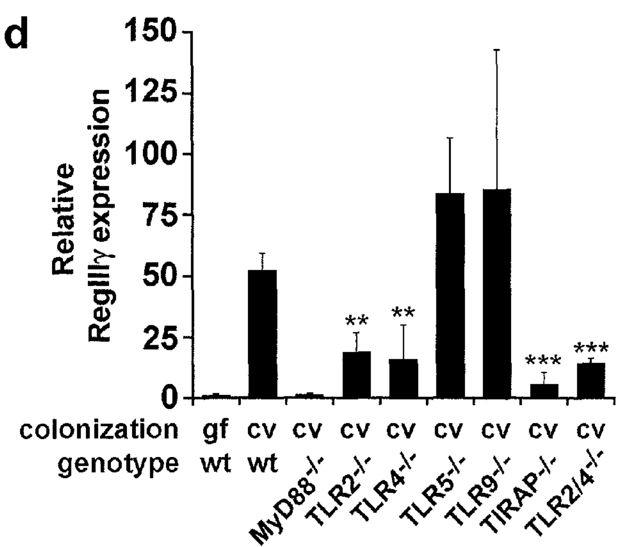
FIG. 18A-D

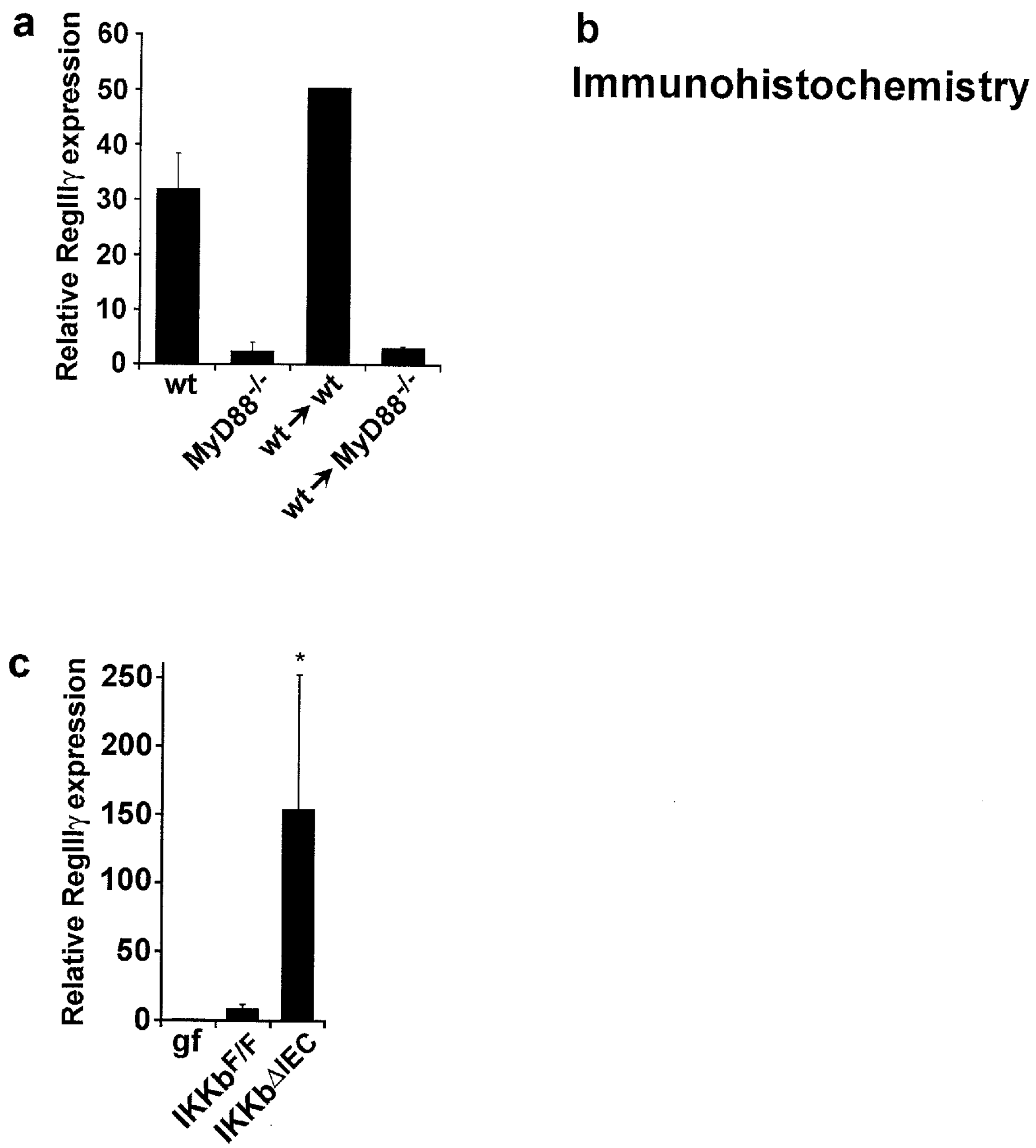
FIG. 19A-C

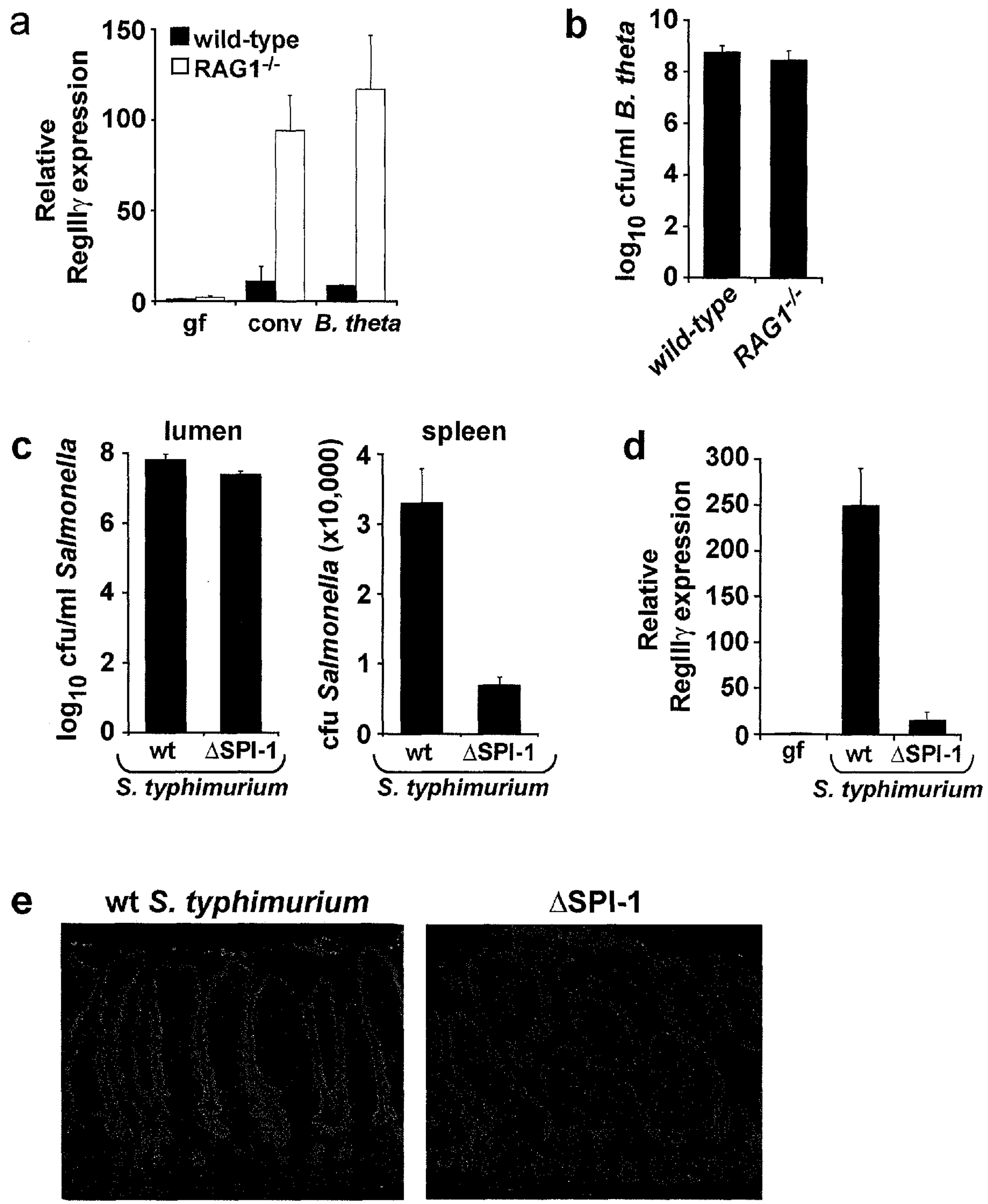
FIG. 20A-E

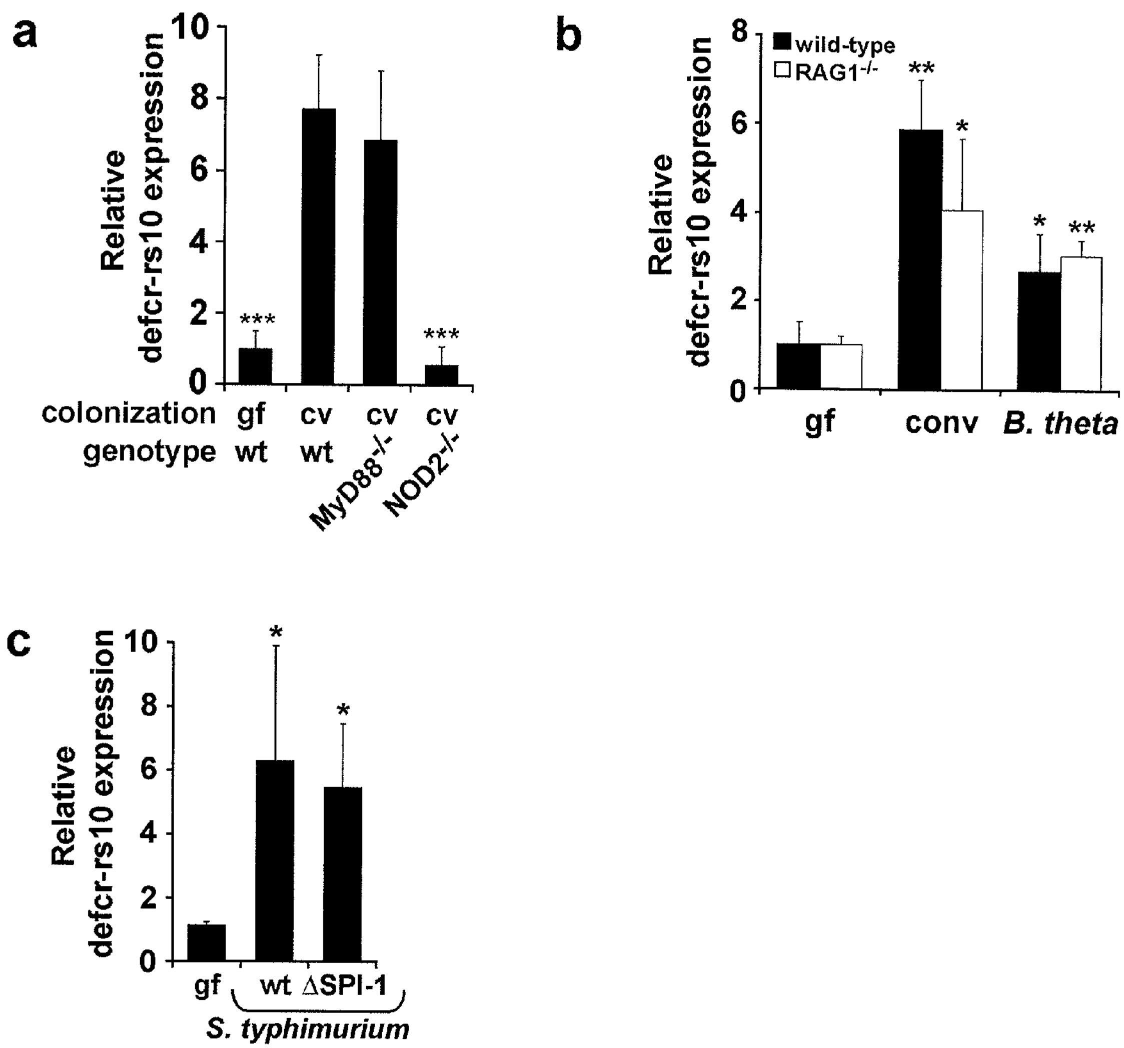
FIG. 21A-C

SEQUENCE LISTING

<160> NUMBER OF SEQ ID NOS: 56

<210> SEQ ID NO 1
<211> LENGTH: 174
<212> TYPE: PRT
<213> ORGANISM: Mus musculus

<400> SEQUENCE: 1

Met Leu Pro Arg Ile Thr Ile Thr Ile Met Ser Trp Met Leu Leu Ser
1               5                   10                  15

Cys Leu Met Leu Leu Ser Gln Val Gln Gly Glu Val Ala Lys Lys Asp
            20                  25                  30

Ala Pro Ser Ser Arg Ser Ser Cys Pro Lys Gly Ser Arg Ala Tyr Gly
        35                  40                  45

Ser Tyr Cys Tyr Ala Leu Phe Ser Val Ser Lys Asn Trp Tyr Asp Ala
    50                  55                  60

Asp Met Ala Cys Gln Lys Arg Pro Ser Gly His Leu Val Ser Val Leu
65                  70                  75                  80

Ser Gly Ala Glu Ala Ser Phe Leu Ser Ser Met Ile Lys Ser Ser Gly
                85                  90                  95

Asn Ser Gly Gln Tyr Val Trp Ile Gly Leu His Asp Pro Thr Leu Gly
            100                 105                 110

```
Tyr Glu Pro Asn Arg Gly Gly Trp Glu Trp Ser Asn Ala Asp Val Met
        115                 120                 125

Asn Tyr Ile Asn Trp Glu Thr Asn Pro Ser Ser Ser Ser Gly Asn His
    130                 135                 140

Cys Gly Thr Leu Ser Arg Ala Ser Gly Phe Leu Lys Trp Arg Glu Asn
145                 150                 155                 160

Tyr Cys Asn Leu Glu Leu Pro Tyr Val Cys Lys Phe Lys Ala
                165                 170


<210> SEQ ID NO 2
<211> LENGTH: 174
<212> TYPE: PRT
<213> ORGANISM: Mus musculus

<400> SEQUENCE: 2

Met Leu Pro Arg Ile Thr Ile Thr Ile Met Ser Trp Met Leu Leu Ser
1               5                   10                  15

Cys Leu Met Leu Leu Ser Gln Val Gln Gly Glu Val Ala Lys Lys Asp
            20                  25                  30

Ala Pro Ser Ser Arg Ser Ser Cys Pro Lys Gly Ser Arg Ala Tyr Gly
        35                  40                  45

Ser Tyr Cys Tyr Ala Leu Phe Ser Val Ser Lys Asn Trp Tyr Asp Ala
    50                  55                  60

Asp Met Ala Cys Gln Lys Arg Pro Ser Gly His Leu Val Ser Val Leu
65                  70                  75                  80

Ser Gly Ala Glu Ala Ser Phe Leu Ser Ser Met Ile Lys Ser Ser Gly
                85                  90                  95

Asn Ser Gly Gln Tyr Val Trp Ile Gly Leu His Asp Pro Thr Leu Gly
            100                 105                 110

Tyr Glu Pro Asn Arg Gly Gly Trp Glu Trp Ser Asn Ala Asp Val Met
        115                 120                 125

Asn Tyr Ile Asn Trp Glu Thr Asn Pro Ser Ser Ser Ser Gly Asn His
    130                 135                 140

Cys Gly Thr Leu Ser Arg Ala Ser Gly Phe Leu Lys Trp Arg Glu Asn
145                 150                 155                 160

Tyr Cys Asn Leu Glu Leu Pro Tyr Val Cys Lys Phe Lys Ala
                165                 170


<210> SEQ ID NO 3
<211> LENGTH: 174
<212> TYPE: PRT
<213> ORGANISM: Mus musculus

<400> SEQUENCE: 3

Met Leu Pro Arg Ile Thr Ile Thr Ile Met Ser Trp Met Leu Leu Ser
1               5                   10                  15

Cys Leu Met Leu Leu Ser Gln Val Gln Gly Glu Val Ala Lys Lys Asp
            20                  25                  30

Ala Pro Ser Ser Arg Ser Ser Cys Pro Lys Gly Ser Arg Ala Tyr Gly
        35                  40                  45

Ser Tyr Cys Tyr Ala Leu Phe Ser Val Ser Lys Asn Trp Tyr Asp Ala
    50                  55                  60

Asp Met Ala Cys Gln Lys Arg Pro Ser Gly His Leu Val Ser Val Leu
65                  70                  75                  80

Ser Gly Ala Glu Ala Ser Phe Leu Ser Ser Met Ile Lys Ser Ser Gly
                85                  90                  95
```

```
Asn Ser Gly Gln Tyr Val Trp Ile Gly Leu His Asp Pro Thr Leu Gly
            100                 105                 110

Tyr Glu Pro Asn Arg Gly Gly Trp Glu Trp Ser Asn Ala Asp Val Met
        115                 120                 125

Asn Tyr Ile Asn Trp Glu Thr Asn Pro Ser Ser Ser Ser Gly Asn His
    130                 135                 140

Cys Gly Thr Leu Ser Arg Ala Ser Gly Phe Leu Lys Trp Arg Glu Asn
145                 150                 155                 160

Tyr Cys Asn Leu Glu Leu Pro Tyr Val Cys Lys Phe Lys Ala
                165                 170


<210> SEQ ID NO 4
<211> LENGTH: 174
<212> TYPE: PRT
<213> ORGANISM: Mus musculus

<400> SEQUENCE: 4

Met Leu Pro Arg Ile Thr Ile Thr Ile Met Ser Trp Met Leu Leu Ser
1               5                   10                  15

Cys Leu Met Leu Leu Ser Gln Val Gln Gly Glu Val Ala Lys Lys Asp
            20                  25                  30

Ala Pro Ser Ser Arg Ser Ser Cys Pro Lys Gly Ser Arg Ala Tyr Gly
        35                  40                  45

Ser Tyr Cys Tyr Ala Leu Phe Ser Val Ser Lys Asn Trp Tyr Asp Ala
    50                  55                  60

Asp Met Ala Cys Gln Lys Arg Pro Ser Gly His Leu Val Ser Val Leu
65                  70                  75                  80

Ser Gly Ala Glu Ala Ser Phe Leu Ser Ser Met Ile Lys Ser Ser Gly
                85                  90                  95

Asn Ser Gly Gln Tyr Val Trp Ile Gly Leu His Asp Pro Thr Leu Gly
            100                 105                 110

Tyr Glu Pro Asn Arg Gly Gly Trp Glu Trp Ser Asn Ala Asp Val Met
        115                 120                 125

Asn Tyr Ile Asn Trp Glu Thr Asn Pro Ser Ser Ser Ser Gly Asn His
    130                 135                 140

Cys Gly Thr Leu Ser Arg Ala Ser Gly Phe Leu Lys Trp Arg Glu Asn
145                 150                 155                 160

Tyr Cys Asn Leu Glu Leu Pro Tyr Val Cys Lys Phe Lys Ala
                165                 170


<210> SEQ ID NO 5
<211> LENGTH: 174
<212> TYPE: PRT
<213> ORGANISM: Mus musculus

<400> SEQUENCE: 5

Met Leu Pro Arg Ile Thr Ile Thr Ile Met Ser Trp Met Leu Leu Ser
1               5                   10                  15

Cys Leu Met Leu Leu Ser Gln Val Gln Gly Glu Val Ala Lys Lys Asp
            20                  25                  30

Ala Pro Ser Ser Arg Ser Ser Cys Pro Lys Gly Ser Arg Ala Tyr Gly
        35                  40                  45

Ser Tyr Cys Tyr Ala Leu Phe Ser Val Ser Lys Asn Trp Tyr Asp Ala
    50                  55                  60

Asp Met Ala Cys Gln Lys Arg Pro Ser Gly His Leu Val Ser Val Leu
65                  70                  75                  80

Ser Gly Ala Glu Ala Ser Phe Leu Ser Ser Met Ile Lys Ser Ser Gly
```

```
                85                  90                  95

Asn Ser Gly Gln Tyr Val Trp Ile Gly Leu His Asp Pro Thr Leu Gly
            100                 105                 110

Tyr Glu Pro Asn Arg Gly Gly Trp Glu Trp Ser Asn Ala Asp Val Met
        115                 120                 125

Asn Tyr Ile Asn Trp Glu Thr Asn Pro Ser Ser Ser Ser Gly Asn His
    130                 135                 140

Cys Gly Thr Leu Ser Arg Ala Ser Gly Phe Leu Lys Trp Arg Glu Asn
145                 150                 155                 160

Tyr Cys Asn Leu Glu Leu Pro Tyr Val Cys Lys Phe Lys Ala
                165                 170


<210> SEQ ID NO 6
<211> LENGTH: 175
<212> TYPE: PRT
<213> ORGANISM: Mus musculus

<400> SEQUENCE: 6

Met Leu Pro Pro Thr Ala Cys Ser Val Met Ser Trp Met Leu Leu Ser
1               5                   10                  15

Cys Leu Met Leu Leu Ser Gln Val Gln Gly Glu Asp Ser Leu Lys Asn
            20                  25                  30

Ile Pro Ser Ala Arg Ile Ser Cys Pro Lys Gly Ser Gln Ala Tyr Gly
        35                  40                  45

Ser Tyr Cys Tyr Ala Leu Phe Gln Ile Pro Gln Thr Trp Phe Asp Ala
    50                  55                  60

Glu Leu Ala Cys Gln Lys Arg Pro Gly Gly His Leu Val Ser Val Leu
65                  70                  75                  80

Asn Ser Ala Glu Ala Ser Phe Leu Ser Ser Met Val Lys Arg Thr Gly
                85                  90                  95

Asn Ser Tyr Gln Tyr Thr Trp Ile Gly Leu His Asp Pro Thr Leu Gly
            100                 105                 110

Ala Glu Pro Asn Gly Gly Gly Trp Glu Trp Ser Asn Asn Asp Val Met
        115                 120                 125

Asn Tyr Phe Asn Trp Glu Arg Asn Pro Ser Thr Ala Leu Asp Arg Ala
    130                 135                 140

Phe Cys Gly Ser Leu Ser Arg Ala Ser Gly Phe Leu Lys Trp Arg Asp
145                 150                 155                 160

Met Thr Cys Glu Val Lys Leu Pro Tyr Val Cys Lys Phe Thr Gly
                165                 170                 175


<210> SEQ ID NO 7
<211> LENGTH: 175
<212> TYPE: PRT
<213> ORGANISM: Mus musculus

<400> SEQUENCE: 7

Met Leu Pro Pro Thr Ala Cys Ser Val Met Ser Trp Met Leu Leu Ser
1               5                   10                  15

Cys Leu Met Leu Leu Ser Gln Val Gln Gly Glu Asp Ser Leu Lys Asn
            20                  25                  30

Ile Pro Ser Ala Arg Ile Ser Cys Pro Lys Gly Ser Gln Ala Tyr Gly
        35                  40                  45

Ser Tyr Cys Tyr Ala Leu Phe Gln Ile Pro Gln Thr Trp Phe Asp Ala
    50                  55                  60

Glu Leu Ala Cys Gln Lys Arg Pro Gly Gly His Leu Val Ser Val Leu
65                  70                  75                  80
```

```
Asn Ser Ala Glu Ala Ser Phe Leu Ser Ser Met Val Lys Arg Thr Gly
                85                  90                  95

Asn Ser Tyr Gln Tyr Thr Trp Ile Gly Leu His Asp Pro Thr Leu Gly
            100                 105                 110

Ala Glu Pro Asn Gly Gly Gly Trp Glu Trp Ser Asn Asn Asp Val Met
        115                 120                 125

Asn Tyr Phe Asn Trp Glu Arg Asn Pro Ser Thr Ala Leu Asp Arg Ala
    130                 135                 140

Phe Cys Gly Ser Leu Ser Arg Ala Ser Gly Phe Leu Lys Trp Arg Asp
145                 150                 155                 160

Met Thr Cys Glu Val Lys Leu Pro Tyr Val Cys Lys Phe Thr Gly
                165                 170                 175


<210> SEQ ID NO 8
<211> LENGTH: 175
<212> TYPE: PRT
<213> ORGANISM: Mus musculus

<400> SEQUENCE: 8

Met Leu Pro Pro Thr Ala Cys Ser Val Met Ser Trp Met Leu Leu Ser
1               5                   10                  15

Cys Leu Met Leu Leu Ser Gln Val Gln Gly Glu Asp Ser Leu Lys Asn
            20                  25                  30

Ile Pro Ser Ala Arg Ile Ser Cys Pro Lys Gly Ser Gln Ala Tyr Gly
        35                  40                  45

Ser Tyr Cys Tyr Ala Leu Phe Gln Ile Pro Gln Thr Trp Phe Asp Ala
    50                  55                  60

Glu Leu Ala Cys Gln Lys Arg Pro Gly Gly His Leu Val Ser Val Leu
65                  70                  75                  80

Asn Ser Ala Glu Ala Ser Phe Leu Ser Ser Met Val Lys Arg Thr Gly
                85                  90                  95

Asn Ser Tyr Gln Tyr Thr Trp Ile Gly Leu His Asp Pro Thr Leu Gly
            100                 105                 110

Ala Glu Pro Asn Gly Gly Gly Trp Glu Trp Ser Asn Asn Asp Val Met
        115                 120                 125

Asn Tyr Phe Asn Trp Glu Arg Asn Pro Ser Thr Ala Leu Asp Arg Ala
    130                 135                 140

Phe Cys Gly Ser Leu Ser Arg Ala Ser Gly Phe Leu Lys Trp Arg Asp
145                 150                 155                 160

Met Thr Cys Glu Val Lys Leu Pro Tyr Val Cys Lys Phe Thr Gly
                165                 170                 175


<210> SEQ ID NO 9
<211> LENGTH: 175
<212> TYPE: PRT
<213> ORGANISM: Mus musculus

<400> SEQUENCE: 9

Met Leu Pro Pro Thr Ala Cys Ser Val Met Ser Trp Met Leu Leu Ser
1               5                   10                  15

Cys Leu Met Leu Leu Ser Gln Val Gln Gly Glu Asp Ser Leu Lys Asn
            20                  25                  30

Ile Pro Ser Ala Arg Ile Ser Cys Pro Lys Gly Ser Gln Ala Tyr Gly
        35                  40                  45

Ser Tyr Cys Tyr Ala Leu Phe Gln Ile Pro Gln Thr Trp Phe Asp Ala
    50                  55                  60
```

```
Glu Leu Ala Cys Gln Lys Arg Pro Gly Gly His Leu Val Ser Val Leu
65                  70                  75                  80

Asn Ser Ala Glu Ala Ser Phe Leu Ser Ser Met Val Lys Arg Thr Gly
                85                  90                  95

Asn Ser Tyr Gln Tyr Thr Trp Ile Gly Leu His Asp Pro Thr Leu Gly
            100                 105                 110

Ala Glu Pro Asn Gly Gly Gly Trp Glu Trp Ser Asn Asn Asp Val Met
        115                 120                 125

Asn Tyr Phe Asn Trp Glu Arg Asn Pro Ser Thr Ala Leu Asp Arg Ala
    130                 135                 140

Phe Cys Gly Ser Leu Ser Arg Ala Ser Gly Phe Leu Lys Trp Arg Asp
145                 150                 155                 160

Met Thr Cys Glu Val Lys Leu Pro Tyr Val Cys Lys Phe Thr Gly
                165                 170                 175


<210> SEQ ID NO 10
<211> LENGTH: 174
<212> TYPE: PRT
<213> ORGANISM: Homo sapiens

<400> SEQUENCE: 10

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Val His
                165                 170


<210> SEQ ID NO 11
<211> LENGTH: 175
<212> TYPE: PRT
<213> ORGANISM: Homo sapiens

<400> SEQUENCE: 11

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
```

```
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 12
<211> LENGTH: 175
<212> TYPE: PRT
<213> ORGANISM: Homo sapiens

<400> SEQUENCE: 12

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 13
<211> LENGTH: 175
<212> TYPE: PRT
<213> ORGANISM: Homo sapiens

<400> SEQUENCE: 13

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45
```

```
Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 14
<211> LENGTH: 175
<212> TYPE: PRT
<213> ORGANISM: Homo sapiens

<400> SEQUENCE: 14

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 15
<211> LENGTH: 175
<212> TYPE: PRT
<213> ORGANISM: Homo sapiens

<400> SEQUENCE: 15

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30
```

```
Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 16
<211> LENGTH: 175
<212> TYPE: PRT
<213> ORGANISM: Homo sapiens

<400> SEQUENCE: 16

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 17
<211> LENGTH: 175
<212> TYPE: PRT
<213> ORGANISM: Homo sapiens

<400> SEQUENCE: 17

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
```

```
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 18
<211> LENGTH: 175
<212> TYPE: PRT
<213> ORGANISM: Homo sapiens

<400> SEQUENCE: 18

Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175


<210> SEQ ID NO 19
<211> LENGTH: 137
<212> TYPE: PRT
<213> ORGANISM: Mus musculus

<400> SEQUENCE: 19

Ser Ser Cys Pro Lys Gly Ser Arg Ala Tyr Gly Ser Tyr Cys Tyr Ala
1               5                   10                  15
```

Leu Phe Ser Val Ser Lys Asn Trp Tyr Asp Ala Asp Met Ala Cys Gln
20 25 30

Lys Arg Pro Ser Gly His Leu Val Ser Val Leu Ser Gly Ala Glu Ala
35 40 45

Ser Phe Leu Ser Ser Met Ile Lys Ser Ser Gly Asn Ser Gly Gln Tyr
50 55 60

Val Trp Ile Gly Leu His Asp Pro Thr Leu Gly Tyr Glu Pro Asn Arg
65 70 75 80

Gly Gly Trp Glu Trp Ser Asn Ala Asp Val Met Asn Tyr Ile Asn Trp
85 90 95

Glu Thr Asn Pro Ser Ser Ser Ser Gly Asn His Cys Gly Thr Leu Ser
100 105 110

Arg Ala Ser Gly Phe Leu Lys Trp Arg Glu Asn Tyr Cys Asn Leu Glu
115 120 125

Leu Pro Tyr Val Cys Lys Phe Lys Ala
130 135

<210> SEQ ID NO 20
<211> LENGTH: 138
<212> TYPE: PRT
<213> ORGANISM: Mus musculus

<400> SEQUENCE: 20

Ile Ser Cys Pro Lys Gly Ser Gln Ala Tyr Gly Ser Tyr Cys Tyr Ala
1 5 10 15

Leu Phe Gln Ile Pro Gln Thr Trp Phe Asp Ala Glu Leu Ala Cys Gln
20 25 30

Lys Arg Pro Gly Gly His Leu Val Ser Val Leu Asn Ser Ala Glu Ala
35 40 45

Ser Phe Leu Ser Ser Met Val Lys Arg Thr Gly Asn Ser Tyr Gln Tyr
50 55 60

Thr Trp Ile Gly Leu His Asp Pro Thr Leu Gly Ala Glu Pro Asn Gly
65 70 75 80

Gly Gly Trp Glu Trp Ser Asn Asn Asp Val Met Asn Tyr Phe Asn Trp
85 90 95

Glu Arg Asn Pro Ser Thr Ala Leu Asp Arg Ala Phe Cys Gly Ser Leu
100 105 110

Ser Arg Ala Ser Gly Phe Leu Lys Trp Arg Asp Met Thr Cys Glu Val
115 120 125

Lys Leu Pro Tyr Val Cys Lys Phe Thr Gly
130 135

<210> SEQ ID NO 21
<211> LENGTH: 138
<212> TYPE: PRT
<213> ORGANISM: Homo sapiens

<400> SEQUENCE: 21

Ile Arg Cys Pro Lys Gly Ser Lys Ala Tyr Gly Ser His Cys Tyr Ala
1 5 10 15

Leu Phe Leu Ser Pro Lys Ser Trp Thr Asp Ala Asp Leu Ala Cys Gln
20 25 30

Lys Arg Pro Ser Gly Asn Leu Val Ser Val Leu Ser Gly Ala Glu Gly
35 40 45

Ser Phe Val Ser Ser Leu Val Lys Ser Ile Gly Asn Ser Tyr Ser Tyr
50 55 60

```
Val Trp Ile Gly Leu His Asp Pro Thr Gln Gly Thr Glu Pro Asn Gly
65                  70                  75                  80

Glu Gly Trp Glu Trp Ser Ser Ser Asp Val Met Asn Tyr Phe Ala Trp
                85                  90                  95

Glu Arg Asn Pro Ser Thr Ile Ser Ser Pro Gly His Cys Ala Ser Leu
            100                 105                 110

Ser Arg Ser Thr Ala Phe Leu Arg Trp Lys Asp Tyr Asn Cys Asn Val
        115                 120                 125

Arg Leu Pro Tyr Val Cys Lys Phe Thr Asp
    130                 135


<210> SEQ ID NO 22
<211> LENGTH: 2159
<212> TYPE: DNA
<213> ORGANISM: Mus musculus

<400> SEQUENCE: 22

gacagacaag atgcttcccc gtataaccat caccatcatg tcctggatgc tgctctcctg      60

cctgatgctc ctttctcagg tgcaaggtaa agttttgagt gtccagtgag tgtcccgtaa     120

gtgtccagta aaaaggcaaa agaaggttct ggagagtctc atgtggtaat gatgaagaga     180

gtcgtacata agacaactgc ctgaaacaaa accatcatcc tgccacctct gagtcactaa     240

tgacatatgg gtatcatgga agctctttcc tgaaattcct gagtttccaa ttttgctagc     300

aattttagct gatgacttga aggaaagtgt agaagtcaat aatgaactgt tgagataaag     360

aagggctgga tgggccaatt tagaaattga cagcgctaga attagggatc tacaaatcat     420

atgagaagag tgaagcatga aattaaaaga agaaaatttc ccataaagta ggtcaatctc     480

aagaccaaga tgactcttag agagaaagag tattctgtat tctgtattct gtgaagtcta     540

ttctgacgct atctgttctg gacttaatct caaacgccag gcctcatcaa catttgctaa     600

attgaccttt ctagacatta caccacactc ctttctttat ctccttccac tccaggtgaa     660

gttgccaaga aagatgcccc atcttcacgt agcagctgcc ccaagggctc ccgtgcctat     720

ggctcctatt gctatgcctt gtttagtgta tctaaaaact ggtatgatgc agatgtgagt     780

acttgaggat gcagaggagg gaaacaatgg gaggtacctg taagtcacaa aagaagtggg     840

ctccaatttc cacagtttct tgagaatcac aatgaacatt cagtacctct atcatctaca     900

tttgtttgcc attatctaat gaagtttcag tctgtcactc attctgcccc cttacctaga     960

tggcctgcca aaagaggccc tcaggacatc ttgtgtctgt gctcagtggc gctgaagctt    1020

ccttcctgtc ctccatgatc aaaagcagtg gtaacagtgg ccaatatgta tggattgggc    1080

tccatgaccc gacactggtg agatatcatc tcctcccatc tgatttctct ctcatcagtt    1140

ctgttcccaa gctcattttc tgtgtttcta tgagaaaaac ctgaattata actagagcta    1200

atattctgaa ttataactgg ggcaaaagaa agttcctaag ctctgtggaa gtccctagtc    1260

ttcagatgac atcaatgtga ctgtggttag cctttatgaa gttcctcaat gagggtttgc    1320

aaatctcttt tgtgagatta taggcatttg tacccatgat tttgagagaa cacaaaagag    1380

agaatatctg tatttgttct tcacattatc tatgtgggct ttgaagatca gagaaattta    1440

caaaggcata acctgttata ttctttgagg tctatgttat ttttttctgg gtttaatcag    1500

cttgtgatta tcactgggga tctgggaata ggagggagat gttcaggtta aattctggac    1560

agcacctgga agaatagatc aattccatga tgttgaccat taagcatcag ctattcccag    1620

taaggaatca tgcaagcaga gcttcagtga ctgctctctt ctcatggctg ccccaattct    1680

agggctatga acccaacaga ggtggatggg agtggagcaa tgctgatgtg atgaattaca    1740
```

```
tcaactggga gacgaatcct tcctcttcct caggcaatca ctgtggtacc ctgtcaagag   1800

cctcaggatt tctgaagtgg agagagaatt attgtaactt agagttaccc tatgtctgca   1860

aattcaaggc ctagagtaca gaattgacat catgggttga tatataccta gccacaagca   1920

agatcccaaa tgtgaagaca gatgaaaaag ggaacattct ccccacaatc gaaatctgac   1980

ctcctgattt tctccttctc tggcccttcc ctcctctcat ttgaggaact ctgtgtgcac   2040

tatggcctta attctcaaag cataatatta aagtatataa ctcatgctca aaaaaaaaaa   2100

aaaaaaaaaa aaaaaaaaaa aaaaaaaaaa aaaaaaaaaa aaaaaaaaaa aaaaaaaaa    2159
```

<210> SEQ ID NO 23
<211> LENGTH: 801
<212> TYPE: DNA
<213> ORGANISM: Mus musculus

<400> SEQUENCE: 23

```
accatcctag ggatctgcaa gacagacaag atgcttcccc gtataaccat caccatcatg     60

tcctggatgc tgctctcctg cctgatgctc ctttctcagg tgcaaggtga agttgccaag    120

aaagatgccc catcttcacg tagcagctgc cccaagggct cccgtgccta tggctcctat    180

tgctatgcct tgtttagtgt atctaaaaac tggtatgatg cagatatggc ctgccaaaag    240

aggccctcag gacatcttgt gtctgtgctc agtggcgctg aagcttcctt cctgtcctcc    300

atgatcaaaa gcagtggtaa cagtggccaa tatgtatgga ttgggctcca tgacccgaca    360

ctgggctatg aacccaacag aggtggatgg gagtggagca atgctgatgt gatgaattac    420

atcaactggg agacgaatcc ttcctcttcc tcaggcaatc actgtggtac cctgtcaaga    480

gcctcaggat ttctgaagtg gagagagaat tattgtaact tagagttacc ctatgtctgc    540

aaattcaagg cctagagtac agaattgaca tcatgggttg atatatacct agccacaagc    600

aagatcccaa atgtgaagac agatgaaaaa gggaacattc tccccacaat cgaaatctga    660

cctcctgatt ttctccttct ctggcccttc cctcctctca tttgaggaac tctgtgtgca    720

ctatggcctt aattctcaaa gcataatatt aaagtatata actcatgctc taaaaaaaaa    780

aaaaaaaaaa aaaaaaaaaa a                                              801
```

<210> SEQ ID NO 24
<211> LENGTH: 774
<212> TYPE: DNA
<213> ORGANISM: Mus musculus

<400> SEQUENCE: 24

```
acaccatcct agggatctgc aagacagaca agatgcttcc ccgtataacc atcaccatca     60

tgtcctggat gctgctctcc tgcctgatgc tcctttctca ggtgcaaggt gaagttgcca    120

agaaagatgc cccatcttca cgtagcagct gccccaaggg ctcccgtgcc tatggctcct    180

attgctatgc cttgtttagt gtatctaaaa actggtatga tgcagatatg gcctgccaaa    240

agaggccctc aggacatctt gtgtctgtgc tcagtggcgc tgaagcttcc ttcctgtcct    300

ccatgatcaa aagcagtggt aacagtggcc aatatgtatg gattgggctc catgacccga    360

cactgggcta tgaacccaac agaggtggat gggagtggag caatgctgat gtgatgaatt    420

acatcaactg ggagacgaat ccttcctctt cctcaggcaa tcactgtggt accctgtcaa    480

gagcctcagg atttctgaag tggagagaga attattgtaa cttagagtta ccctatgtct    540

gcaaattcaa ggcctagagt acagaattga catcatgggt tgatatatac ctagccacaa    600

gcaagatccc aaatgtgaag acagatgaaa aagggaacat tctccccaca atcgaaatct    660
```

```
gacctcctga ttttctcctt ctctggccct tccctcctct catttgagga actctgtgtg    720

cactatggcc ttaattctca aagcataata ttaaagtata taactcatgc tcat          774


<210> SEQ ID NO 25
<211> LENGTH: 774
<212> TYPE: DNA
<213> ORGANISM: Mus musculus

<400> SEQUENCE: 25

acaccatcct agggatctgc aagacagaca agatgcttcc ccgtataacc atcaccatca     60

tgtcctggat gctgctctcc tgcctgatgc tcctttctca ggtgcaaggt gaagttgcca    120

agaaagatgc cccatcttca cgtagcagct gccccaaggg ctcccgtgcc tatggctcct    180

attgctatgc cttgtttagt gtatctaaaa actggtatga tgcagatatg gcctgccaaa    240

agaggccctc aggacatctt gtgtctgtgc tcagtggcgc tgaagcttcc ttcctgtcct    300

ccatgatcaa aagcagtggt aacagtggcc aatatgtatg gattgggctc catgacccga    360

cactgggcta tgaacccaac agaggtggat gggagtggag caatgctgat gtgatgaatt    420

acatcaactg gagagacgaat ccttcctctt cctcaggcaa tcactgtggt accctgtcaa    480

gagcctcagg atttctgaag tggagagaga attattgtaa cttagagtta ccctatgtct    540

gcaaattcaa ggcctagagt acagaattga catcatgggt tgatatatac ctagccacaa    600

gcaagatccc aaatgtgaag acagatgaaa aagggaacat tctccccaca atcgaaatct    660

gacctcctga ttttctcctt ctctggccct tccctcctct catttgagga actctgtgtg    720

cactatggcc ttaattctca aagcataata ttaaagtata taactcatgc tcat          774


<210> SEQ ID NO 26
<211> LENGTH: 768
<212> TYPE: DNA
<213> ORGANISM: Mus musculus

<400> SEQUENCE: 26

gatcctaggg atctgcaaga cagacaagat gcttccccgt ataaccatca ccatcatgtc     60

ctggatgctg ctctcctgcc tgatgctcct ttctcaggtg caaggtgaag ttgccaagaa    120

agatgcccca tcttcacgta gcagctgccc caagggctcc cgtgcctatg gctcctattg    180

ctatgccttg tttagtgtat ctaaaaactg gtatgatgca gatatggcct gccaaaagag    240

gccctcagga catcttgtgt ctgtgctcag tggcgctgaa gcttccttcc tgtcctccat    300

gatcaaaagc agtggtaaca gtggccaata tgtatggatt gggctccatg acccgacact    360

gggctatgaa cccaacagag gtggatggga gtggagcaat gctgatgtga tgaattacat    420

caactgggag acgaatcctt cctcttcctc aggcaatcac tgtggtaccc tgtcaagagc    480

ctcaggattt ctgaagtgga gagagaatta ttgtaactta gagttaccct atgtctgcaa    540

attcaaggcc tagagtacag aattgacatc atgggttgat atatacctag ccacaagcaa    600

gatcccaaat gtgaagacag atgaaaaagg gaacattctc cccacaatcg aaatctgacc    660

tcctgatttt ctccttctct ggcccttccc tcctctcatt tgaggaactc tgtgtgcact    720

atggccttaa ttctcaaagc ataatattaa agtatataac tcatgctc                 768


<210> SEQ ID NO 27
<211> LENGTH: 768
<212> TYPE: DNA
<213> ORGANISM: Mus musculus

<400> SEQUENCE: 27
```

```
gatcctaggg atctgcaaga cagacaagat gcttccccgt ataaccatca ccatcatgtc     60

ctggatgctg ctctcctgcc tgatgctcct ttctcaggtg caaggtgaag ttgccaagaa    120

agatgcccca tcttcacgta gcagctgccc caagggctcc cgtgcctatg gctcctattg    180

ctatgccttg tttagtgtat ctaaaaactg gtatgatgca gatatggcct gccaaaagag    240

gccctcagga catcttgtgt ctgtgctcag tggcgctgaa gcttccttcc tgtcctccat    300

gatcaaaagc agtggtaaca gtggccaata tgtatggatt gggctccatg acccgacact    360

gggctatgaa cccaacagag gtggatggga gtggagcaat gctgatgtga tgaattacat    420

caactgggag acgaatcctt cctcttcctc aggcaatcac tgtggtaccc tgtcaagagc    480

ctcaggattt ctgaagtgga gagagaatta ttgtaactta gagttaccct atgtctgcaa    540

attcaaggcc tagagtacag aattgacatc atgggttgat atatacctag ccacaagcaa    600

gatcccaaat gtgaagacag atgaaaaagg gaacattctc cccacaatcg aaatctgacc    660

tcctgatttt ctccttctct ggcccttccc tcctctcatt tgaggaactc tgtgtgcact    720

atggccttaa ttctcaaagc ataatattaa agtatataac tcatgctc                 768
```

<210> SEQ ID NO 28
<211> LENGTH: 745
<212> TYPE: DNA
<213> ORGANISM: Mus musculus

<400> SEQUENCE: 28

```
aaggatgctg cctccaacag cctgctccgt catgtcctgg atgctgctct cctgcctgat     60

gctcttatct caggttcaag gtgaagactc cctgaagaat ataccctccg cacgcattag    120

ttgccccaag ggctcccagg cttatggctc ctactgctat gccttgtttc agataccaca    180

gacctggttt gatgcagaac tggcctgcca aaagaggcct ggaggacacc tcgtatctgt    240

gctcaatagc gctgaggctt cattcttgtc ctccatggtg aagagaacag gaaacagcta    300

ccaatacact tggattgggc tccatgaccc cactctgggt gcagaaccca atggcggtgg    360

atgggaatgg agtaacaatg acgtgatgaa ttactttaac tgggagagga acccatctac    420

tgccttagac cgtgctttct gtggcagctt gtcaagagct tctggatttc taaaatggag    480

agatatgaca tgtgaggtga agttgcccta tgtctgcaaa tttactggtt aaaattacca    540

gacagcaaaa atcgaattcc tcagcccggg ggatccacta gttctagagc ggccgccacc    600

gcggtggagc tccaattcgc cctatagtga gtcgtattac aattcactgg ccgtcgtttt    660

acaacgtcgt gactgggaaa accctggcgt tacccaactt aatcgccttg cacatcccct    720

ttcgccagct ggcgtaatag cgaag                                          745
```

<210> SEQ ID NO 29
<211> LENGTH: 759
<212> TYPE: DNA
<213> ORGANISM: Mus musculus

<400> SEQUENCE: 29

```
acaccatcca gatctctgga agacagacaa gatgctgcct ccaacagcct gctccgtcat     60

gtcctggatg ctgctctcct gcctgatgct cttatctcag gttcaaggtg aagactccct    120

gaagaatata ccctccgcac gcattagttg ccccaagggc tcccaggctt atggctccta    180

ctgctatgcc ttgtttcaga taccacagac ctggtttgat gcagaactgg cctgccaaaa    240

gaggcctgga ggacacctcg tatctgtgct caatagcgct gaggcttcat tcttgtcctc    300

catggtgaag agaacaggaa acagctacca atacacttgg attgggctcc atgaccccac    360
```

```
tctgggtgca gaacccaatg gaggtggatg ggaatggagt aacaatgacg tgatgaatta    420
ctttaactgg gagaggaacc catctactgc cttagaccgt gctttctgtg gcagcttgtc    480
aagagcttct ggatttctaa aatggagaga tatgacatgt gaggtgaagt tgccctatgt    540
ctgcaaattt actggttaaa cttatcagac agcaaacatc ccgaatttgt cttgaagagc    600
atcatggaca agggacaaaa tgtgaagact cacctagaaa aagcattttc tatctacagt    660
ccacattaga gccttaatct gctctttcca tatctgtctt tagtcctttt ggtataagtt    720
tgggctcaat tctaaaataa aaataagctt tctgtcaca                            759
```

<210> SEQ ID NO 30
<211> LENGTH: 759
<212> TYPE: DNA
<213> ORGANISM: Mus musculus

<400> SEQUENCE: 30

```
acaccatcca gatctctgga agacagacaa gatgctgcct ccaacagcct gctccgtcat     60
gtcctggatg ctgctctcct gcctgatgct cttatctcag gttcaaggtg aagactccct    120
gaagaatata ccctccgcac gcattagttg ccccaagggc tcccaggctt atggctccta    180
ctgctatgcc ttgtttcaga taccacagac ctggtttgat gcagaactgg cctgccaaaa    240
gaggcctgga ggacacctcg tatctgtgct caatagcgct gaggcttcat tcttgtcctc    300
catggtgaag agaacaggaa acagctacca atacacttgg attgggctcc atgaccccac    360
tctgggtgca gaacccaatg gaggtggatg ggaatggagt aacaatgacg tgatgaatta    420
ctttaactgg gagaggaacc catctactgc cttagaccgt gctttctgtg gcagcttgtc    480
aagagcttct ggatttctaa aatggagaga tatgacatgt gaggtgaagt tgccctatgt    540
ctgcaaattt actggttaaa cttatcagac agcaaacatc ccgaatttgt cttgaagagc    600
atcatggaca agggacaaaa tgtgaagact cacctagaaa aagcattttc tatctacagt    660
ccacattaga gccttaatct gctctttcca tatctgtctt tagtcctttt ggtataagtt    720
tgggctcaat tctaaaataa aaataagctt tctgtcaca                            759
```

<210> SEQ ID NO 31
<211> LENGTH: 778
<212> TYPE: DNA
<213> ORGANISM: Mus musculus

<400> SEQUENCE: 31

```
ggaagacaga caagatgctg cctccaacag cctgctccgt catgtcctgg atgctgctct     60
cctgcctgat gctcttatct caggttcaag gtgaagactc cctgaagaat ataccctccg    120
cacgcattag ttgccccaag ggctcccagg cttatggctc ctactgctat gccttgtttc    180
agataccaca gacctggttt gatgcagaac tggcctgcca aaagaggcct ggaggacacc    240
tcgtatctgt gctcaatagc gctgaggctt cattcttgtc ctccatggtg aagagaacag    300
gaaacagcta ccaatacact tggattgggc tccatgaccc cactctgggt gcagaaccca    360
atggaggtgg atgggaatgg agtaacaatg acgtgatgaa ttactttaac tgggagagga    420
acccatctac tgccttagac cgtgctttct gtggcagctt gtcaagagct tctggatttc    480
taaaatggag agatatgaca tgtgaggtga agttgcccta tgtctgcaaa tttactggtt    540
aaacttatca gacagcaaac atcccgaatt tgtcttgaag agcatcatgg acaagggaca    600
aaatgtgaag actcacctag aaaaagcatt ttctatctac agtccacatt agagccttaa    660
tctgctcttt ccatatctgt ctttagtcct tttggtataa gtttgggctc aattctaaaa    720
```

taaaaataag ctttctgtca aaaaaaaaaa aaaaaaaaaa aaaaaaaaaa aaaaaaaa 778

<210> SEQ ID NO 32
<211> LENGTH: 798
<212> TYPE: DNA
<213> ORGANISM: Homo sapiens

<400> SEQUENCE: 32
cgggagagtg actcctgatt gcctcctcaa gtcgcagaca ctatgctgcc tcccatggcc 60
ctgcccagtg tatcttggat gctgctttcc tgcctcatgc tgctgtctca ggttcaaggt 120
gaagaacccc agagggaact gccctctgca cggatccgct gtcccaaagg ctccaaggcc 180
tatggctccc actgctatgc cttgtttttg tcaccaaaat cctggacaga tgcagatctg 240
gcctgccaga agcggccctc tggaaacctg gtgtctgtgc tcagtggggc tgagggatcc 300
ttcgtgtcct ccctggtgaa gagcattggt aacagctact catacgtctg gattgggctc 360
catgacccca cacagggcac cgagcccaat ggagaaggtt gggagtggag tagcagtgat 420
gtgatgaatt actttgcatg ggagagaaat ccctccacca tctcaagccc cggccactgt 480
gcgagcctgt cgagaagcac agcatttctg aggtggaaag attataactg taatgtgagg 540
ttaccctatg tctgcaaagt tcactgacta gtgcaggagg gaagtcagca gcctgtgttt 600
ggtgtgcaac tcatcatggg catgagacca gtgtgaggac tcaccctgga agagaatatt 660
cgcttaattc cccaacctg accacctcat tcttatcttt cttctgtttc ttcctccccg 720
ctagtcattt cagtctcttc attttgtcat acggcctaag gctttaaaga gcaataaaat 780
ttttagtctg caaaaaaa 798

<210> SEQ ID NO 33
<211> LENGTH: 807
<212> TYPE: DNA
<213> ORGANISM: Homo sapiens

<400> SEQUENCE: 33
aaaccatacc atatcccacc agagagtgac tcctgattgc ctcctcaagt cgcagacact 60
atgctgcctc ccatggccct gcccagtgta tcttggatgc tgctttcctg cctcatgctg 120
ctgtctcagg ttcaaggtga agaaccccag agggaactgc cctctgcacg gatccgctgt 180
cccaaaggct ccaaggccta tggctcccac tgctatgcct tgtttttgtc accaaaatcc 240
tggacagatg cagatctggc ctgccagaag cggccctctg gaaacctggt gtctgtgctc 300
agtggggctg agggatcctt cgtgtcctcc ctggtgaaga gcattggtaa cagctactca 360
tacgtctgga ttgggctcca tgaccccaca cagggcaccg agcccaatgg agaaggttgg 420
gagtggagta gcagtgatgt gatgaattac tttgcatggg agagaaatcc ctccaccatc 480
tcaagccccg gccactgtgc gagcctgtcg agaagcacag catttctgag gtggaaagat 540
tataactgta atgtgaggtt accctatgtc tgcaagttca ctgactagtg caggagggaa 600
gtcagcagcc tgtgtttggt gtgcaactca tcatgggcat gagaccagtg tgaggactca 660
ccctggaaga gaatattcgc ttaattcccc caacctgacc acctcattct tatctttctt 720
ctgtttcttc ctccccgctg tcatttcagt ctcttcattt tgtcatacgg cctaaggctt 780
taaagagcaa taaaattttt agtctgc 807

<210> SEQ ID NO 34
<211> LENGTH: 599
<212> TYPE: DNA
<213> ORGANISM: Homo sapiens

<400> SEQUENCE: 34

```
ctcctgattg cctcctcaag tcgcagacac tatgctgcct cccatggccc tgcccagtgt     60
atcttggatg ctgctttcct gcctcatgct gctgtctcag gttcaaggtg aagaacccca    120
gagggaactg ccctctgcac ggatccgctg tcccaaaggc tccaaggcct atggttccca    180
ctgctatgcc ttgtttttgt caccaaaatc ctggacagat gcagatctgg cctgccagaa    240
gcggccctct ggaaacctgg tgtctgtgct cagtggggct gagggatcct tcgtgtcctc    300
cctggtgaag agcattggta acagctactc atacgtctgg attgggctcc atgaccccac    360
acagggcacc gagcccaatg gagaaggttg ggagtggagt agcagtgatg tgatgaatta    420
ctttgcatgg gagagaaatc cctccaccat ctcaagcccc ggccactgtg cgagcctgtc    480
gagaagcaca gcatttctga ggtggaaaga ttataactgt aatgtgaggt taccctatgt    540
ctgcaagttc actgactagt gcaggaggga agtcagcagc ctgtgtttgg tgtgcaact     599
```

<210> SEQ ID NO 35
<211> LENGTH: 688
<212> TYPE: DNA
<213> ORGANISM: Homo sapiens

<400> SEQUENCE: 35

```
atgaggcagt ggggtatctg tgtgttctcc cactgaccac gctttcttta gtgactcctg     60
attgcctcct caagtcgcag acactatgct gcctcccatg gccctgccca gtgtatcttg    120
gatgctgctt tcctgcctca tgctgctgtc tcaggttcaa ggtgaagaac cccagaggga    180
actgccctct gcacggatcc gctgtcccaa aggctccaag gcctatggct cccactgcta    240
tgccttgttt ttgtcaccaa aatcctggac agatgcagat ctggcctgcc agaagcggcc    300
ctctggaaac ctggtgtctg tgctcagtgg ggctgaggga tccttcgtgt cctccctggt    360
gaagagcatt ggtaacagct actcatacgt ctggattggg ctccatgacc ccacacaggg    420
caccgagccc aatggagaag gttgggagtg gagtagcagt gatgtgatga attactttgc    480
atgggagaga aatccctcca ccatctcaag ccccggccac tgtgcgagcc tgtcgagaag    540
cacagcattt ctgaggtgga aagattataa ctgtaatgtg aggttaccct atgtctgcaa    600
gttcactgac tagtgcagga gggaagtcag cagcctgtgt ttggtgtgca actcatcatg    660
ggcatgagac cagtgtgagg actcaccc                                       688
```

<210> SEQ ID NO 36
<211> LENGTH: 568
<212> TYPE: DNA
<213> ORGANISM: Artificial
<220> FEATURE:
<223> OTHER INFORMATION: Synthetic construct

<400> SEQUENCE: 36

```
gtacaaaaaa gcaggctcca ccatgctgcc tcccatggcc ctgcccagtg tatcttggat     60
gctgctttcc tgcctcatgc tgctgtctca ggttcaaggt gaagaacccc agagggaact    120
gccctctgca cggatccgct gtcccaaagg ctccaaggcc tatggctccc actgctatgc    180
cttgtttttg tcaccaaaat cctggacaga tgcagatctg gcctgccaga agcggccctc    240
tggaaacctg gtgtctgtgc tcagtggggc tgagggatcc ttcgtgtcct ccctggtgaa    300
gagcattggt aacagctact catacgtctg gattgggctc catgacccca cacagggcac    360
cgagcccaat ggagaaggtt gggagtggag tagcagtgat gtgatgaatt actttgcatg    420
ggagagaaat ccctccacca tctcaagccc cggccactgt gcgagcctgt cgagaagcac    480
```

agcatttctg aggtggaaag attataactg taatgtgagg ttaccctatg tctgcaagtt 540
cactgacttg gacccagctt tcttgtac 568

<210> SEQ ID NO 37
<211> LENGTH: 1002
<212> TYPE: DNA
<213> ORGANISM: Homo sapiens

<400> SEQUENCE: 37
gggagggtcc cttcctcagg gagcacagga actctgagac tcagcaaggg tgtcctggga 60
gggctcgggg atgggagagt acacagattc acaactcatt cagaactgta gaagatgatg 120
gatgtgacca agatcacttt agtcctaggg gactagagaa ggaaaatgac atgaggcagt 180
ggggtatctg tgtgttctcc cactgaccac gctttcttta gtgactcctg attgcctcct 240
caagtcgcag acactatgct gcctcccatg gccctgccca gtgtatcttg gatgctgctt 300
tcctgcctca tgctgctgtc tcaggttcaa ggtgaagaac cccagaggga actgccctct 360
gcacggatcc gctgtcccaa aggctccaag gcctatggct cccactgcta tgccttgttt 420
ttgtcaccaa aatcctggac agatgcagat ctggcctgcc agaagcggcc ctctggaaac 480
ctggtgtctg tgctcagtgg ggctgaggga tccttcgtgt cctccctggt gaagagcatt 540
ggtaacagct actcatacgt ctggattggg ctccatgacc ccacacaggg caccgagccc 600
aatggagaag gttgggagtg gagtagcagt gatgtgatga attactttgc atgggagaga 660
aatccctcca ccatctcaag ccccggccac tgtgcgagcc tgtcgagaag cacagcattt 720
ctgaggtgga aagattataa ctgtaatgtg aggttaccct atgtctgcaa gttcactgac 780
tagtgcagga gggaagtcag cagcctgtgt ttggtgtgca actcatcatg ggcatgagac 840
cagtgtgagg actcaccctg gaagagaata ttcgcttaat tcccccaacc tgaccacctc 900
attcttatct ttcttctgtt tcttcctccc cgctgtcatt tcagtctctt cattttgtca 960
tacggcctaa ggctttaaag agcaataaaa tttttagtct gc 1002

<210> SEQ ID NO 38
<211> LENGTH: 784
<212> TYPE: DNA
<213> ORGANISM: Homo sapiens

<400> SEQUENCE: 38
aaaccatacc atatcccacc agagagtcgc agacactatg ctgcctccca tggccctgcc 60
cagtgtatct tggatgctgc tttcctgcct catgctgctg tctcaggttc aaggtgaaga 120
accccagagg gaactgccct ctgcacggat ccgctgtccc aaaggctcca aggcctatgg 180
ctcccactgc tatgccttgt ttttgtcacc aaaatcctgg acagatgcag atctggcctg 240
ccagaagcgg ccctctggaa acctggtgtc tgtgctcagt ggggctgagg gatccttcgt 300
gtcctccctg gtgaagagca ttggtaacag ctactcatac gtctggattg ggctccatga 360
ccccacacag ggcaccgagc ccaatggaga aggttgggag tggagtagca gtgatgtgat 420
gaattacttt gcatgggaga gaaatccctc caccatctca agccccggcc actgtgcgag 480
cctgtcgaga agcacagcat ttctgaggtg gaaagattat aactgtaatg tgaggttacc 540
ctatgtctgc aagttcactg actagtgcag gagggaagtc agcagcctgt gtttggtgtg 600
caactcatca tgggcatgag accagtgtga ggactcaccc tggaagagaa tattcgctta 660
attcccccaa cctgaccacc tcattcttat ctttcttctg tttcttcctc cccgctgtca 720
tttcagtctc ttcattttgt catacggcct aaggctttaa agagcaataa aatttttagt 780
ctgc 784

<210> SEQ ID NO 39
<211> LENGTH: 760
<212> TYPE: DNA
<213> ORGANISM: Homo sapiens

<400> SEQUENCE: 39
agtcgcagac actatgctgc ctcccatggc cctgcccagt gtatcttgga tgctgctttc 60
ctgcctcatg ctgctgtctc aggttcaagg tgaagaaccc cagagggaac tgccctctgc 120
acggatccgc tgtcccaaag gctccaaggc ctatggctcc cactgctatg ccttgttttt 180
gtcaccaaaa tcctggacag atgcagatct ggcctgccag aagcggccct ctggaaacct 240
ggtgtctgtg ctcagtgggg ctgagggatc cttcgtgtcc tccctggtga agagcattgg 300
taacagctac tcatacgtct ggattgggct ccatgacccc acacagggca ccgagcccaa 360
tggagaaggt tgggagtgga gtagcagtga tgtgatgaat tactttgcat gggagagaaa 420
tccctccacc atctcaagcc ccggccactg tgcgagcctg tcgagaagca cagcatttct 480
gaggtggaaa gattataact gtaatgtgag gttaccctat gtctgcaagt tcactgacta 540
gtgcaggagg gaagtcagca gcctgtgttt ggtgtgcaac tcatcatggg catgagacca 600
gtgtgaggac tcaccctgga agagaatatt cgcttaattc cccaacctga accacctcat 660
tcttatcttt cttctgtttc ttcctccccg ctgtcatttc agtctcttca ttttgtcata 720
cggcctaagg ctttaaagag caataaaatt tttagtctgc 760

<210> SEQ ID NO 40
<211> LENGTH: 797
<212> TYPE: DNA
<213> ORGANISM: Homo sapiens

<400> SEQUENCE: 40
cgggagagtg actcctgatt gcctcctcaa gtcgcagaca ctatgctgcc tcccatggcc 60
ctgcccagtg tatcttggat gctgctttcc tgcctcatgc tgctgtctca ggttcaaggt 120
gaagaacccc agagggaact gccctctgca cggatccgct gtcccaaagg ctccaaggcc 180
tatggctccc actgctatgc cttgtttttg tcaccaaaat cctggacaga tgcagatctg 240
gcctgccaga agcggccctc tggaaacctg gtgtctgtgc tcagtggggc tgagggatcc 300
ttcgtgtcct ccctggtgaa gagcattggt aacagctact catacgtctg gattgggctc 360
catgacccca cacagggcac cgagcccaat ggagaaggtt gggagtggag tagcagtgat 420
gtgatgaatt actttgcatg ggagagaaat ccctccacca tctcaagccc cggccactgt 480
gcgagcctgt cgagaagcac agcatttctg aggtggaaag attataactg taatgtgagg 540
ttaccctatg tctgcaagtt cactgactag tgcaggaggg aagtcagcag cctgtgtttg 600
gtgtgcaact catcatgggc atgagaccag tgtgaggact caccctggaa gagaatattc 660
gcttaattcc cccaacctga ccacctcatt cttatctttc ttctgtttct tcctccccgc 720
tagtcatttc agtctcttca ttttgtcata cggcctaagg ctttaaagag caataaaatt 780
tttagtctgc aaaaaaa 797

<210> SEQ ID NO 41
<211> LENGTH: 784
<212> TYPE: DNA
<213> ORGANISM: Homo sapiens

<400> SEQUENCE: 41
agtgactcct gattgccatc ctcaagtcgc agacactatg ctgcctccca tggccctgcc 60
cagtgtatct tggatgctgc tttcctgcct catgctgctg tctcaggttc aaggtgaaga 120
accccagagg gaactgccct ctgcacggat ccgctgtccc aaaggctcca aggcctatgg 180
ctcccactgc tatgccttgt ttttgtcacc aaaatcctgg acagatgcag atctggcctg 240
ccagaagcgg ccctctggaa acctggtgtc tgtgctcagt ggggctgagg gatccttcgt 300
gtcctccctg gtgaagagca ttggtaacag ctactcatac gtctggattg ggctccatga 360
ccccacacag ggcaccgagc ccaatggaga aggttgggag tggagtagca gtgatgtgat 420
gaattacttt gcatgggaga gaaatccctc caccatctca agccccggcc actgtgcgag 480
cctgtcgaga agcacagcat ttctgaggtg gaaagattat aactgtaatg tgaggttacc 540
ctatgtctgc aagttcactg actagtgcag gagggaagtc agcagcctgt gtttggtgtg 600
caactcatca tgggcatgag accagtgtga ggactcaccc tggaagagaa tattcgctta 660
attcccccaa cctgaccacc tcattcttat ctttcttctg tttcttcctc cccgctgtca 720
tttcagtctc ttcattttgt catacggcct aaggctttaa agagcaataa aatttttagt 780
ctgc 784

<210> SEQ ID NO 42
<211> LENGTH: 846
<212> TYPE: DNA
<213> ORGANISM: Homo sapiens

<400> SEQUENCE: 42
ccagagagtg actcctgatt gcctcctcaa gtcgcagaca ctatgctgcc tcccatggcc 60
ctgcccagtg tatcttggat gctgctttcc tgcctcatgc tgctgtctca ggttcaaggt 120
gaagaacccc agagggaact gccctctgca cggatccgct gtcccaaagg ctccaaggcc 180
tatggctccc actgctatgc cttgtttttg tcaccaaaat cctggacaga tgcagatctg 240
gcctgccaga agcggccctc tggaaacctg gtgtctgtgc tcagtggggc tgagggatcc 300
ttcgtgtcct ccctggtgaa gagcattggt aacagctact catacgtctg gattgggctc 360
catgacccca cacagggcac cgagcccaat ggagaaggtt gggagtggag tagcagtgat 420
gtgatgaatt actttgcatg ggagagaaat ccctccacca tctcaagccc cggccactgt 480
gcgagcctgt cgagaagcac agcatttctg aggtggaaag attataactg taatgtgagg 540
ttaccctatg tctgcaagtt cactgactag tgcaggaggg aagtcagcag cctgtgtttg 600
gtgtgcaact catcatgggc atgagaccag tgtgaggact caccctggaa gagaatattc 660
gcttaattcc cccaacctga ccacctcatt cttatctttc ttctgtttct tcctccccgc 720
tgtcatttca gtctcttcat tttgtcatac ggcctaaggc tttaaagagc aataaaattt 780
ttagtctgca aaaaaaaaaa aaaaaaaaaa aaaaaaaaaa aaaaaaaaaa aaaaaaaaaa 840
aaaaaa 846

<210> SEQ ID NO 43
<211> LENGTH: 417
<212> TYPE: DNA
<213> ORGANISM: Homo sapiens

<400> SEQUENCE: 43
atgagtagtt gtcctaaggg ctcccgtgcc tatggctcct attgctatgc cttgtttagt 60
gtatctaaaa actggtatga tgcagatatg gcctgccaaa agaggccctc aggacatctt 120
gtgtctgtgc tcagtggcgc tgaagcttcc ttcctgtcct ccatgatcaa aagcagtggt 180
aacagtggcc aatatgtatg gattgggctc catgacccga cactgggcta tgaacccaac 240
agaggtggat gggagtggag caatgctgat gtgatgaatt acatcaactg ggagacgaat 300
ccttcctctt cctcaggcaa tcactgtggt accctgtcaa gagcctcagg atttctgaag 360
tggagagaga attattgtaa cttagagtta ccctatgtct gcaaattcaa ggcctag 417

<210> SEQ ID NO 44
<211> LENGTH: 417
<212> TYPE: DNA
<213> ORGANISM: Mus musculus

<400> SEQUENCE: 44
atgattcgat gtccaaaagg ctccaaggcc tatggctccc actgctatgc cttgtttttg 60
tcaccaaaat cctggacaga tgcagatctg gcctgccaga agcggccctc tggaaacctg 120
gtgtctgtgc tcagtggggc tgagggatcc ttcgtgtcct ccctggtgaa gagcattggt 180
aacagctact catacgtctg gattgggctc catgacccca cacagggcac cgagcccaat 240
ggagaaggtt gggagtggag tagcagtgat gtgatgaatt actttgcatg ggagagaaat 300
ccctccacca tctcaagccc cggccactgt gcgagcctgt cgagaagcac agcatttctg 360
aggtggaaag attataactg taatgtgagg ttaccctatg tctgcaaagt tcactga 417

<210> SEQ ID NO 45
<211> LENGTH: 450
<212> TYPE: DNA
<213> ORGANISM: Mus musculus

<400> SEQUENCE: 45
atggaagaac cacaaagaga actgccctct gcacggatcc gctgtcccaa aggctccaag 60
gcctatggct cccactgcta tgccttgttt ttgtcaccaa aatcctggac agatgcagat 120
ctggcctgcc agaagcggcc ctctggaaac ctggtgtctg tgctcagtgg ggctgaggga 180
tccttcgtgt cctccctggt gaagagcatt ggtaacagct actcatacgt ctggattggg 240
ctccatgacc ccacacaggg caccgagccc aatggagaag gttgggagtg gagtagcagt 300
gatgtgatga attactttgc atgggagaga aatccctcca ccatctcaag ccccggccac 360
tgtgcgagcc tgtcgagaag cacagcattt ctgaggtgga aagattataa ctgtaatgtg 420
aggttaccct atgtctgcaa agttcactga 450

<210> SEQ ID NO 46
<211> LENGTH: 40
<212> TYPE: DNA
<213> ORGANISM: Artificial
<220> FEATURE:
<223> OTHER INFORMATION: Synthetic primer

<400> SEQUENCE: 46
attgcgaggc atatggaagt tgccaagaaa gatgccccat 40

<210> SEQ ID NO 47
<211> LENGTH: 40
<212> TYPE: DNA
<213> ORGANISM: Artificial
<220> FEATURE:
<223> OTHER INFORMATION: Synthetic primer

<400> SEQUENCE: 47
ctatggggat ccctaggcct tgaatttgca gacatagggt 40

<210> SEQ ID NO 48
<211> LENGTH: 38
<212> TYPE: DNA
<213> ORGANISM: Artificial
<220> FEATURE:
<223> OTHER INFORMATION: Synthetic primer

<400> SEQUENCE: 48
attgcgaggc atatggaaga accccagaga ggaactgc 38

<210> SEQ ID NO 49
<211> LENGTH: 42
<212> TYPE: DNA
<213> ORGANISM: Artificial
<220> FEATURE:
<223> OTHER INFORMATION: Synthetic primer

<400> SEQUENCE: 49
ctatggtgat cactagtcag tgaacttgca gacatagggt aa 42

<210> SEQ ID NO 50
<211> LENGTH: 38
<212> TYPE: DNA
<213> ORGANISM: Artificial
<220> FEATURE:
<223> OTHER INFORMATION: Synthetic primer

<400> SEQUENCE: 50
attgcgaggc atatggaaga accacaaaga gaaactgc 38

<210> SEQ ID NO 51
<211> LENGTH: 22
<212> TYPE: DNA
<213> ORGANISM: Artificial
<220> FEATURE:
<223> OTHER INFORMATION: Synthetic primer

<400> SEQUENCE: 51
ttcctgtcct ccatgatcaa aa 22

<210> SEQ ID NO 52
<211> LENGTH: 21
<212> TYPE: DNA
<213> ORGANISM: Artificial
<220> FEATURE:
<223> OTHER INFORMATION: Synthetic primer

<400> SEQUENCE: 52
catccacctc tgttgggttc a 21

<210> SEQ ID NO 53
<211> LENGTH: 21
<212> TYPE: DNA
<213> ORGANISM: Artificial
<220> FEATURE:
<223> OTHER INFORMATION: Synthetic primer

<400> SEQUENCE: 53
cattcgaacg tctgccctat c 21

<210> SEQ ID NO 54
<211> LENGTH: 18
<212> TYPE: DNA
<213> ORGANISM: Artificial
<220> FEATURE:
<223> OTHER INFORMATION: Synthetic primer

<400> SEQUENCE: 54

-continued

```
cctgctgcct tccttgga                                                   18


<210> SEQ ID NO 55
<211> LENGTH: 24
<212> TYPE: DNA
<213> ORGANISM: Artificial
<220> FEATURE:
<223> OTHER INFORMATION: Synthetic primer

<400> SEQUENCE: 55

atcatccagg tgattcccag ccat                                            24


<210> SEQ ID NO 56
<211> LENGTH: 24
<212> TYPE: DNA
<213> ORGANISM: Artificial
<220> FEATURE:
<223> OTHER INFORMATION: Synthetic primer

<400> SEQUENCE: 56

ttccgggtct ccaaaggaaa caga                                            24
```

EXPRESSION AND PURIFICATION OF HIP/PAP AND USES THEREFOR

PRIORITY CLAIM

The present applications claims benefit of priority to U.S. Provisional Application Ser. Nos. 60/889,424, and 60/970,462, filed Feb. 12, 2007 and Sep. 6, 2007, respectively. The entire contents of both applications is hereby incorporated by reference.

STATEMENT REGARDING FEDERALLY SPONSORED RESEARCH OR DEVELOPMENT

This invention was made in part with government support under Grant No. RO1 DK070855 awarded by the National Institutes of Health. The United States Government has certain rights in the invention.

TECHNICAL FIELD

The present invention relates to the fields of pharmacology, molecular biology, biochemistry, and medicine. More particularly, the present invention relates to antimicrobial compositions comprising regenerating (Reg) proteins that have antibacterial activity. The invention also relates to expression and purification system for producing large quantities of Reg proteins, and method of using Reg proteins for antimicrobial treatments and diagnostics.

BACKGROUND OF THE INVENTION

Epithelial antimicrobial proteins are evolutionarily ancient innate immune effectors. As key elements of intestinal mucosal defense, they likely play an important role in maintaining mutually-beneficial host-microbial relationships by restricting contact between resident microbes and mucosal surfaces. This idea is underscored by the fact that deficiencies in antimicrobial peptide expression are associated with inflammatory bowel disease (Wehkamp et al., 2004; Wehkamp et al., 2005), a chronic inflammatory disorder thought to be triggered by resident gut microbes. However, although cationic antimicrobial peptides such as defensins are well-characterized, the full repertoire of gut antimicrobial mechanisms remains undefined.

C-type lectins are proteins that contain carbohydrate recognition domains (CRDs) and bind selectively to specific carbohydrate structures, often in a $Ca^{2+}$-dependent manner. They mediate a variety of functions including cellular adhesion, clearance of circulating proteins, and recognition of microbe-associated molecular patterns (reviewed in Drickamer et al., 1993). The Reg gene family encodes an extensive group of secreted proteins that contain conserved sequence motifs found in all C-type lectin CRDs. The family is so named because the first member to be identified was cloned from a cDNA library derived from regenerating pancreatic islets (Terazono et al., 1988). Subsequently, several members of this multigene family have been identified in mice and humans, and are grouped according to homology into four subfamilies: RegI, RegII, RegIII, and RegIV. Despite their similarities to well-characterized C-type lectins, the members of the Reg family have poorly defined functions and their carbohydrate ligands have not been clearly identified.

Members of the RegIII family are constitutively expressed at high levels in mouse and human gastrointestinal tissues. RegIIIα, β, and γ are expressed in mouse small intestine (Narushima et al., 1997), while human hepatocarcinoma-intestine-pancreas/pancreatitis associated protein (HIP/PAP) is made in human small intestine. RegIIIβ and γ expression levels increase dramatically in response to bacterial colonization and other inflammatory stimuli in mice (Ogawa et al., 2000; Ogawa et al., 2003; Keilbaugh et al., 2005). In addition, HIP/PAP expression is upregulated in the mucosal tissues of patients with inflammatory bowel disease Ogawa et al., 2003; Dieckgraefe et al., 2002). Despite these insights into the forces regulating RegIII protein expression, almost nothing is known about the biological functions of RegIII proteins or their role in disease.

An abundant source of purified recombinant mouse and human RegIII proteins is needed to delineate the role of RegIII proteins in intestinal biology and human disease. Human HIP/PAP has been purified previously from the milk of transgenic mice engineered to express the protein in mammary gland (Christa et al., 2000), and as a glutathione S-transferase (GST) fusion protein in an *E. coli* expression system (Christa et al., 1994). Although the transgenic approach yielded quantities of protein sufficient for crystallographic analysis (Abergel et al., 1999), this method is technically challenging, time-consuming, and expensive. The recombinant fusion protein procedure produced only microgram quantities of the GST-tagged protein (Christa et al., 1994). Thus, a simple expression and purification system is needed to generate large quantities of Reg proteins to further characterize their roles as antimicrobial proteins.

SUMMARY OF THE INVENTION

The present invention relates to antimicrobial compositions comprising Reg proteins, more specifically, mouse RegIIIγ, mouse RegIIIβ and human HIP/PAP, and the uses of these compositions to enhance innate immunity and/or reduce or inhibit bacterial colonization or growth. In certain embodiments, the antimicrobial composition is bactericidal.

One embodiment comprises an antimicrobial composition comprising a pharmaceutical carrier admixed with an isolated protein, wherein said protein is: (1) an amino acid sequence selected from the group consisting of SEQ ID NO:19, SEQ ID NO:20, and SEQ ID NO:21, or (2) an isolated nucleic acid molecule encoding an amino acid sequence of (1) having a silent mutation within the coding region, wherein the mutation is a C→T, C→A, G→T or G→A. In certain embodiments, wherein the protein is a peptiodoglycan-binding protein.

Another embodiment of the present invention comprises a method of treating an inflammatory bowel disease comprising administering to a subject an effective amount of the antimicrobial composition.

Yet further, another embodiment comprises a method of treating a bacterial infection comprising administering to a subject an effective amount of the antimicrobial composition.

Another embodiment of the present invention comprises an expression vector comprising a nucleic acid sequence selected from the group consisting of: (1) a nucleic acid molecule encoding an amino acid sequence selected from the group consisting of SEQ ID NO:19, SEQ ID NO:20, and SEQ ID NO:21, or; (2) an isolated nucleic acid molecule encoding an amino acid sequence of (1) having a silent mutation within the coding region, wherein the mutation is a C→T, C→A, G→T or G→A. In certain embodiments, the vector is a bacterial vector.

Still further, another embodiment comprises a method for producing a regenerating protein (Reg) comprising culturing a transformed host cell, for example, a prokaryotic cell, containing the expression vector containing a nucleic acid sequence selected from the group consisting of: (1) a nucleic acid molecule encoding an amino acid sequence selected from the group consisting of SEQ ID NO:19, SEQ ID NO:20, and SEQ ID NO:21, or; (2) an isolated nucleic acid molecule encoding an amino acid sequence of (1) having a silent mutation within the coding region, wherein the mutation is a C→T, C→A, G→T or G→A in a suitable nutrient medium until the Reg protein is produced. The method also comprises isolating the produced protein. In certain embodiments, the prokaryotic cell is *Escherichia coli.*

Another method of the present invention comprises a method of enhancing innate immunity of a subject comprising administering to the subject an effective amount of an antimicrobial composition that increases the expression and/or activity of a regenerating protein (Reg) in the gastrointestinal system of the subject thereby enhancing innate immunity. The Reg protein can be RegIII, more specifically, human hepatocarcinoma-intestine-pancreas/pancreatic-associated protein (HIP/PAP).

In certain embodiments, the subject is susceptible to or is suffering from gastrointestinal pathogenic bacteria colonization. Yet further, the subject is susceptible to or is suffering from inflammatory bowel disease, for example, the inflammatory bowel disease can be ulcerative colitis or Crohn's disease.

Yet further, the antimicrobial composition may also be administered in combination with a second therapeutic composition, for example, anti-inflammatory agents (e.g., salicylates or corticosteroids), immune modifiers (e.g., anti-TNF agents or interleukin 11), and antibiotics (e.g., metronidazole or ciprofloxacin).

Another method of the present invention comprises a method of decreasing gastrointestinal pathogenic bacteria in a subject comprising administering to the subject an effective amount of an antimicrobial composition that increases the expression and/or activity of a regenerating protein (Reg) in the gastrointestinal system of the subject, thereby decreasing the gastrointestinal pathogenic bacteria. The antimicrobial composition is administered to the alimentary tract.

Still further, the method comprises administering an antibiotic in combination with the antimicrobial composition. The antibiotic is selected from the group consisting of aminoglycoside, penicillin, cephalosporin, carbapenem, glycopeptide, rifamycin, quinolone, fusidic acid, sulfonamide, streptogramin, lipopeptide, tetracycline, macrolide, ketolide, chloramphenicol, oxazolidinone, lincosamindemetronidazole or ciprofloxacin.

The present invention also contemplates methods of detecting infections in the gastrointestinal system tract of a subject comprising (a) assessing a sample for abnormal amounts of Reg proteins; and (b) correlating the presence of abnormal amounts of Reg proteins with a gastrointestinal system infection. The Reg protein can be RegIII, more specifically, human hepatocarcinoma-intestine-pancreas/pancreatic-associated protein (HIP/PAP). Assessing may comprise detecting protein directly, such as with immunologic assays (e.g., ELISA, RIA, Western blot, etc.), or by examining expression of Reg-encoding transcription (e.g., RT-PCR). The method may also comprise the further step of making a treatment decision based on the result of the method, namely, to administer or not administer an anti-microbial therapy to said subject.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Expression of RegIIIγ (pET3a-RegIIIγ) was induced by the addition of 0.4 mM IPTG. HIP/PAP expression constructs (wild-type=pET3a-HIP/PAP; mutant=pET3a-HIP/PAPmut) were induced by the addition of 1 mM IPTG. Total *E. coli* lysates from pre- and post-induction cultures were analyzed by electrophoresis through a 15% SDS-PAGE gel followed by Coomassie Blue staining. (FIG. 1B) Predicted stem structure involving residues 12-19 of the HIP/PAP mRNA coding region. The stem was predicted by analyzing the mature HIP/PAP coding sequence using the web-based RNA secondary structure prediction algorithm. (FIG. 1C) Positions of the silent mutations incorporated into the forward primer used to generate pET3a-HIP/PAPmut. The residues corresponding to the predicted stem are indicated by a line.

(FIG. 8A) RegIIIγ mRNA expression in Paneth cells. Paneth cells were harvested by laser-capture microdissection from germ-free and conventionalized small intestines. Q-PCR analysis was performed on RNAs from microdissected Paneth cells from 3 mice per group. Values were normalized to GAPDH expression and mean±s.d. is plotted (range for conventionalized samples is 42-309). Results are expressed relative to one of the germ-free samples. GF=germ-free; Conv-D=conventionalized. (FIG. 8B) RegIIIγ protein expression in small intestine. RegIIIγ was detected in mid-small intestinal protein by immunoblot with anti-RegIIIγ antiserum (Cash et al., 2006). The lower band in the protein sample from conventionalized mice likely results from proteolytic cleavage at a trypsin-like site near the N-terminus (Cash et al., 2006), similar to that described for RegIα (Dieckgraefe et al., 2002). Results are representative of 2 independent experiments. rRegIIIγ=recombinant RegIIIγ. (FIG. 8C) RegIIIγ binds to intestinal bacteria. Flow cytometry reveals binding of AlexaFluor555-conjugated RegIIIγ to intestinal bacteria recovered from conventional mouse small intestine. BSA-AlexaFluor555 showed no binding (data not shown). Results are representative of independent experiments with 3 mice. (FIG. 8D) RegIIIγ binds preferentially to Gram-positive intestinal bacteria. Dual-color flow cytometry analysis with WGA-AlexaFluor488 and RegIIIγ-AlexaFluor555 shows preferential binding to the WGA-positive bacterial population. Results are representative of 3 independent experiments. (FIG. 8E) RegIIIγ binds preferentially to cultured Gram-positive bacteria. Formaldehyde-fixed preparations of Gram-positive (*Listeria innocua* and *Enterococcus faecalis*) and Gram-negative bacteria (*Salmonella typhimurium* and *Pseudomonas aeruginosa*) were incubated with RegIIIγ followed by detection with anti-RegIIIγ antiserum and goat anti-rabbit-Cy3, and analyzed by flow cytometry. Asterisks indicate statistically significant differences between Gram-positive species and *S. typhimurium* ($p<0.05$). Pre-immune serum controls are shown in FIG. 16.

(FIG. 11A) Peptidoglycan pull-down assays. 10 μg of RegIIIγ or HIP/PAP was added to 50 μg insoluble *Bacillus subtilis* peptidoglycan and pelleted. Pellet (P) and supernatant (S) fractions were analyzed by SDS-PAGE and Coomassie Blue staining. (FIG. 11B) Lectin binding to insoluble peptidoglycan is competed by soluble peptidoglycan. Pull-down assays were performed with or without 100 μM soluble *B. subtilis* peptidoglycan. (FIG. 11C) Comparison of peptidoglycan and chitin structures. The structure of a typical Gram-positive peptidoglycan is depicted. (FIG. 11D) Lectin binding to immobilized polysaccharides. Lectins were bound to immobilized mono- or polysaccharide for 2 hours at 4° C. After washing, bound proteins were released by boiling in SDS-PAGE sample buffer and analyzed by SDS-polyacrylamide gel electrophoresis and Coomassie blue staining. (FIG. 11E) Pull-down assays comparing binding to peptidoglycan, chitin, and cellulose. 10 μg of purified recombinant RegIIIγ or HIP/PAP were added to 50 μg of peptidoglycan, chitin, or cellulose and analyzed as in (FIG. 11A). The lower molecular weight forms of RegIIIγ and HIP/PAP in (FIG. 11A) and (FIG. 11E) result from cleavage at an N-terminal trypsin-like site by a peptidoglycan-associated proteolytic activity.

(FIG. 13A) Percentage of CFUs remaining after exposure to purified RegIIIγ and HIP/PAP. *Listeria innocua, Listeria monocytogenes, Enterococcus faecalis, Escherichia coli* K12, and *Bacteroides thetaiotaomicron* were grown to mid-log phase and incubated with purified lectins. Initial bacterial concentrations ranged from $10^5$ to $10^6$ CFU/ml. After incubation for 2 h at 37° C., viable bacteria were quantitated by dilution plating. Assays were done in triplicate. Mean±s.d. is plotted. (FIG. 13B) Transmission electron microscopy of *L. monocytogenes* following a 2 hour exposure to 10 μM purified recombinant RegIIIγ and HIP/PAP. Arrows indicate examples of damaged cell surfaces and cytoplasmic leakage. Bar=100 nm. (FIG. 13C) Lectin bactericidal activity is inhibited by chitooligosaccharides and soluble peptidoglycan (sPGN). 10 mM GlcNAc, chitobiose ($GlcNAc_2$), or chitotetraose ($GlcNAc_4$), or 35 μM sPGN were added to antibacterial assays performed on *L. innocua* as in (FIG. 13A). Each % CFU was calculated relative to a no-lectin control assay containing an identical amount of chitooligosaccharide or sPGN.

Figure 15:
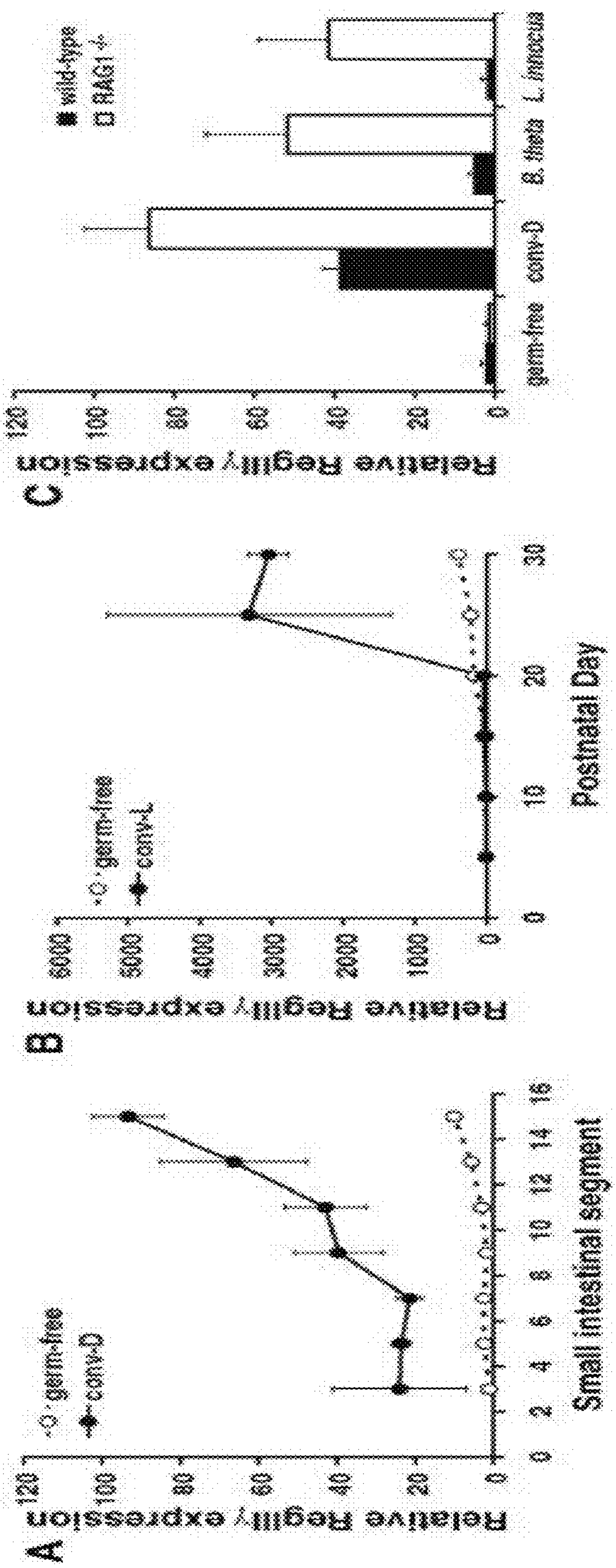

FIGS. 15A-15C show RegIIIγ expression is triggered by intestinal bacteria. (FIG. 15A) RegIIIγ expression along the cephalocaudal axis of the small intestine. Small intestines from adult germ-free or conventionalized (conv-D) NMRI mice were divided into 16 equal segments and RegIIIγ mRNA expression was determined in specific segments using Q-PCR. Results are representative of experiments in two sets of mice. (FIG. 15B) RegIIIγ mRNA increases during the weaning period (P17-22) in developing conventionally raised NMRI mice. Assays were performed on pooled mid-small intestinal RNAs (n=3 mice/time point). (FIG. 15C) RegIIIγ expression is triggered by single Gram-positive or Gram-negative bacterial species in immunodeficient mice. Q-PCR determinations were done on cDNAs from mid-small intestine.

Figure 16:
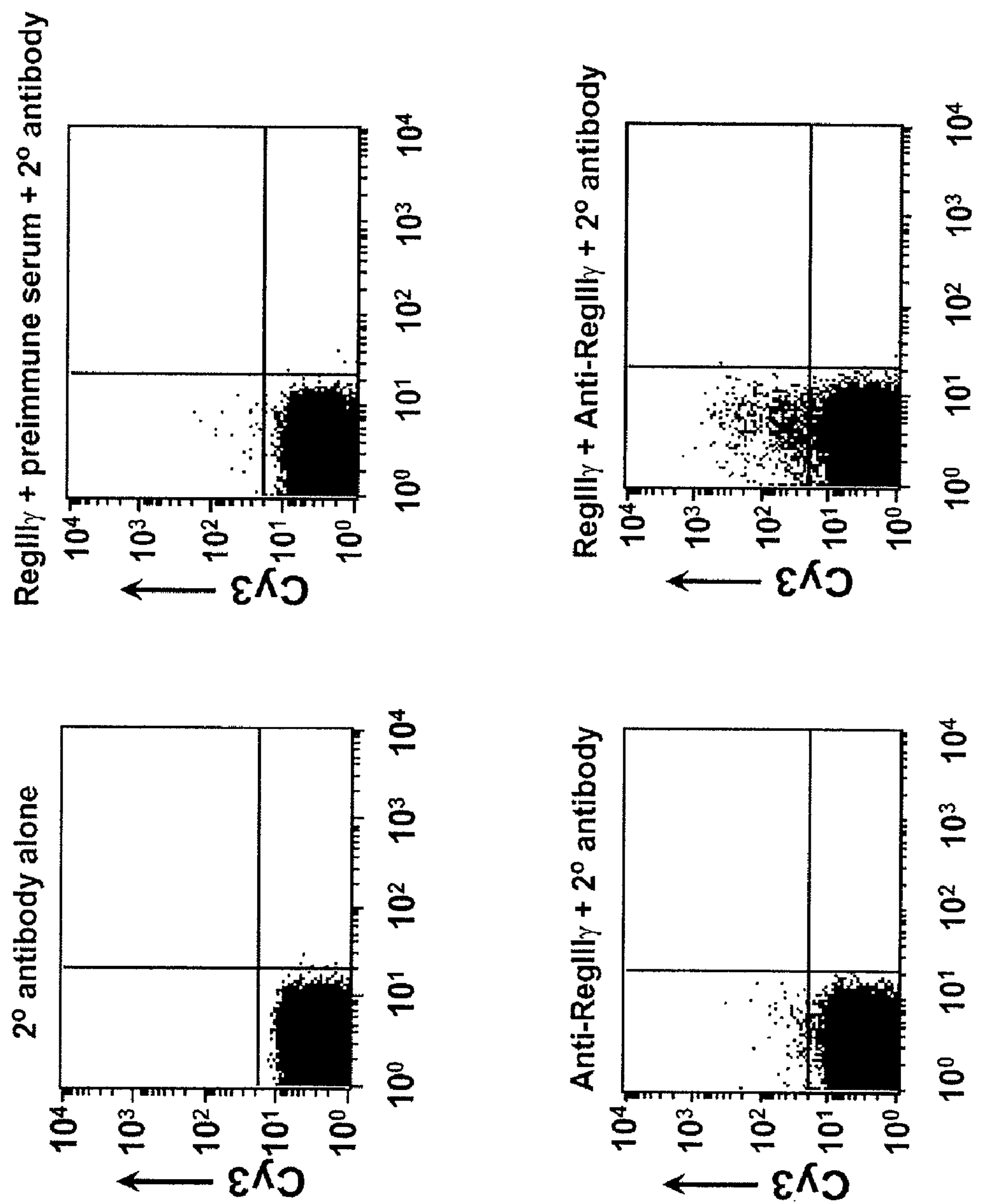

FIG. 16 shows flow cytometric analysis of RegIIIγ binding to cultured bacteria. Purified recombinant RegIIIγ was incubated with pure preparations of cultured *L. innocua, E. faecalis, S. typhimurium*, or *P. aeruginosa*. Each species was also incubated with secondary antibody alone, RegIIIγ pre-immune serum followed by secondary antibody (goat anti-rabbit-Cy3), or anti-RegIIIγ followed by secondary antibody. Shown are representative dot plots for *L. innocua.*

Figure 17:
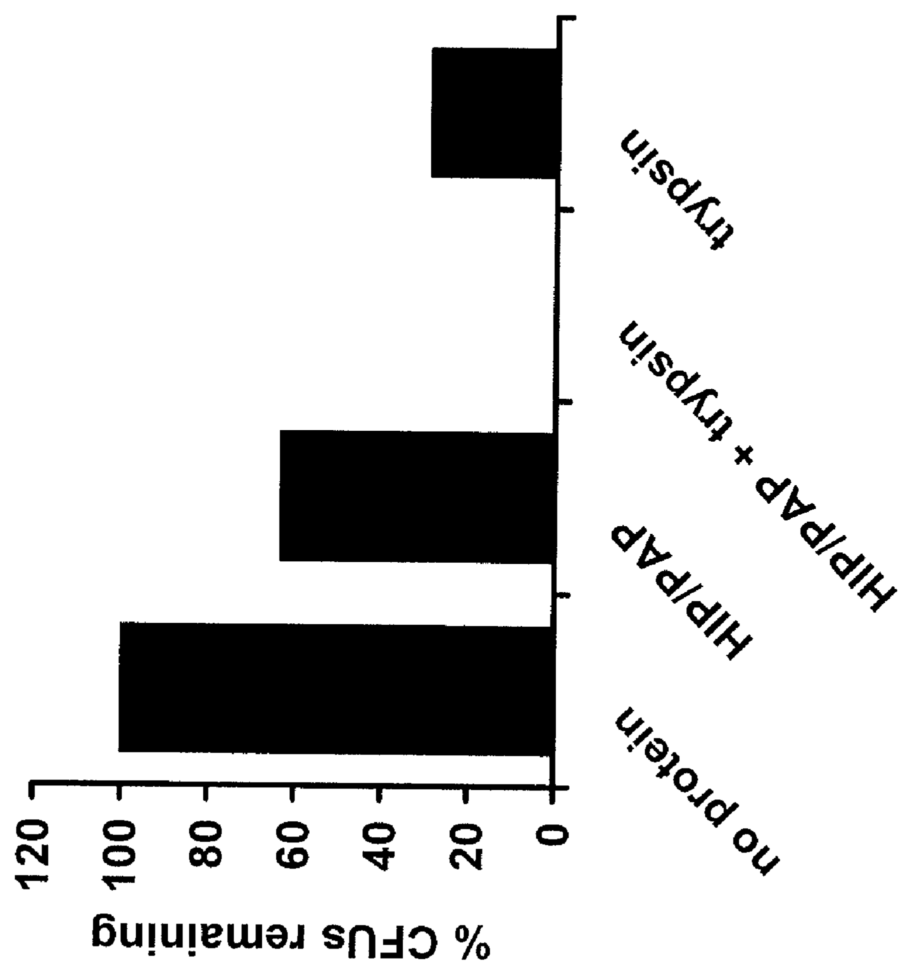

FIG. 17 shows the results from N-terminal truncation on bacterial activity. Eleven amino acids were truncated from the N-terminus HIP/PAP resulting in increase bactericidal activity.

FIGS. 18A-D show that Toll-like receptors govern RegIIIγ expression in small intestinal epithelia. (FIG. 18A) RegIIIγ expression in the small intestines of germ-free (gf) wild-type (wt) and conventionally raised (cv) mutant mice lacking key innate immune signaling adaptors (3-4 mice per group). QPCR results are shown as mean values normalized to 18S ribosomal RNA, and relative expression levels for each sample were calculated relative to a matched wild-type control sacrificed at the same time. (FIG. 18B) RegIIIγ expression in small intestinal epithelia of germ-free and conventionally-raised MyD88-deficient mice. Small intestinal sections were probed with anti-RegIIIγ antiserum (red) and counterstained with Hoescht dye (blue). (FIG. 18C), Q-PCR analysis of laser capture microdissected Paneth cells. Q-PCR assays were run in triplicate, normalized to 18S ribosomal RNA, and relative expression levels were calculated relative to germ-free (gf). (FIG. 18D) RegIIIγ expression in the small intestines of mice lacking specific Toll-like receptors (TLRs; n=3 mice per group). Q-PCR results were analyzed as in FIG. 18A. Error bars, ±SEM. , $P<0.01$; *, $P<0.001$ (compared with wt conventionally-raised).

FIGS. 19A-C show activation of RegIIIγ expression occurs via an epithelial cell-intrinsic mechanism. (FIG. 19A) RegIIIγ mRNA expression levels were quantitated in small intestinal tissues of wild-type (wt) or MyD88-deficient mice transplanted with bone marrow from wild-type donors. Q-PCR analyses were done as described in FIGS. 18A-D. (FIG. 19B) Immunohistochemistry of small intestinal tissues from bone marrow chimeras. (FIG. 19C), $IKKb_{\Delta IEC}$ or $IKKb_{F/F}$ littermate controls (n=3-4 mice per group) were analyzed for RegIIIγ expression by Q-PCR. Error bars, ±SEM. , $P<0.01$; *, $P<0.001$ (compared with $IKKb_{F/F}$).

FIGS. 20A-E shows that RegIIIγ expression is triggered by invasive bacteria. (FIG. 20A) RegIIIγ expression in wild-type and RAG1-deficient mice was quantitated by Q-PCR (n=3 mice per group). *B. theta* denotes ex-germ-free mice colonized with *B. thetaiotaomicron* for 10 days; cv=conventionally-raised mice. Values were normalized to 18S ribosomal RNA and are expressed relative to germ-free (gf). (FIG. 20B) *B. thetaiotaomicron* numbers in ex-germ-free wild-type and $RAG1_{-/-}$ small intestines. (FIG. 20C) *Salmonella typhimurium* numbers (wild-type and ASPI mutant) in ex-germ-free small intestines and spleen 48 hours after oral inoculation. (FIG. 20D) RegIIIγ expression in distal small intestines of mice colonized for 48 hours with wild-type or mutant *Salmonella*. Values were normalized to 18S ribosomal RNA and are expressed relative to germ-free values (gf). (FIG. 20E) RegIIIγ expression in small intestinal epithelia of mice colonized with wild-type or mutant *Salmonella*. Small intestinal sections were probed with anti-RegIIIγ antiserum (red) and counterstained with Hoescht dye (blue).

FIGS. 21A-C shows that Nod2-dependent anti-microbial responses constitute a generic response to bacterial colonization of the intestine. (FIG. 21A) Defer-rs10 expression in the small intestines of germ-free (gf) wild-type (wt) and conventionally-raised (cv) MyD88- and NOD2-deficient mice (n=3 per group). Q-PCR results are shown as mean values normalized to 18S ribosomal RNA, and relative expression levels for each sample were calculated relative to a matched wild-type control. Error bars, ±SEM. *, $P<0.001$ (compared with wt cony). (FIG. 21B) Q-PCR quantitation of Defer-rs-10 expression in wild-type and RAG1-deficient mice. Analyses were carried out as in FIG. 20**A. *, $P<0.05$; **, $P<0.01$ (compared with gf wt). *B. thetaiotaomicron* counts are the same as in FIG. 20B. (FIG. 21C) Defer-rs-10 expression in distal small intestines of mice colonized for 48 hours with wild-type or mutant *Salmonella*. Values were normalized to 18S ribosomal RNA and are expressed relative to germ-free values (gf). *, $P<0.05$ (compared with gf)

Figure 22:
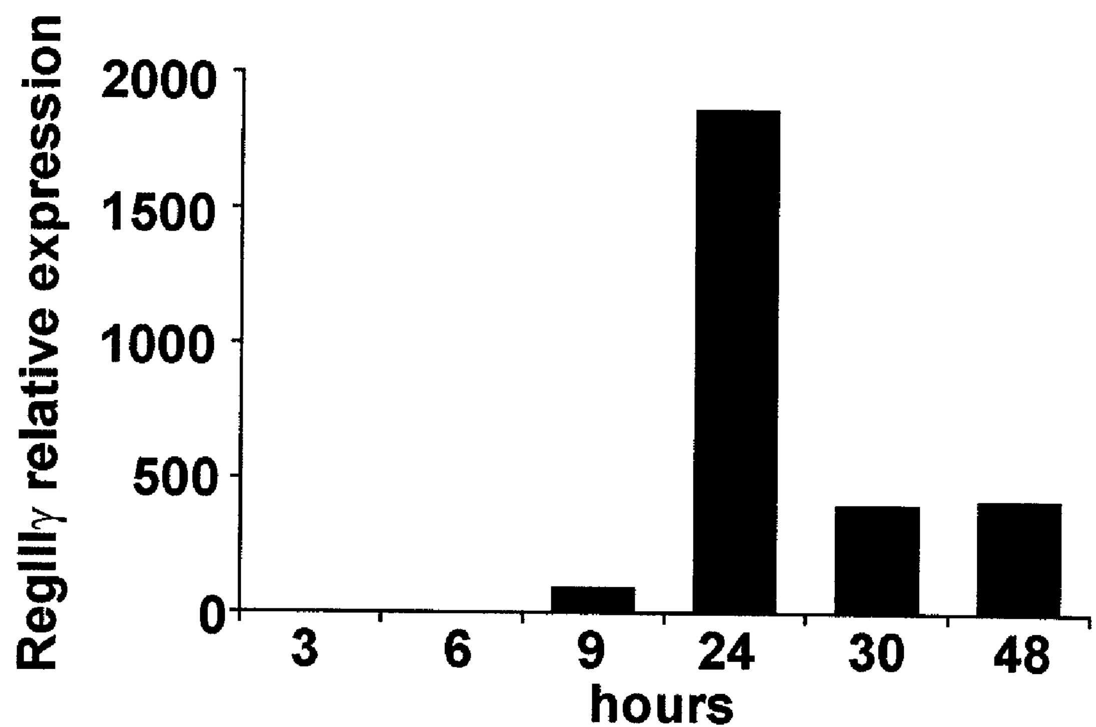

FIG. 22 shows time course of RegIIIγ expression following introduction of *Salmonella typhimurium* into germ-free mice. Q-PCR quantitation of RegIIIγ expression in distal small intestines of mice colonized for the indicated times with wild-type *Salmonella typhimurium.*

DETAILED DESCRIPTION OF THE INVENTION

I. Definitions

Unless defined otherwise, technical and scientific terms used herein have the same meaning as commonly understood by one of ordinary skill in the art to which this invention belongs. For purposes of the present invention, the following terms are defined below.

The term "antimicrobial" as used herein refers to an agent or composition of agents that inhibit the growth or multiplication or colonization of microorganisms or kills the microorganisms.

The term "antibiotics" as used herein is defined as a substance that inhibits the growth of microorganisms without damage to the host. For example, the antibiotic may inhibit cell wall synthesis, protein synthesis, nucleic acid synthesis, or alter cell membrane function. The classes of antibiotics used may fall under two categories, bactericidal and bacteriostatic. Bactericidal antibiotics include those from the group consisting of aminoglycosides, penicillins, cephalosporins, carbapenems, glycopeptides, rifamycins, quinolones, fusidic acid, sulfonamides, streptogramins, and lipopeptides. Bacteriostatic antibiotics include those from the group consisting of tetracyclines, macrolides, ketolides, chloramphenicols, oxazolidinones, and lincosamindes. In specific embodiments, bactericidal agents include, but are not limited to, kanamycin, gentamicin, tobramycin, netilmicin, sisomicin, amikacin, ampicillin, amoxicillin, cloxacillin, dicloxacillin, ticarcillin, indanyl carbenicillin, azlocillin, mezlocillin, nafcillin, oxacillin, piperacillin, cefazolin, cephalothin, cephapirin, cephradine, cefamandole, cefonicid, cefuroxime, cefmetazole, cefotetan, cefoxitin, cefotaxime, cefoperazone, ceftazidine, ceftizoxime, ceftriaxone, moxalactam, cefepime, cefpirome, cefadroxil, cephalexin, cephradine, cefaclor, cefprozil, cefuroxime, locracarbef, cefdinir, cefditoren, cefixime, cefpodoxime, ceftibuten, cefepelem, cephamasporin, ceftobiprole, aztreonam, imipenem, meropenem, ertapenem, vancomycin, teicoplanin, dalbavancin, telavancin, rifampin, rifabutin, nalidixic acid, fucidins, sulfamethoxazole, sulfadiazine, sulfisoxazole, sulphafurazole, sulfamethoxazole, sulfamethizole, sulfadimidine, sulfacarbamide, sulfadoxine, sulgaguanidine, sulfathalidine, sulfasalazinesulfamylon, mikamycin, virginiamycin, pristinamycin, quinupristin-dalfopristin and daptomycin.

The term "bactericidal" as used herein is defined as an antimicrobial agent that is known by those of skill in the art to kill organisms.

The term "bacteriostatic" as used herein is defined as an antimicrobial agent that is known by those of skill in the art to inhibit the growth of organisms.

The terms "cell," "cell line," and "cell culture" as used herein may be used interchangeably. All of these terms also include their progeny, which are any and all subsequent generations. It is understood that all progeny may not be identical due to deliberate or inadvertent mutations.

The term "cell wall" as used herein is defined as the peptidoglycan structure of eubacteria which gives shape and rigidity to the cell.

The term "effective concentration" means that a sufficient amount of the antimicrobial agent is added to decrease, prevent or inhibit the growth of bacterial organisms or bacterial colonization. The amount will vary for each compound and upon known factors such as pharmaceutical characteristics; the type of medical device; age, sex, health and weight of the recipient; and the use and length of use. It is within the skilled artisan's ability to relatively easily determine an effective concentration for each compound.

The term "gram-negative bacteria" or "gram-negative bacterium" as used herein is defined as bacteria which have been classified by the Gram stain as having a red stain. Gram-negative bacteria have thin walled cell membranes consisting of a single layer of peptidoglycan and an outer layer of lipopolysacchacide, lipoprotein, and phospholipid. Exemplary organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary Gram-negative organisms not in the family Enterobacteriacea include, but are not limited to, *Pseudomonas aeruginosa, Stenotrophomonas maltophilia, Burkholderia, Cepacia, Gardenerella, Vaginalis*, and *Acinetobacter* species.

The term "gram-positive bacteria" or "gram-positive bacterium" as used herein refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative staphylococci, streptococci, enterococci, *corynebacteria*, and *Bacillus* species.

The term "microbe(s)" or "microbial organism" as used herein is defined as a microscopic organism such as bacteria, fungi, microscopic algae, protozoa, and viruses unable to be seen by the naked eye.

The term "pathogenic bacteria" or "pathogenic bacterium" includes all known and unknown pathogenic bacterium (gram positive or gram negative) and any non-pathogenic bacteria that has been mutated or converted to a pathogenic bacterium that result in a disease and/or condition in a subject that is exposed to the pathogenic bacteria.

The term "peptidoglycan" as used herein is defined as a rigid mesh made up of ropelike linear polysaccharide chains cross-linked by peptides.

As used herein, the term "expression construct" or "transgene" is defined as any type of genetic construct containing a nucleic acid coding for gene products in which part or all of the nucleic acid encoding sequence is capable of being transcribed can be inserted into the vector. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene. One skilled in the art realizes that the present invention utilizes the expression construct or transgene as an antibacterial therapy. The expression construct or transgene may also be used as a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra. In the present invention, the term "therapeutic vector" may also be used to refer to the expression vector.

As used herein, the term "gene" is defined as a functional protein, polypeptide, or peptide-encoding unit. As will be understood by those in the art, this functional term includes genomic sequences, cDNA sequences, and smaller engineered gene segments that express, or is adapted to express, proteins, polypeptides, domains, peptides, fusion proteins, and mutants.

The term "inhibiting" or "reducing" as used herein, is taken to mean the act of limiting the growth of microbes or pathogenic bacteria.

II. The Present Invention

The present invention relates to antimicrobial compositions comprising Reg proteins, more specifically, mouse RegIIIγ, mouse RegIIIβ and human HIP/PAP, and the uses of these compositions to enhance innate immunity and/or reduce or inhibit bacterial colonization or growth or bacterial translocation or bacterial invasion of host tissues. In certain embodiments, the antimicrobial composition is bactericidal. The antimicrobial composition may also be bacteriostatic. Diagnostic applications for the identification of individuals with infections and gut disorders such as inflammatory bowel disease (IBD) also are envisioned.

The present invention also comprises a simple method for obtaining milligram quantities of RegIIIγ and HIP/PAP without the use of protein tags such as GST or Histidine. The method involves overexpressing the proteins in *E. coli*, isolating inclusion bodies, and refolding the proteins to their native conformations.

Still further, in order to improve HIP/PAP expression in bacterial expression systems, silent mutations are incorporated into the coding sequence to alleviate predicted RNA secondary structures at the ribosome binding site. Those of skill in the art recognize that silent mutations C→T, C→A, G→T or G→A within the coding region do not alter the specific amino acid sequence due to the degeneracy in the amino acid code. Silent mutations can be incorporated into the nucleic acid sequence using standard mutagenic procedures, such as site directed mutagenesis.

The inventors have also determined that the binding characteristics of RegIIIγ and HIP/PAP are similar to that of mannose binding lectin, which binds to mannose residues on bacterial surfaces and initiates recruitment of complement components that carry out microbial killing (Ezekowitz, 2003). However, there are two key differences between the Reg proteins and mannose binding lectin. First, although RegIIIγ and HIP/PAP both interact with mannan, they do not bind monomeric mannose, suggesting a requirement for a highly polymeric ligand. Second, whereas mannose binding lectin requires $Ca^{2+}$ for ligand binding (Weis et al., 1992), the binding of RegIIIγ and HIP/PAP to mannan is inhibited by $Ca^{2+}$.

Thus, RegIIIγ and HIP/PAP represent a new family of inducible antimicrobial proteins that seek out their microbial targets via interactions with bacterial peptidoglycan. Because they lack domains necessary for complement recruitment and are directly bactericidal, these proteins reveal a new function for mammalian C-type lectins. Thus, these antimicrobial proteins can be used to inhibit or reduce bacterial infections in various organs, such as the gastrointestinal system, integument system, pulmonary system, and circulatory systems. Yet further, the antimicrobial proteins can be used to treat bacterial infections and/or prevent bacterial infections in the oral cavity, bacteremia, sepsis, etc.

Yet further, the antimicrobial proteins of the present invention are used to enhance or upregulate the innate immunity of a subject. Thus, these proteins function in innate antimicrobial defense. Thus, these compositions can be used to treat inflammatory diseases, such as inflammatory bowel disease and/or inflammatory skin disorders or diseases.

III. Antimicrobial Compositions

In certain embodiments, a composition having antibacterial activity is administered to a subject to reduce or inhibit bacterial growth and/or colonization and/or reduce or inhibit bacterial activity. The composition of the present invention may be bactericidal.

The antimicrobial composition of the present invention may include, but is not limited to nucleic acid molecules (RNA or DNA), proteins, polypeptides, small molecules or other compositions that are capable of reducing and/or inhibiting bacterial growth and/or colonization. The antimicrobial composition may also comprise an expression vector. In certain embodiments, the antimicrobial composition may also comprise bacterial and/or probiotic compositions.

A. Proteins

The terms "RegIIIγ gene product," "RegIIIβ gene product," or "HIP/PAP gene product" refer to proteins and polypeptides having amino acid sequences that are substantially identical to the native RegIIIγ, RegIIIβ, HIP/PAP amino acid sequences (or RNA, if applicable) or that are biologically active, in that they are capable of performing functional activities similar to an endogenous RegIIIγ, RegIIIβ, HIP/PAP and/or cross-reacting with anti-RegIIIγ, anti-RegIIIβ, anti-HIP/PAP antibody raised against RegIIIγ, RegIIIβ, HIP/PAP, respectively.

The terms "RegIIIγ gene product," "RegIIIβ gene product," or "HIP/PAP gene product" also include related-compounds of the respective molecules that exhibit at least some biological activity in common with their native counterparts. Such related-compounds include, but are not limited to, truncated polypeptides and polypeptides having fewer amino acids than the native polypeptide. The RegIIIγ polypeptide sequences may include, but are not limited to the sequences available at Genbank UniGene Mm.252385. For example, the sequences can include, but are not limited to, SEQ ID NO:1 (Genbank accession no. 009049); SEQ ID NO:2 (Genbank accession no. AAH61139); SEQ ID NO:3 (Genbank accession no. BAA18930); SEQ ID NO:4 (Genbank accession no. NP_035390); and SEQ ID NO:5 (Genbank accession no. BAB25774). The RegIIIβ polypeptide sequences may include, but are not limited to sequences available at Genbank UniGene Mm.2553. For example, the sequences can include, but are not limited to SEQ ID NO:6 (Genbank accession no. BAA02727); SEQ ID NO:7 (Genbank accession no. BAA18928); SEQ ID NO:8 (Genbank accession no. NP_035166); and SEQ ID NO:9 (Genbank accession no. AAH27525). The HIP/PAP polypeptide sequences may include, but are not limited sequences available at Genbank UniGene Hs.567312. For example, the sequences include, but are not limited to SEQ ID NO:10 (Genbank accession no. AAA36415); SEQ ID NO:11 (Genbank accession no. NP_002571); SEQ ID NO:12 (Genbank accession no. AAT11161); SEQ ID NO:13 (Genbank accession no. AAT11159); SEQ ID NO:14 (Genbank accession no. NP_620355); SEQ ID NO:15 (Genbank accession no. CAA48605); SEQ ID NO:16 (Genbank accession no. AAB24642); SEQ ID NO:17 (Genbank accession no. BAA02728); and SEQ ID NO:18 (Genbank accession no. AAH36776).

As modifications and/or changes may be made in the structure of the polynucleotides and/or proteins according to the present invention, while obtaining molecules having similar or improved characteristics, such biologically functional equivalents are also encompassed within the present invention.

In particular embodiments of the present invention, the proteins or polypeptides are truncated versions of the native sequences. These N-terminal truncated proteins exhibit an increase in antibacterial activity compared to their native sequences. N-terminal variants include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal variants comprise at least deletions or truncations and/or substitutions of 1 to 16 N-terminal amino acid residues, more preferably, 11 N-terminal amino acid residues. The deletion and/or substitution of at least 11 N-terminal amino acid residues mediates an increased antimicrobial activity. For example, a truncated variant can have at least 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold or 100-fold increase in bactericial and/or bacterostatic activity compared to the native sequence. For example, the truncated protein exhibits at least 50%, 60%, 70%, 80%, 90% or 100% reduction in bacterial colonization, bacterial translocation or invasion of bacteria into the host tissues as compared to the native sequences.

Examples of the truncated RegIIIγ polypeptide sequence includes, but is not limited to SEQ ID NO:19. The truncated RegIIIβ polypeptide sequence includes, but is not limited to SEQ ID NO:20. The truncated HIP/PAP polypeptide sequence includes, but is not limited to SEQ ID NO:21.

1. Modified Polynucleotides and Polypeptides

The biological functional equivalent may comprise a polynucleotide that has been engineered to contain distinct sequences while at the same time retaining the capacity to encode a standard protein having antibacterial activity similar to that of the truncated proteins described above. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide may be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted. Functional activity is bactericidal and/or bacterostatic activity. Thus, the function equivalent is a protein that is capable of inhibiting and/or reducing bacterial colonization and/or bacterial growth and/or bacterial translocation and/or bacterial invasion into host tissues.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

2. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table of exemplary, but not limiting, modified and/or unusual amino acids is provided herein below in Table 1.

TABLE 1

Modified and/or Unusual Amino Acids

| Abbr. | Amino Acid |
|---|---|
| Aad | 2-Aminoadipic acid |
| BAad | 3- Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |

TABLE 1-continued

| Modified and/or Unusual Amino Acids | |
|---|---|
| Abbr. | Amino Acid |
| Nva | Norvaline |
| Nle | Norleucine |
| Orn | Ornithine |

3. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. These structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

4. Purification of Proteins

In certain embodiments, the Reg proteins are expressed using bacterial expression systems and are purified using standard techniques. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

B. Nucleic Acid Sequences

The term "RegIIIγ gene,", "RegIIIγ polynucleotide," "RegIIIγ nucleic acid," "RegIIIβ gene," "RegIIIβ polynucleotide," "RegIIIβ nucleic acid," "HIP/PAP gene," "HIP/PAP polynucleotide" or "HIP/PAP nucleic acid" refers to at least one molecule or strand of DNA (e.g., genomic DNA, cDNA) or RNA sequence, a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g., A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. An "isolated nucleic acid" as contemplated in the present invention may comprise transcribed nucleic acid(s), regulatory sequences, coding sequences, or the like, isolated substantially away from other such sequences, such as other naturally occurring nucleic acid molecules, regulatory sequences, polypeptide or peptide encoding sequences, etc.

More particularly, a "RegIIIγ gene,", "RegIIIγ polynucleotide," "RegIIIγ nucleic acid," "RegIIIβ gene," "RegIIIβ polynucleotide," "RegIIIβ nucleic acid," "HIP/PAP gene," "HIP/PAP polynucleotide" or "HIP/PAP nucleic acid" may also comprise any combination of associated control sequences. The RegIIIγ nucleic acid sequences include sequences available at Genbank UniGene Mm.252385. More specifically, the sequences may include, but are not limited to SEQ ID NO:22 (Genbank accession no. BC046602); SEQ ID NO:23 (Genbank accession no. BC061139); SEQ ID NO:24 (Genbank accession no. D63361); SEQ ID NO:25 (Genbank accession no. NM_011260); SEQ ID NO:26 (Genbank accession no. AK008608); and SEQ ID NO:27 (Genbank accession no. AK008446). The RegIIIβ nucleic acid sequences may include, but are not limited to sequences available at Genbank UniGene Mm.2553. For example, the sequences can include, but are not limited to SEQ ID NO:28 (Genbank accession no. D13509); SEQ ID NO:29 (Genbank accession no. D63359); SEQ ID NO:30 (Genbank accession no. NM_011036); and SEQ ID NO:31 (Genbank accession no. BC027525). The HIP/PAP nucleic acid sequences may include, but are not limited to sequences available at Genbank UniGene Hs.567312. For example, the sequences can include, but are not limited to SEQ ID NO:32 (Genbank accession no. M84337); SEQ ID NO:33 (Genbank accession no. NM_002580); SEQ ID NO:34 (Genbank accession no. AY544130); SEQ ID NO:35 (Genbank accession no. AY544128); SEQ ID NO:36 (Genbank accession no. DQ893897); SEQ ID NO:37 (Genbank accession no. NM_138938); SEQ ID NO:38 (Genbank accession no. NM_138937); SEQ ID NO:39 (Genbank accession no. X68641); SEQ ID NO:40 (Genbank accession no. S51768);

SEQ ID NO:41 (Genbank accession no. D13510); and SEQ ID NO:42 (Genbank accession no. BC036776). Thus, nucleic acid molecules encoding RegIIIγ, RegIIIβ, and/or HIP/PAP are herein provided and are also available to a skilled artisan at accessible databases, including the National Center for Biotechnology Information's GenBank database and/or commercially available databases, such as from Celera Genomics, Inc. (Rockville, Md.).

Yet further, nucleic acid sequences of the present invention can relate to the truncated proteins having increased antibacterial activity compared to the native sequences. In this respect, the corresponding nucleic acid sequences for the truncated RegIIIγ protein include, but are not limited to SEQ ID NO:43. The corresponding nucleic acid sequences for the truncated HIP/PAP include, but are not limited to SEQ ID NO:44.

It also is contemplated that a given protein from a given species may be represented by variants that have slightly different nucleic acid sequences but, nonetheless, encode the same protein (see Table 2 below).

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Such variants can include those sequences containing silent mutations, for example, but not limited to SEQ ID NO:43, SEQ ID NO:44 and SEQ ID NO:45. Silent mutations may be employed to alter the secondary RNA structure while retaining the primary RNA structure. Such alteration of the secondary RNA structure can increase the expression of these proteins in bacterial expression systems resulting in a simple and reliable method of producing large quantities of proteins. Those of skill in the art recognize that silent mutations C→T, C→A, G→T or G→A within the coding region of the protein does not alter the specific amino acid sequence. Silent mutations can be incorporated into the sequences utilizing standard mutagenesis procedures, such as site-directed mutagenesis, See U.S. Pat. Nos. 5,220,007; 5,284,760; 5,354,670; 5,366,878; 5,389,514; and 5,635,377 each incorporated herein by reference in its entirety.

Those of skill in the art realize that silent mutations can be incorporated into the sequences using standard techniques to relieve secondary RNA structures resulting in increased translation of the protein, such increases in protein translation can include, at least 5-fold, 10-fold, 20-fold, 30-fold, 40-fold, 50-fold, 60-fold, 70-fold, 80-fold, 90-fold or 100-fold increase in protein translation efficiency compared to the native sequences.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Still further, "RegIIIγ gene," "RegIIIγ polynucleotide," "RegIIIγ nucleic acid," "RegIIIβ gene," "RegIIIβ polynucleotide," "RegIIIβ nucleic acid," "HIP/PAP gene," "HIP/PAP polynucleotide" or "HIP/PAP nucleic acid" refer to nucleic acids provided herein, homologs thereof, and sequences having substantial similarity and function, respectively. The term "substantially identical", when used to define either RegIIIγ gene,""RegIIIγ polynucleotide," "RegIIIγ nucleic acid," "RegIIIβ gene," "RegIIIβ polynucleotide," "RegIIIβ nucleic acid," "HIP/PAP gene," "HIP/PAP polynucleotide" or "HIP/PAP nucleic acid", means that a particular subject sequence, for example, a mutant sequence, varies from the sequence of natural RegIIIγ, RegIIIβ and/or HIP/PAP, respectively, by one or more substitutions, deletions, or additions, the net effect of which is to retain at least some of the biological activity found in the native RegIIIγ, RegIIIβ and/or HIP/PAP protein, respectively. Alternatively, DNA analog sequences are "substantially identical" to specific DNA sequences disclosed herein if: (a) the DNA analog sequence is derived from coding regions of the natural RegIIIγ, RegIIIβ and/or HIP/PAP gene, respectively; or (b) the DNA analog sequence is capable of hybridization to DNA sequences of RegIIIγ, RegIIIβ and/or HIP/PAP under moderately stringent conditions and RegIIIγ, RegIIIβ and/or HIP/PAP, respectively having biological activity similar to the native proteins; or (c) DNA sequences which are degenerative as a result of the genetic code to the DNA analog sequences defined in (a) or (b). Substantially identical analog proteins will be greater than about 70%, greater than 75%, greater than 80%, greater than 85%, greater than 90%, greater than 95% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

In certain aspects of the present invention, DNA analog sequences are "substantially identical" to specific DNA sequences disclosed herein if: (a) the DNA analog sequence is derived from coding regions of the natural RegIIIγ, RegIIIβ and/or HIP/PAP gene, respectively; or (b) the DNA analog sequence is capable of hybridization to DNA sequences of RegIIIγ, RegIIIβ and/or HIP/PAP under moderately stringent conditions and RegIIIγ, RegIIIβ and/or HIP/PAP, respectively having biological activity similar to the native proteins; or (c) DNA sequences which are degenerative as a result of the genetic code to the DNA analog sequences defined in (a) or (b). Substantially identical analog proteins will be greater than about 70%, greater than 75%, greater than 80%, greater than 85%, greater than 90%, greater than 95% similar to the corresponding sequence of the native protein. Sequences having lesser degrees of similarity but comparable biological activity are considered to be equivalents. In determining polynucleotide sequences, all subject polynucleotide sequences capable of encoding substantially similar amino acid sequences are considered to be substantially similar to a reference polynucleotide sequence, regardless of differences in codon sequence.

As used herein, "hybridization," "hybridizes" or "capable of hybridizing" is understood to mean the forming of a double- or triple-stranded molecule or a molecule with partial double- or triple-stranded nature. The term "hybridization," "hybridize(s)" or "capable of hybridizing" relates to the terms "stringent condition(s)" or "high stringency" and the terms "low stringency" or "low stringency condition(s)" or "moderately stringent conditions."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium or moderate stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suite a particular application. For example, in other embodiments, hybridization may be achieved under conditions of, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

Naturally, the present invention also encompasses nucleic acid sequences that are complementary, or essentially complementary, to the sequences set forth herein, for example, in SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45. Nucleic acid sequences that are "complementary" are those that are capable of base-pairing according to the standard Watson-Crick complementarity rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein. Such sequences may encode an entire RegIIIγ, RegIIIβ and/or HIP/PAP molecule or functional or non-functional fragments thereof.

C. Expression Constructs

The present invention may involve using expression constructs as the pharmaceutical or antimicrobial composition and/or to produce large quantities of Reg proteins. In certain embodiments, it is contemplated that the expression construct comprises nucleic acid sequences encoding RegIIIγ, RegIIIβ and/or HIP/PAP polypeptides, as discussed above. Generally, such methods involve the generation of expression constructs containing, for example, a heterologous nucleic acid sequence encoding the protein of interest and a means for its expression, replicating the vector in an appropriate cell.

Yet further, in embodiments where the expression vectors are employed to produce large quantities of proteins, the expression construct comprising nucleic acid sequences encoding RegIIIγ, RegIIIβ and/or HIP/PAP polypeptides can be altered, as discussed above, by incorporating silent mutations into the coding region of the protein These mutations can relax or alter the secondary RNA structure without altering the protein resulting in an increase protein production. Those of skill in the art realize that silent mutations can be incorporated into the sequences using standard techniques to relieve secondary RNA structures resulting in increased translation of the protein, such increases in protein translation can include, at least 5-fold, 10-fold, 20-fold, 30-fold, 40-fold, 50-fold, 60-fold, 70-fold, 80-fold, 90-fold or 100-fold increase in protein translation efficiency compared to the native sequences.

Yet further, in certain embodiments, it is contemplated that nucleic acid or proteinaceous sequences may be co-expressed with other selected nucleic acid or proteinaceous sequences in the same host cell. Co-expression may be achieved by co-transfecting the host cell with two or more distinct recombinant vectors. Alternatively, a single recombinant vector may be constructed to include multiple distinct coding regions for nucleic acids, which could then be expressed in host cells transfected with the single vector.

1. Regulatory Sequences

As used in the present invention, the term "expression vector" refers to any type of genetic construct comprising a nucleic acid sequence coding for RegIIIγ, RegIIIβ and/or HIP/PAP polypeptides. In some cases, DNA molecules are then translated into a protein, polypeptide, or peptide. Expression vectors can contain a variety of "control sequences," which refer to nucleic acid sequences necessary for the transcription and possibly translation of an operably linked coding sequence in a particular host cell.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 by of DNA, and containing one or more recognition sites for transcriptional activator or repressor proteins. Other promoters that can be used, include IPTG-inducible promoter.

At least one module in each promoter functions to position the start site for RNA synthesis. The best known example of this is the TATA box, but in some promoters lacking a TATA box.

In the bacterial genome, there are several conserved features in a bacterial promoter: the start site or point, the 10-35 by sequence upstream of the start site, and the distance between the 10-35 by sequences upstream of the start site. The start point is usually (90% of the time) a purine. Upstream of the start site is a 6 by region that is recognizable in most promoters. The distance varies from 9-18 by upstream of the start site, however, the consensus sequence is TATAAT. Another conserved hexamer is centered at 35 by upstream of the start site. This consensus sequence is TTGACA. Additional promoter elements regulate the frequency of transcriptional initiation. The spacing between promoter elements frequently is flexible, so that promoter function is preserved when elements are inverted or moved relative to one another.

In certain embodiments, viral promoters may be used. These promoters may be extremely primitive or complex depending upon the virus. For example, some viral promoters like the T4 phage promoter may only contain an AT-rich sequence at 10 by upstream of the start site, but not a consensus sequence 35 by upstream of the start site.

In certain embodiments, the lac promoter, T7 promoter, T3, SP6, or tac promoter can be used to obtain high-level expression of the coding sequence of interest. The use of other bacterial, viral or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Also contemplated is the use of the native promoter to drive the expression of the nucleic acid sequence. Further, selection of a promoter that is regulated in response to specific physiologic signals can permit inducible expression of the gene product, e.g. heat shock promoters.

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

In addition to control sequences that govern transcription and translation, vectors and expression vectors may contain nucleic acid sequences that serve other functions as well and are described infra. It is contemplated in the present invention, that virtually any type of vector may be employed in any known or later discovered method to deliver nucleic acids encoding an RegIIIγ, RegIIIβ and/or HIP/PAP polypeptides. Where incorporation into an expression vector is desired, the nucleic acid encoding RegIIIγ, RegIIIβ and/or HIP/PAP polypeptides may also comprise a natural intron or an intron derived from another gene. Such vectors may be viral or non-viral vectors as described herein, and as known to those skilled in the art.

A gene therapy vector as described above can employ a transcription control sequence operably associated with the sequence for the RegIIIγ, RegIIIβ and/or HIP/PAP polypeptides inserted in the vector. Such an expression vector is particularly useful to regulate expression of a therapeutic RegIIIγ, RegIIIβ and/or HIP/PAP polypeptides.

2. Vectors

In particular embodiments of the invention, a plasmid vector is contemplated for use to transform a host cell. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, pWL-NEO, pSV2CAT, pOG44, PXT1, pSG (Stratagene) pSVK3, pBSK, pBR322, and pUC vectors.

Yet further, prokaryote-based systems can be employed for use with the present invention to produce nucleic acid sequences, or their cognate polypeptides, proteins and peptides. Many such systems are commercially and widely available. One skilled in the art is aware of the various prokaryote-based expression systems. Exemplary systems from PROMEGA include, but are not limited to, pGEMEX®-1 vector, pGEMX®-2 Vector, and Pinpoint control Vectors. Examples from STRATAGENE® include, but are not limited to, pBK Phagemid Vector, which is inducible by IPTG, pSPUTK In vitro Translation Vector, pET Expression systems, Epicurian Coli® BL21 Competent Cells and pDual™ Expression System.

3. Host Cells

As used herein, the terms “cell,” “cell line,” and “cell culture” may be used interchangeably. All of these terms also include their progeny, which is any and all subsequent generations formed by cell division. It is understood that all progeny may not be identical due to deliberate or inadvertent mutations. A host cell may be “transfected” or “transformed,” which refers to a process by which exogenous nucleic acid is transferred or introduced into the host cell. A transformed cell includes the primary subject cell and its progeny. As used herein, the terms “engineered” and “recombinant” cells or host cells are intended to refer to a cell into which an exogenous nucleic acid sequence, such as, for example, RegIIIγ, RegIIIβ and/or HIP/PAP nucleic acid molecules or a construct thereof. Therefore, recombinant cells are distinguishable from naturally occurring cells that do not contain a recombinantly introduced nucleic acid. In preferred embodiments of the present invention, the host cell is a prokaryotic cell, for example, *E. coli*. Yet further, other host cells that may be used can include, for example, insect cells.

4. Transfection/Transformation

In order to effect expression of constructs, the expression construct must be delivered into a cell. This delivery may be accomplished in vitro, as in laboratory procedures for transforming cells lines using well developed procedures. Transformation of bacterial cell lines can be achieved using a variety of techniques. One method includes using calcium chloride (Mandel and Higa, 1970). The exposure to the calcium ions renders the cells able to take up the DNA, or competent. Another method is electroporation. In this technique, a high-voltage electric field is applied briefly to cells, apparently producing transient holes in the cell membrane through which plasmid DNA enters (Shigekawa and Dower, 1988). These techniques and modifications are well known in the art. Thus, it is well within the scope of the present invention that a bacterial cell line may be transformed by any available transformation procedure or modification thereof. Another technique that can also be used for in vitro delivery of constructs is via lipofection.

Once the cell is transformed with the vector, the cells are cultured such that the cells multiply resulting in production of the desired protein. In certain embodiments, the cells that are transformed can be bacterial cells. Thus, a skilled artisan is cognizant that the development of microorganisms in culture media is dependent upon a number of very important factors, e.g., the proper nutrients must be available; oxygen or other gases must be available as required; a certain degree of moisture is necessary; the media must be of the proper reaction; proper temperature relations must prevail; the media must be sterile; and contamination must be prevented.

A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. Furthermore, different media results in different growth rates and different stationary phase densities. A rich media results in a short doubling time and higher cell density at a stationary phase. Minimal media results in slow growth and low final cell densities. Efficient agitation and aeration increases final cell densities. A skilled artisan will be able to determine which type of media is best suited to culture a specific type of microorganism. For example, since 1927, the DIFCO manual has been used in the art as a guide for culture media and nutritive agents for microbiology.

In addition to transformation of bacterial cell lines, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. The use of lipofection to introduce exogenous genes into the specific organs in vivo has certain practical advantages. Molecular targeting of liposomes to specific cells represents one area of benefit. Lipids may be chemically coupled to other molecules for the purpose of targeting. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (Wu and Wu, 1988).

IV. Pharmaceutical Preparations

Pharmaceutical compositions of the present invention comprise an effective amount of one or more antimicrobial compositions comprising RegIIIγ, RegIIIβ and/or HIP/PAP polypeptides or additional agent dissolved or dispersed in a pharmaceutically acceptable carrier. The phrases “pharmaceutical or pharmacologically acceptable” refers to molecular entities and compositions that do not produce an adverse, allergic or other untoward reaction when administered to an animal, such as, for example, a human, as appropriate. The preparation of a pharmaceutical composition that contains at least one RegIIIγ, RegIIIβ and/or HIP/PAP polypeptides or additional active ingredient will be known to those of skill in the art in light of the present disclosure, as exemplified by Remington’s Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The antimicrobial compositions comprising RegIIIγ, RegIIIβ and/or HIP/PAP polypeptides may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The antimicrobial compositions comprising RegIIIγ, RegIIIβ and/or HIP/PAP polypeptides may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include antimicrobial compositions comprising RegIIIγ, RegIIIβ and/or HIP/PAP polypeptides, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the antimicrobial compositions comprising RegIIIγ, RegIIIβ and/or HIP/PAP polypeptides may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Those of skill in the art are well aware of how to apply gene delivery to in vivo and ex vivo situations. For vectors, one generally will prepare a vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ particles to the patient. Similar figures may be extrapolated for liposomal or other formulations by comparing relative uptake efficiencies. Formulation as a pharmaceutically acceptable composition is discussed above.

A. Alimentary Compositions and Formulations

In preferred embodiments of the present invention, the antimicrobial compositions comprising RegIIIγ, RegIIIβ and/or HIP/PAP polypeptides are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, antimicrobial compositions comprising RegIIIγ, RegIIIβ and/or HIP/PAP polypeptides may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antimicrobial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound antimicrobial compositions comprising RegIIIγ, RegIIIβ and/or HIP/PAP polypeptides may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Therapeutic Applications

A. Infectious Disease

In certain embodiment of the invention, the compositions are useful for the treatment and/or prevention of infectious diseases and/or any inflammatory conditions that are caused by an infectious disease. Thus, these antimicrobial proteins can be used to inhibit or reduce bacterial infections in various organs, such as the gastrointestinal system, integument system, pulmonary system, and circulatory systems. Yet further, the antimicrobial proteins can be used to treat bacterial infections and/or prevent bacterial infections in the oral cavity, bacteremia, sepsis, etc. Infectious diseases can include those of a bacterial etiology such as bacterial meningitis, parameningeal infections, septic thrombophlebitis, pneumonia, tuberculosis, myocarditis, bacteremia, syphilis, etc.

Examples of infectious inflammatory conditions include but are not limited to pathogens such as meningococci, *Salmonella typhi, Yersinia enterocolitica* pathogens, etc.

The following bacteria are mention by way of example, including, but not limited to, serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans, peptostreptococci, other related species of streptococci, enterococci such as *Enterococcus faecalis, Enterococcus faecium*, staphylococci, such as *Staphylococcus epidermidis, Staphylococcus aureus*, particularly in the nasopharynx, *Hemophilus influenzae, Pseudomonas* species such as *Pseudomonas aeruginosa, Pseudomonas pseudomallei, Pseudomonas mallei, brucellas* such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species and related organisms. The invention may also be useful against Gram-negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species and the like.

In further embodiments, the composition can be administered to a subject suspected of or having bacteremia, sepsis, septic shock or sequelae. These conditions may be caused by gram-negative, gram-positive bacteria or other infectious agents such as *Candida* in any foci of the body and are at a risk of developing into or have developed into a systemic inflammatory response syndrome.

B. Inflammatory Disease

1. Inflammatory Bowel Disease

Yet further, the antimicrobial compositions of the present invention can be used to increase, enhance or upregulate the mucosal defense mechanism in a subject to help sequester the gut microflora and preserve intestinal homeostasis. Thus, enhanced expression of Reg proteins such as HIP/PAP in inflammatory bowel disease patients may limit mucosal penetration by gut microbes.

In certain embodiments, the present invention provides for both prophylactic and therapeutic methods of treating a subject at risk for, susceptible to or diagnosed with inflammatory bowel disease. Inflammatory bowel disease, or IBD, is a collective term encompassing related, but distinct, chronic inflammatory disorders of the gastrointestinal tract, such as Crohn's disease, ulcerative colitis (UC), indeterminate colitis, microscopic colitis and collagenous colitis, with Crohn's disease and ulcerative colitis being the most common diseases. Ulcerative colitis is confined to the large intestine (colon) and rectum, and involves only the inner lining of the intestinal wall. Crohn's disease may affect any section of the gastrointestinal tract (e.g., mouth, esophagus, stomach, small intestine, large intestine, rectum and anus) and may involve all layers of the intestinal wall. Both diseases, as well as other IBD, are characterized by abdominal pain and cramping, diarrhea, rectal and/or intestinal bleeding, weight loss and fever. The symptoms of these diseases are usually progressive, and sufferers typically experience periods of remission followed by severe flare-ups. Less frequent, but also possible, IBD symptoms reflect mucosal inflammation of other sections of the GI tract, such as duodenitis, jejunitis and proctitis.

Typically, diagnosis of IBD is based on the clinical symptoms, the use of a barium enema, and/or direct visualization (sigmoidoscopy or colonoscopy), with the latter being the most accurate test. For the diagnosis of Crohn's disease, see U.S. Pat. Nos. 6,348,452 and 6,297,015.

2. Inflammatory Skin Disorders

The antimicrobial compositions of the present invention can be used to treat inflammatory skin disorders. Inflammatory skin conditions are those conditions of the skin in which inflammatory cells (e.g., polymorphonuclear neutrophils and lymphocytes) infiltrate the skin with no overt or known infectious etiology. Symptoms of inflammatory skin conditions generally include erythema (redness), edema (swelling), pain, pruritus, increased surface temperature and loss of function. As used herein, inflammatory skin conditions include, but are not limited to, eczema and related conditions, insect bites, erythroderma, mycosis fungoides and related conditions, pyoderma gangrenosum, erythema multiforme, rosacea, onychomycosis, acne and related conditions, psoriasis and its related conditions, contact dermatitis, seborrheic dermatitis, folliculitis, perioral dermatitis, and impetigo.

C. Treatment Regimens

Treatment regimens may vary as well, and depend on the stage of bacterial infection and its consequences. The clinician will be best suited to make decisions on the best regimen to use based on the positive determination of the existing bacterial infection, the use of antibiotics and the known efficacy and toxicity (if any) of the therapeutic formulations.

The improvement is any observable or measurable improvement. Thus, one of skill in the art realizes that a treatment may improve the patient or subject's condition, but may not be a complete cure of the disease.

The antimicrobial composition of the present invention is utilized to markedly inhibit, reduce, prevent, abrogate, or minimize bacterial colonization, bacterial translocation and/or bacterial invasion into host tissues. Reduction, abrogation, minimization or prevention of microbial growth is achieved by using an effective concentration such that the concentration is effective to reduce the growth or colonization or translocation into host tissues or invasion into host of the microbes by at least 10%, 20%, 30%, 40%, 50%, 60%, 70%, 80%, 90%, 100% or any range therebetween.

In further embodiments, the antimicrobial composition of the present invention may reduce, inhibit, prevent, abrogate, or minimize inflammation. For example, an effective concentration reduces the amount of inflammation by at least 10%, 20%, 30%, 40%, 50%, 60%, 70%, 80%, 90%, 100% or any range therebetween. Yet further, the antimicrobial composition can result in a decrease in the production or activity of various inflammatory markers, for example, but not limited to IL-2, IL-4, IL-5, IL-6, IL-10, IL-11, and TNF-α. Yet further, the antimicrobial composition can reduce the amount or activation of neutrophils and/or Langerhans' cells.

D. Combination Treatments

In order to increase the effectiveness of the composition, it may be desirable to combine these compositions and methods of the invention with a known agent effective in the treatment or prevention of bacterial infections, infectious diseases and/or related inflammatory diseases and/or conditions, for example known agents to treat bacterial infections, e.g., antibiotics, and agents to treat inflammation. In some embodiments, it is contemplated that a conventional therapy or agent, including but not limited to, a pharmacological therapeutic agent may be combined with the composition of the present invention.

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination. In other aspects, one or more agents may be administered substantially simultaneously, or within about minutes to hours to days to weeks and any range derivable therein, prior to and/or after administering the composition.

Administration of the composition to a cell, tissue or organism may follow general protocols for the administration of antimicrobial therapeutics, taking into account the toxicity, if any. It is expected that the treatment cycles would be repeated as necessary. In particular embodiments, it is contemplated that various additional agents may be applied in any combination with the present invention.

Pharmacological therapeutic agents and methods of administration, dosages, etc. are well known to those of skill in the art (see for example, the "Physicians Desk Reference," Goodman & Gilman's "The Pharmacological Basis of Therapeuticsm" "Remington's Pharmaceutical Sciences," and "The Merck Index, Eleventh Edition" incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

1. Antimicrobial Agents

In certain embodiments, a second antimicrobial agent can be used in combination with the composition of the present invention. The second antimicrobial agent may comprise an antibiotic, anti-fungal, and anti-viral agent.

Antibiotics inhibits the growth of microorganisms without damage to the host. For example, the antibiotic may inhibit cell wall synthesis, protein synthesis, nucleic acid synthesis, or alter cell membrane function. Classes of antibiotics that can possibly be used in conjunction with the peptide include, but are not limited to, macrolides (i.e., erythromycin), penicillins (i.e., nafcillin), cephalosporins (i.e., cefazolin), carbepenems (i.e., imipenem, aztreonam), other beta-lactam antibiotics, beta-lactam inhibitors (i.e., sulbactam), oxalines (i.e., linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104 herein incorporated by reference will readily suggest themselves to those of ordinary skill in the art.

Anti-viral agents can also be used in combination the lactoferrin composition to treat and/or prevent a viral infection or disease. Such anti-viral agents include, but are not limited to protease inhibitors (e.g., saquinavir, ritonavir, amprenavir), reverse transcriptase inhibitors (e.g., azidothymidine (AZT), lamioridine (3TC), dideoxyinosine (ddI)), dideoxycytidine (ddC), zidovudine), nucleoside analogs (e.g., acyclovir, penciclovir).

In certain embodiments, anti-fungal agents can be used in combination with the peptide composition to treat and/or prevent a fungal infection. Such anti-fungal agents include, amphotericin B (Amphocin®, Fungizone®), butoconazole (Femstat®), clotrimazole (Mycelex®, Gyne-Lotrimin®, Lotrimin®, Lotrisone®), fluconazole (Diflucan®), flucytosine (Ancobon®), griseofulvin (Fulvicin P/G®, Grifulvin Gris-PEG®), itraconazole (Sporanox®), ketoconazole (Nizoral®), miconazole (Femizol-M®, Monistat®), nystatin (Mycostatin®), terbinafine (Lamisil®), terconazole (Terazol®), or tioconazole (Vagistat®).

2. Anti-Sepsis Agents

Anti-sepsis agents include, but are not limited to Drotrecogin alfa (activated). Agents used for the treatment of ALI and ARDS include but are not limited to intra-pulmonary instillation of surfactants, and leukotriene modifiers. Anti-inflammatory agents include, but are not limited to non-steroidal anti-inflammatory agents (e.g., naproxen, ibuprofen, celeoxib) and steroidal anti-inflammatory agents (e.g., glucocorticoids).

Non-limiting examples of non-pharmacologic interventions that may be used in the present invention include supportive care such as organ support in sepsis and septic shock and low tidal volume ventilation protocols in ALI and ARDS.

3. Anti-IBD Agents

Commonly known agents to treat IBD can be used in combination with the antimicrobial composition of the present invention. Non-limiting examples may include anti-inflammatory drugs, immunosuppressive drugs and surgery.

Anti-inflammatory drugs can include salicylates or corticosteroids. Preparations of salicylate are effective in treating mild to moderate disease and can also decrease the frequency of disease flares when the medications are taken on a prolonged basis. Examples of salicylates include sulfasalazine, olsalazine, and mesalamine.

Corticosteroids are more potent and faster-acting anti-inflammatory drugs in the treatment of IBD, as compared with salicylates. Prednisone, for example, is a corticosteroid commonly used in the treatment of severe cases of IBD.

Immune modulators can be used. For example, medications that suppress the immune system, namely immunosuprpressants, are used. Examples of immunosuppressants include azathioprine and 6-mercaptopurine. Immune modulatures such as anti-TNF agents or interleukin-11 may also be used to alter the immune system.

In addition to agents, surgery may also be used in combination with the antimicrobial composition. Typical surgical procedures include colectomy, proctocolectomy and ileostomy (See, Cecil Textbook of Medicine, 19th Edition, Wyngaarden et al., ed., 1992). These surgical treatments are radical procedures that often profoundly alter the everyday life of the patient.

In addition to the presently common methods of treating IBD described above, other methods of treating gastrointestinal disorders are disclosed in U.S. Pat. No. 5,110,795 (Hahn), U.S. Pat. No. 5,112,856 (Gaginella et al.), U.S. Pat. No. 5,216,002 (Gidda et al.), U.S. Pat. No. 5,238,931 (Yoshikawa et al.), U.S. Pat. No. 5,292,771 (Backstrom et al.), U.S. Pat. No. 5,312,818 (Rubin et al.), U.S. Pat. No. 5,324,738 (Dinan et al.), U.S. Pat. No. 5,331,013 (Ahlman et al.), U.S. Pat. No. 5,340,801 (Ewing et al.), U.S. Pat. No. 5,368,854 (Rennick), U.S. Pat. No. 5,391,555 (Marshall et al.), U.S. Pat. No. 5,552,439 (Panetta), U.S. Pat. No. 5,569,680 (Wu), U.S. Pat. No. 5,599,795 (McCann et al.), U.S. Pat. No. 5,604,231 (Smith et al.), U.S. Pat. No. 5,691,343 (Sandborn) and U.S. Pat. No. 5,693,645 (Sharpe et al.).

VI. Diagnostic Applications

In another aspect, the present invention contemplates detecting the presence of a Reg protein as diagnostic of microbial infection or a gut disorder such as IBD. As discussed further in the Examples, the inventors have correlated increased levels of Reg proteins in the gut of subjects infected with pathogenic microbes. It is envisioned that diagnostic methods will utilize gut tissue samples, such as those obtained in routein biopsy procedures, or may utilize serum which will contain Reg proteins produced in the gut but that make their way into the circulatory system.

A. Preparation of Antibodies Reactive with Reg Protein

An antibody can be a polyclonal or a monoclonal antibody. In a preferred embodiment, an antibody is a monoclonal antibody. Means for preparing and characterizing antibodies are well known in the art (see, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant B. Diagnostic Methods.

Antibodies of the present invention can be used in characterizing the Reg content of healthy and diseased tissues, through techniques such as ELISAs and Western blotting. This may provide a screen for the presence or absence of microbial infection.

The use of antibodies of the present invention, in an ELISA assay is contemplated. For example, anti-Reg antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Reg proteins that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label.

Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention may also be used in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Expression of Recombinant Mouse RegIIIγ and Human HIP/PAP in *E. coli*

A. Materials and Methods

Vectors, strains, and supplies. The expression vector pET3a was from Novagen. *E. coli* BL21-CodonPlus (DE3)-RIL and *E. coli* BL21-CodonPlus (DE3)-RILP competent cells were from Stratagene. Oligonucleotides and restriction enzymes were supplied by Invitrogen. Other DNA modifying enzymes and isopropyl-β-D-thiogalactopyranoside (IPTG) were from Roche Molecular Biochemicals. Luria Broth was purchased from VWR. Sephacryl S-100 high resolution gel filtration medium and size exclusion chromatography standards were from GE Healthcare. All other chemicals and reagents were from Sigma.

Construction of the mouse RegIIIγ expression vector. A 474 by amplicon was generated by RT-PCR from mouse small intestinal RNA using the specific primers SEQ ID NO:46: 5'-ATTGCGAGG CATATGGAAGTTGCCAAGAAAGATGCCCCAT-3' (forward primer) and SEQ ID NO:47: 5'-CTATGG GGATCCCTAGGCCTTGAATTTGCAGACATAGGGT-3' (reverse primer). The forward primer contained an NdeI restriction site (underlined) for cloning into pET3a. The reverse primer incorporated the native stop codon followed by an engineered BamHI site (underlined). The resulting amplicon contained a methionine start codon in place of the signal sequence, and thus encoded the mature secreted protein. PCR products and vector were digested with NdeI and BamHI, gel-purified, and ligated. The recombinant plasmid (pET3a-RegIIIγ) was sequenced to confirm the absence of mutations, and was transformed into *E. coli* BL21-CodonPlus (DE3)-RIL for protein expression.

Construction of HIP/PAP expression strains. A 474 by amplicon was generated by RT-PCR from human small intestinal RNA (Ambion) using the specific primers SEQ ID NO:48: 5'-ATTGCGAGG CATATGGAAGAACCCCAGAGAGGAACTGC-3' (forward primer) and SEQ ID NO:49: 5'-CTATGG TGATCACTAGTCAGTGAACTTGCAGACATA GGGTA A-3' (reverse primer). The forward primer contained an NdeI restriction site (underlined) for cloning into pET3a. The reverse primer incorporated the native stop codon followed by an engineered BclI site (underlined). The resulting amplicon lacked the HIP/PAP signal sequence and thus encoded the mature secreted protein (Christa et al., 2000). The PCR product was digested with NdeI and BclI, ligated into NdeI/BamHI-digested pET3a, and the resulting plasmid (pET3a-HIP/PAP) sequenced to confirm the absence of mutations.

Figure 4:
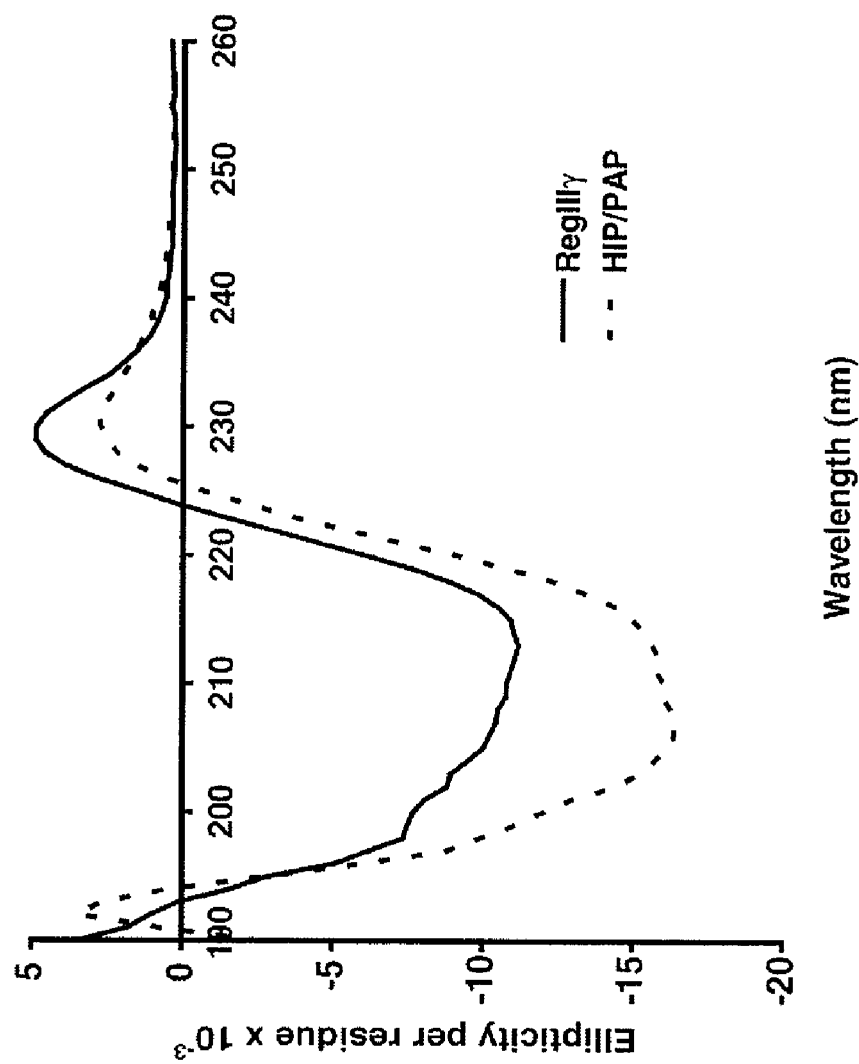
FIG. 4 shows circular dichroism spectra of RegIIIγ and HIP/PAP. Results show that RegIIIγ and HIP/PAP are composed predominantly of β-sheet structure, which is consistent with correct refolding.

A second expression construct (pET3a-HIP/PAPmut) was generated with silent mutations engineered into the 5' end of the HIP/PAP coding sequence. Mutations were introduced by redesigning the forward primer that was used to generate the wild-type HIP/PAP construct: SEQ ID NO:50: 5'-ATTGCGAGGCATATGGAAGAACCACAAAGAGAAACTGC-3' (mutant bases are underlined; also see FIG. 4C). A 474 by amplicon was generated by PCR with this mutant primer and the HIP/PAP-specific reverse primer above, using pET3a-HIP/PAP as template. The amplicon was cloned into pET3a as described for pET3a-HIP/PAP. The resulting plasmid was sequenced to confirm incorporation of the silent mutations and the absence of additional mutations. Both pET3a-HIP/PAP and pET3a-HIP/PAPmut were transformed into *E. coli* BL21-CodonPlus (DE3)-RILP for protein expression.

Expression and purification of RegIIIγ. *E. coli* BL21-CodonPlus (DE3)-RIL harboring pET3a-RegIIIγ were grown at 37° C. in 500 ml of LB medium supplemented with 0.1 mg/ml ampicillin to an absorbance of 0.6-1.0 (mid-log phase) at 600 nm. Protein expression was induced by the addition of 0.4 mM IPTG, and the culture was incubated for another 3 hours at 37° C. with good aeration. Cells were collected by centrifugation at 6,500 g for 15 minutes at 4° C., and the pellet resuspended in 1/20 culture volume (25 ml) of Inclusion Body (IB) Wash Buffer (20 mM Tris-HCl, 10 mM EDTA, 1% Triton X-100, pH 7.5). The cells were divided into five equal 5 ml aliquots and ruptured by sonication in two 1 minute bursts at setting 4 using a Misonix XL-2020 Sonicator fitted with a 4.8 mm tapered probe. The lysate was centrifuged at 10,000 g for 10 minutes, and the insoluble fraction was resuspended in 50 ml of IB Wash Buffer using a Dounce homogenizer. Centrifugation and resuspension were repeated, and the final insoluble inclusion body preparation was collected by centrifugation at 10,000 g for 10 minutes followed by dispersion in 10 ml of Resuspension Buffer (7M guanidine-HCl, 0.15M reduced glutathione, 0.1M Tris-HCl, 2 mM EDTA, pH 8.0) and rotation for 2 hours at room temperature. The resuspended inclusion bodies were added dropwise to a total of 500 ml of RegIIIγ Refolding Buffer (0.5M arginine-HCl, 0.6 mM oxidized glutathione, 50 mM Tris-HCl, pH 8.0) and left to stand for 24 hours. The solution was clarified by centrifugation at 10,000 g for 30 minutes, dialyzed overnight against 10 volumes of Dialysis Buffer 1 (25 mM Tris-HCl, 25 mM NaCl, 2 mM $CaCl_2$, pH 7), followed by a second overnight dialysis against 10 volumes of Dialysis Buffer 2 (25 mM MES, 25 mM NaCl, 2 mM $CaCl_2$, pH 6). The dialysate was centrifuged at 10,000 g for 30 minutes, and RegIIIγ was captured by passage over a 5 ml column of SP-Sepharose Fast Flow cation exchange resin (Sigma) equilibrated in Dialysis Buffer 2. After washing in 10 column volumes of Dialysis Buffer 2, the protein was batch-eluted in 5 column volumes of 0.4 M NaCl in Dialysis Buffer 2. Fractions containing protein were identified by the Bradford method (Bradford, 1976) using the Bio-Rad Protein Assay Dye Reagent Concentrate (Bio-Rad).

Expression and purification of HIP/PAP. Recombinant HIP/PAP was expressed from pET3a-HIP/PAPmut. The expression and purification protocol was similar to that of RegIIIγ, with some significant changes. First, the IPTG concentration used for protein induction was 1 mM, and induction proceeded for 2 hours. HIP/PAP-containing inclusion bodies were refolded in HIP/PAP Refolding Buffer (50 mM Tris-HCl pH 8.0, 10 mM KCl, 240 mM NaCl, 2 mM $MgCl_2$, 2 mM $CaCl_2$, 0.5M guanidine-HCl, 400 mM sucrose, 500 mM arginine-HCl, 1 mM reduced glutathione, 0.1 mM oxidized glutathione). Subsequent dialysis and ion-exchange chromatography steps were performed as described for RegIIIγ, except the SP-Sepharose column was batch-eluted in 0.6 M NaCl in Dialysis Buffer 2.

B. Results

Figure 1:
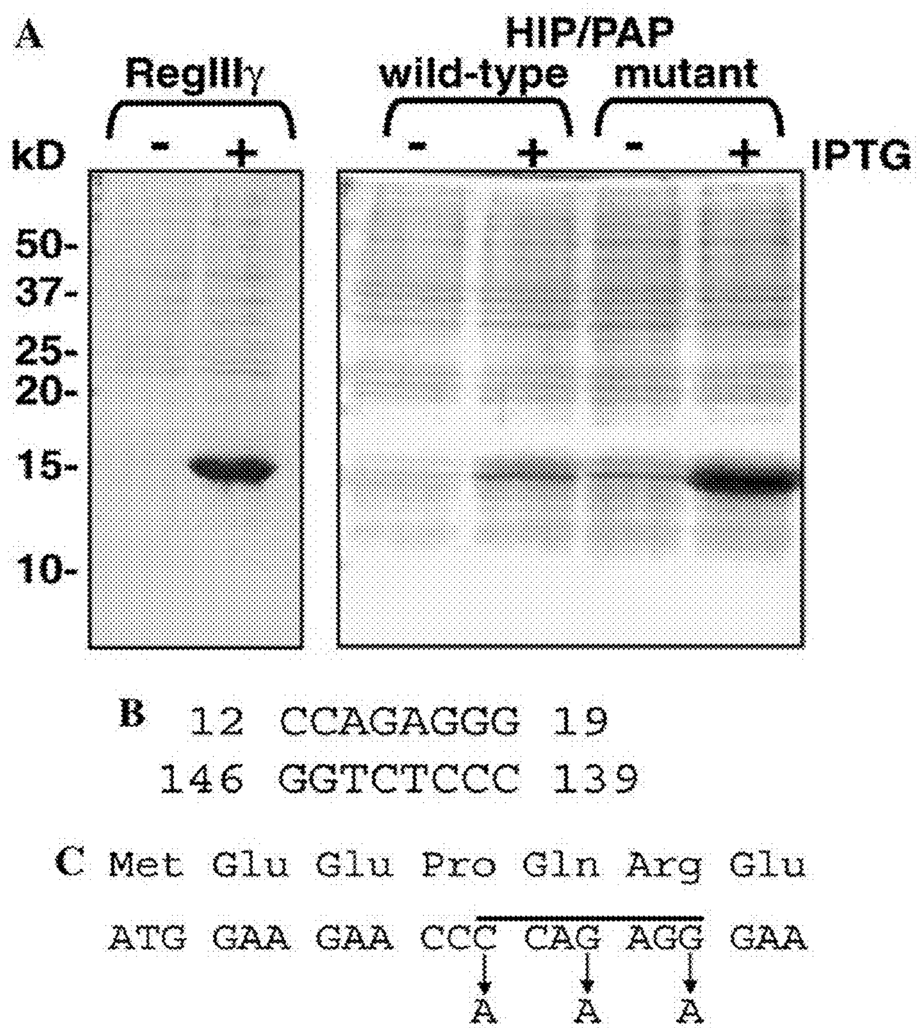
FIGS. 1A-1C show Expression of mouse RegIIIγ and human HIP/PAP in *Escherichia coli*.

Expression of recombinant mouse RegIIIγ and human HIP/PAP in *E. coli*. The open reading frame corresponding to mature mouse RegIIIγ (lacking the N-terminal signal peptide) was ligated into the bacterial expression vector pET3a to yield pET3a-RegIIIγ. To assess protein expression levels, IPTG was added to log-phase cultures, and pre- and post-induction cell lysates were analyzed by SDS-PAGE. Coomassie blue staining of gels revealed robust induction of RegIIIγ expression (FIG. 1A).

The mature human HIP/PAP open reading frame was also cloned into pET3a to yield pET3a-HIP/PAP. However, very little HIP/PAP expression was detected following the addition of IPTG to growing cultures (FIG. 1A). These results were consistent with those of other investigators who have expressed HIP/PAP in *E. coli* (Christa et al., 1996). Attempts to improve protein levels by altering induction conditions (IPTG concentration, induction time, induction temperature) were unsuccessful.

The inventors hypothesized that translation initiation from the pET3a-HIP/PAP construct might be impaired, resulting in poor induction of recombinant HIP/PAP expression. Analysis of the mature HIP/PAP coding sequence (including the engineered start codon), using a RNA secondary structure prediction algorithm, revealed the presence of a predicted stem involving nucleotides 12-19, with a free energy of −17.5 kcal/mol (FIG. 1B). By comparison, the mature RegIIIγ coding sequence contained a predicted stem encompassing nucleotides 8-11. This stem had a free energy of −7.1 kcal/mol, indicating a much less stable structure. Based on this analysis, the inventors reasoned that the presence of a stable stem close to the 5' end of the HIP/PAP mRNA could interfere with ribosome binding and subsequent translation. To test this idea, the inventors engineered 3 silent mutations into the forward primer used to amplify the HIP/PAP coding sequence (FIG. 1C), and cloned the resulting amplicon into pET3a to generate pET3a-HIP/PAPmut. The mutations were designed to abolish the predicted stem by substituting A for G or C, thus reducing the stability of the base pair interactions. Indeed, re-analysis of the altered sequence via the web-based algorithm confirmed the absence of the predicted stem. Consistent with this, the mutant HIP/PAP construct resulted in a remarkable increase in protein expression relative to the wild-type construct (FIG. 1A). Thus, all further HIP/PAP expression/purification studies were done using recombinant protein derived from pET3a-HIP/PAPmut.

Figure 2:
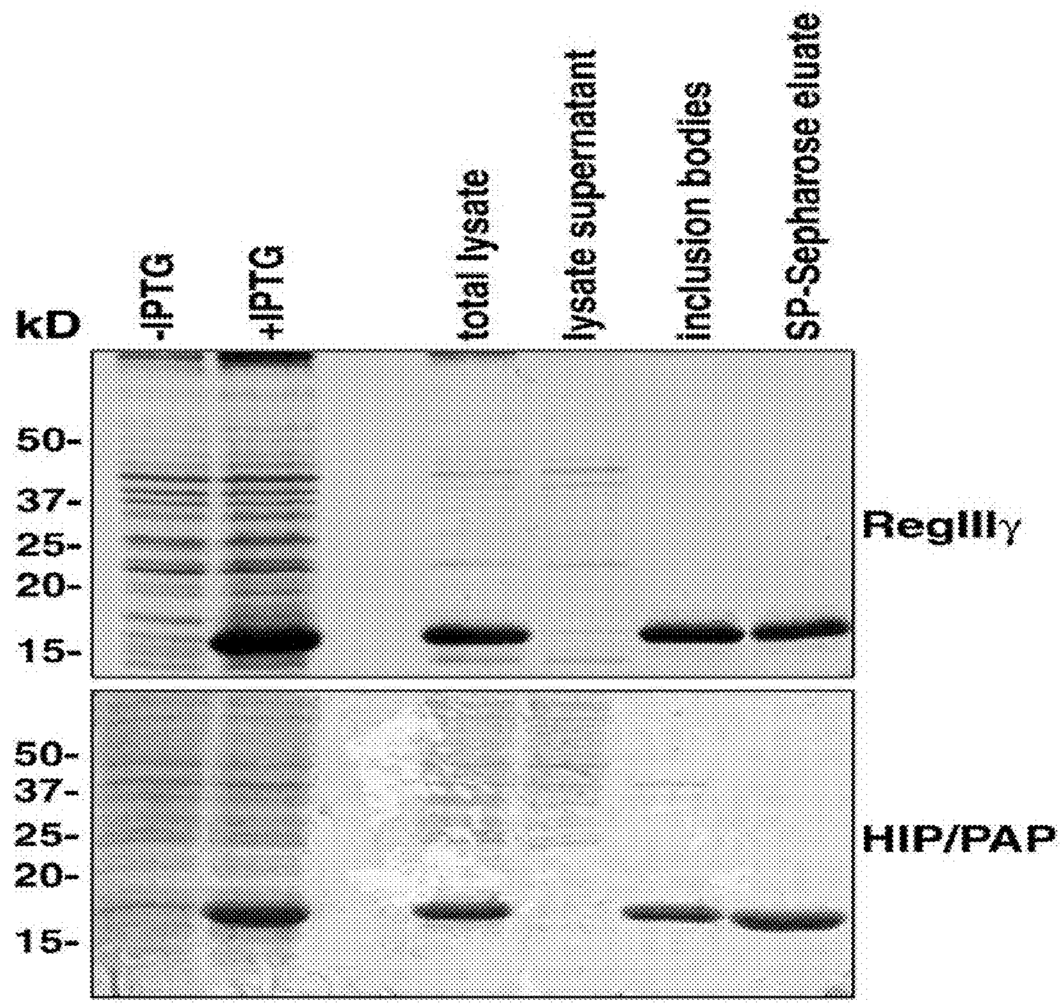
FIG. 2 shows SDS-PAGE analysis of samples taken during the purification of RegIIIγ and HIP/PAP. *E. coli* cells overexpressing recombinant RegIIIγ or HIP/PAP were collected before and after induction with IPTG (+ and −IPTG). The lanes containing total lysate and lysate supernatant samples were loaded with 10 μg total protein. Inclusion body and SP-Sepharose column eluate sample lanes contain 5 μg of protein. Proteins were resolved on a 15% polyacrylamide gel and stained with Coomassie brilliant blue.

Purification of mouse RegIIIγ and human HIP/PAP. *E. coli* BL21 expression strains such as BL21-CodonPlus (DE3)-RIL and BL21-CodonPlus (DE3)-RILP lack the ability to generate disulfide bonds between cysteine residues in proteins. As RegIIIγ and HIP/PAP both contain three predicted disulfide bonds, the inventors expected that the recombinant proteins would be misfolded and targeted to bacterial inclusion bodies. As shown in FIG. 2, both proteins were absent from the soluble fraction of *E. coli* lysates and were found in purified inclusion bodies. In both cases, recombinant protein represented the vast majority of inclusion body protein.

RegIIIγ and HIP/PAP from isolated inclusion bodies could be solubilized in 7 M guanidine hydrochloride under reducing conditions. However, both proteins required refolding and reoxidation prior to purification. In the case of RegIIIγ, the inventors refolded the protein using an approach similar to that used previously to obtain native Angiogenin-4 (Holloway et al., 2001). This procedure involved the dropwise addition of the solubilized inclusion body protein to a solution containing 0.5 M arginine and oxidized glutathione at pH 8. It has been proposed that arginine inhibits protein aggregation during refolding, while the oxidized glutathione promotes the formation of disulfide bonds (Clark et al., 1999). This buffer resulted in good recovery of RegIIIγ (27% of total inclusion body protein) following removal of arginine by dialysis (Table 3).

TABLE 3

Purification of recombinant mouse RegIIIγ and human HIP/PAP from overexpressing *Escherichia coli*

| | RegIIIγ | | HIP/PAP | |
|---|---|---|---|---|
| Purification step | Total protein (mg) | Protein yield (%) | Total protein (mg) | Protein Yield (%) |
| Cell lysate | 134 | 100 | 176 | 100 |
| Solubilized inclusion bodies | 34 | 25 | 28 | 16 |
| Post-refolding dialysate | 9 | 6.7 | 22 | 12.5 |
| SP-Sepharose eluate | 7.9 | 6.0 | 12 | 6.8 |

Results are derived from 500 ml cultures of *E. coli* expressing the recombinant proteins. Total protein was estimated by the method of Bradford (1976).

Attempts to refold HIP/PAP using the RegIIIγ refolding buffer resulted in a large amount of aggregation and the recovery of negligible soluble HIP/PAP. The inventors therefore screened a variety of refolding conditions including cations ($Ca^{2+}$, $Mg^{2+}$), chelator (EDTA), salt (NaCl, KCl), pH, and additives such as L-arginine and sucrose. As detailed in Materials and Methods, the inventors obtained the best recoveries of soluble HIP/PAP using a solution containing KCl, NaCl, cations, guanidine, sucrose, arginine, and a mixture of reduced and oxidized glutathione. Following dialysis, the yield of soluble HIP/PAP was 78% of total inclusion body protein.

RegIIIγ and HIP/PAP both have a basic predicted pI (8.5 for RegIIIγ and 7.8 for HIP/PAP, as calculated by the algorithm found at the ExPASy website. Thus the inventors predicted that both recombinant proteins would bind to a cation exchange resin. Furthermore, recombinant HIP/PAP produced in transgenic mice has previously been shown to bind to a Mono S cation-exchange column (Christa et al., 2000). Following refolding, the proteins were dialyzed into a low ionic strength buffer at pH 6 and were bound to SP-Sepharose. RegIIIγ was eluted in 0.4 M NaCl (FIG. 2), and yielded ~16 mg/liter of culture (Table 3). HIP/PAP required 0.6 M NaCl for elution (FIG. 2), and yielded ~24 mg/liter of culture (Table 3).

EXAMPLE 2

Characterization of Recombinant Proteins

A. Methods

Purity of recombinant protein preparations was evaluated by SDS-PAGE through 15% gels, N-terminal sequencing on an ABI494 sequencer (PE Biosystems), and Matrix Assisted Laser Desorption/Ionization Time of Flight (MALDI-TOF) mass spectrometry on a Micromass spectrometer.

Size exclusion chromatography was performed using a 1.5×63 cm Sephacryl S-100 column, at a flow rate of 22 ml/hour. The column was equilibrated in 25 mM Tris-HCl pH 7.5, 25 mM NaCl, 2 mM $CaCl_2$. 1 ml of protein at 2 mg/ml was applied and eluted in equilibration buffer, and eluted fractions were monitored for protein at 280 nm. Molecular weights were determined in comparison to the standards provided in the Amersham Low Molecular Weight Calibration Kit (GE Healthcare).

Circular dichroism (CD) analysis was performed on an Aviv 62DS spectropolarimeter with a 1 mm cell length. Spectra of purified RegIIIγ and HIP/PAP were recorded in 25 mM Tris-HCl pH 7.5, at a protein concentration of 10 μM. Three spectra were recorded for each condition from 190 to 260 nm in 1 nm increments, averaged, and the background spectrum of buffer without protein was subtracted from the protein-containing spectra. CD spectra were initially analyzed by the software accompanying the spectropolarimeter. Analysis of spectra to extrapolate secondary structures was performed by Dichroweb (Lobley et al., 2002) using the K2D and Selcon 3 analysis programs (Bohm et al., 1992; Sreerama et al., 1994).

B. Results

The purities of the recombinant proteins were assessed initially by SDS-PAGE. Following elution from SP-Sepharose, RegIIIγ and HIP/PAP migrated as single species (FIG. 2). To further confirm their identities, the purified proteins were analyzed by MALDI-TOF mass spectrometry. RegIIIγ yielded a single peak corresponding to a molecular mass of 16.6 kD, in good agreement with the predicted molecular mass of the mature protein (16.5 kD). Likewise, analysis of purified HIP/PAP gave a single peak indicating a molecular mass of 16.4 kD, in agreement with its predicted molecular mass (16.7 kD). Furthermore, Edman N-terminal sequencing of recombinant RegIIIγ yielded MEVAK for RegIIIγ, the expected amino terminus of the mature [$Met^{-1}$] protein. Likewise, analysis of the HIP/PAP N-terminus yielded the sequence MEEPQ, which corresponds to the predicted N-terminus of the recombinant mature [$Met^{-1}$] protein.

Figure 3:
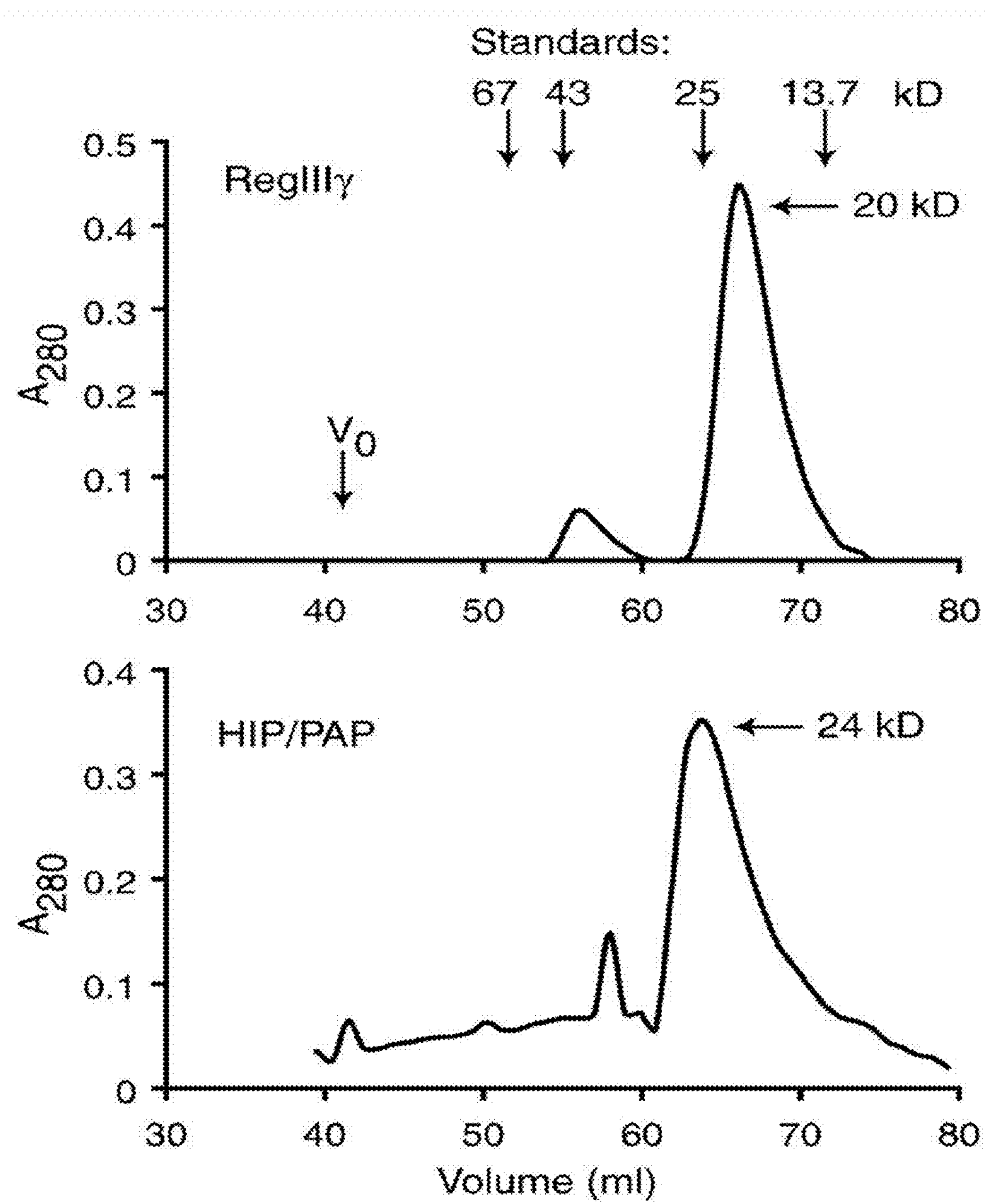
FIG. 3A and FIG. 3B show size exclusion chromatography of RegIIIγ and HIP/PAP. 2 mg samples of pure RegIIIγ (FIG. 3A) and HIP/PAP (FIG. 3B) were applied to a Sephacryl S-100 column and eluted with detection at 280 nm. Positions of void volume ($V_0$) and standards are indicated: albumin (67 kD), ovalbumin (43 kD), chymotrypsinogen (25 kD), and ribonuclease (13.7 kD).

Size-exclusion chromatography was performed to determine whether the recombinant proteins formed oligomers in solution. Chromatography through Sephacryl S-100 revealed that RegIIIγ elutes at a molecular mass of 20 kD (FIG. 3). While this corresponds to a molecular weight slightly greater than the predicted molecular mass of monomeric protein (16 kD), dimer would likely elute at a molecular weight in excess of 32 kD. Although a minor protein peak was observed at a molecular weight approximating that of dimer, the results suggest that the majority of RegIIIγ is a monomer in solution. Similarly, HIP/PAP exhibits a major elution peak at 26 kD, suggesting that it also is predominantly monomeric in solution.

Previous crystallographic analysis of HIP/PAP has elucidated a secondary structure that is composed of 9 β-strands and 2 α-helices (Abergel et al., 1999). This structure is very similar to those of virtually all other C-type lectin CRDs characterized (Drickamer, 1999). The inventors performed circular dichroism spectroscopy to characterize the secondary structures of purified recombinant RegIIIγ and HIP/PAP. The results for both proteins reveal maximal negative ellipticity in the range of 205-215 nm (FIG. 4), and the spectra were similar overall to those derived from other C-type lectin family members, including langerin (Stambach et al., 2003), surfactant protein A (Taneva et al., 1997), and mannose binding lectin (Weis et al., 1994). Indeed, analysis of the spectra by Dichroweb (Lobley et al., 2002) using the K2D and Selcon 3 analysis programs (Bohm et al., 1992; Sreerama et al., 1994) indicate that RegIIIγ and HIP/PAP are both predominantly comprised of β-sheet structure, while α-helix structure is not as prevalent. These findings are thus consistent with the secondary structures revealed by the HIP/PAP crystal structure as well as those other C-type lectin CRDs. These results indicate that purified recombinant RegIIIγ and HIP/PAP have acquired their expected secondary structures and are thus correctly refolded.

EXAMPLE 3

Western Blot Analysis

Recombinant mammalian proteins expressed in *E. coli* generally lack the post-translational modifications present on their endogenous counterparts. Such differences can pose difficulties for functional and biochemical analysis of recombinant proteins. Previous studies have demonstrated the existence of an O-glycosylated form of another Reg family member, human RegIα(Bertrand et al., 1996). Analysis of the RegIIIγ primary sequence indicates that the protein does not harbor a consensus sequence for N-glycosylation (Asn-Xaa-Ser/Thr). However, there is at least one potential O-glycosylation site as determined by the NetOGlyc algorithm at Expasy (Julenius et al., 2005). To determine whether the endogenous protein is postranslationally modified by glycosylation or another modification, the inventors compared the molecular weight of the endogenous protein with that of recombinant RegIIIγ.

Briefly, purified RegIIIγ was submitted to Cocalico Biologicals for polyclonal antibody generation in rabbits. Protein extracts for Western blot analysis were generated from mouse small intestine (jejunum). A 2 cm piece of freshly isolated intestinal tissue was flushed, lyophilized overnight, and pulverized under liquid $N_2$. The pulverized tissue was resuspended in 1 ml of Extraction Buffer (8 M urea, 1% SDS, 0.15 M Tris-HCl pH 7.5) and lysed by passing the suspension through an 18 gauge needle 3-5 times, followed by 3-5 passages through a 21 gauge needle. Total protein was quantitated with the Bio-Rad Detergent Compatible (DC) protein assay (Bio-Rad). Tissue protein and recombinant RegIIIγ were subjected to SDS-PAGE electrophoresis in a 15% gel and transferred to PVDF (Millipore). Membranes were blocked with 5% nonfat milk and incubated with polyclonal antiserum or preimmune serum followed by horseradish peroxidase-conjugated goat anti-rabbit IgG (Jackson ImmunoResesarch). Immunoreactivity was detected using the Pierce SuperSignal West Pico Chemiluminescent detection kit.

Figure 5:
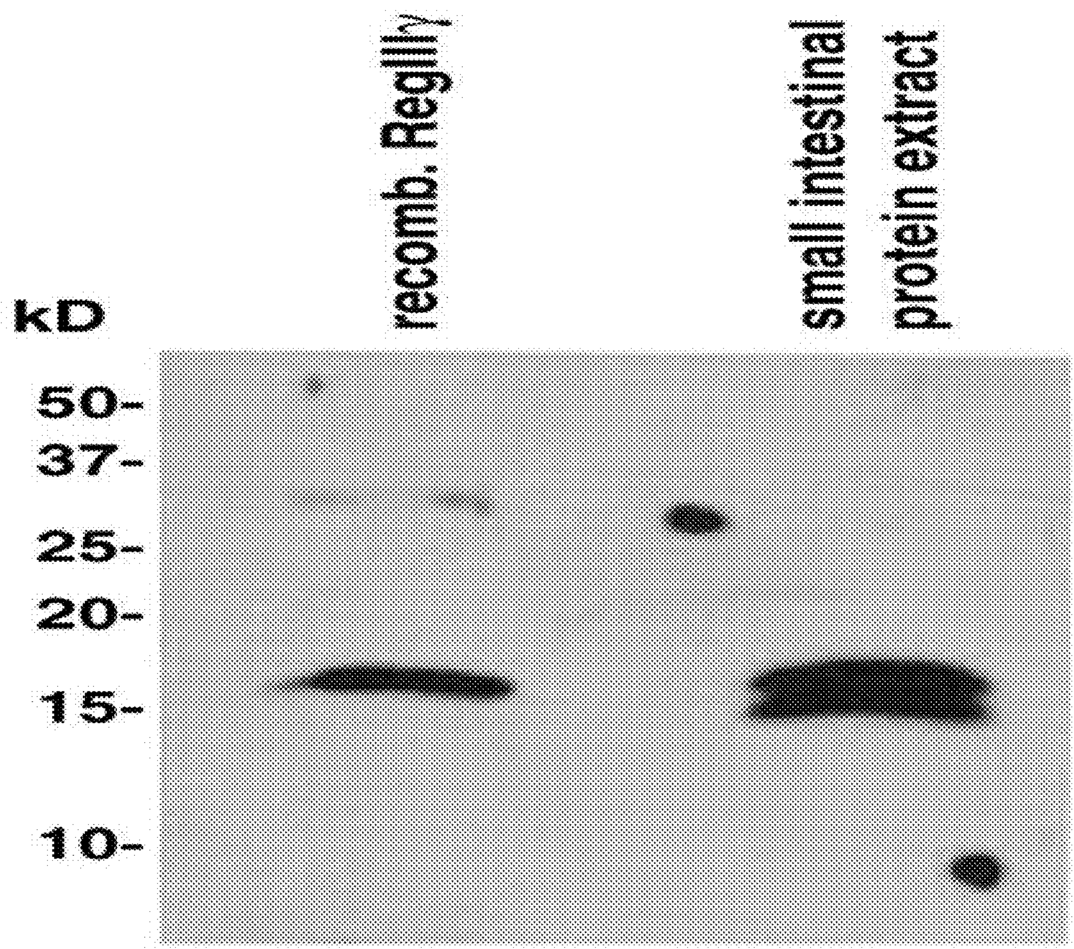
FIG. 5 shows Western blot comparison of recombinant and endogenous mouse RegIIIγ. 5 ng of purified recombinant RegIIIγ and 20 μg of total intestinal protein were separated by SDS-PAGE and transferred to PVDF. The blot was probed with rabbit antiserum raised against recombinant RegIIIγ.

Western blot analysis revealed that the recombinant protein migrated at the same molecular weight as protein from intestinal tissue homogenates (FIG. 5). The lower band detected in the endogenous sample is identical in molecular weight to a cleaved form that the inventors observed following exposure of recombinant RegIIIγ to exogenous proteases, suggesting that RegIIIγ is processed in vivo by endogenous intestinal proteases. These results are thus consistent with the conclusion that RegIIIγ is not modified by glycosylation. However, it is still possible that endogenous RegIIIγ harbors other post-translational modifications that are undetectable by SDS-PAGE analysis.

EXAMPLE 4

Carbohydrate Binding Assays

The primary amino acid sequences of both RegIIIγ and HIP/PAP are composed almost entirely of a conserved C-type lectin carbohydrate recognition domain (CRD). According to the classification scheme proposed by Drickamer and Fadden, both proteins are members of the type VII C-type lectin subfamily (Drickamer et al., 2002). Although members of the other subfamilies have well-characterized carbohydrate ligands, the ligands bound by type VII lectins, including RegIIIγ and HIP/PAP, are poorly characterized. Carbohydrate binding specificity of these proteins were performed to gain insight into these characteristics. The inventors covalently coupled various mono-, di-, and polysaccharides to Sepharose 6B resin and assayed for binding of purified RegIIIγ and HIP/PAP.

Briefly, yeast mannan (Sigma) and dextran (Sigma) were coupled to Sepharose 6B using a previously published protocol (Taylor et al., 2003). Mannose-agarose was purchased from Sigma. 25 μl of each resin was washed extensively in Binding Buffer (25 mM MES pH 6.0, 25 mM NaCl, 1% BSA), and 50 μg recombinant protein was added to each resin in a total volume of 1 ml of Binding Buffer. After rotation for 2 hours at 4° C., the beads were washed twice with 1 ml of Wash Buffer (25 mM MES pH 6.0, 25 mM NaCl). Bound protein was eluted by boiling the beads in SDS-PAGE buffer (10% glycerol, 5% β-mercaptoethanol, 2% SDS, 62.5 mM Tris-HCl, 0.003% bromophenol blue, pH 6.8) and resolved by SDS-PAGE through a 15% acrylamide gel.

Ten ml mannose-Sepharose or mannan-Sepharose columns were run in 25 mM MES pH 6.0, 25 mM NaCl, and were eluted in 25 mM MES pH 6.0, 25 mM NaCl containing either 10 mM $CaCl_2$ or 20 mM $CaCl_2$. Collected fractions were analyzed for protein content by spectrophotometry at 280 nm.

None of the immobilized monosaccharides tested (glucose, galactose, N-acetylglucosamine, N-acetylgalactosamine, mannose, fucose) supported binding of either lectin (data not shown). In addition, the inventors did not observe binding to the disaccharide lactose (data not shown). This is in contrast to a previous report demonstrating that lactose is a ligand for GST-tagged HIP/PAP (Christa et al., 1994). However, the inventors found that RegIIIγ and HIP/PAP both bound to immobilized mannan (FIG. 6), a polysaccharide composed of polymerized mannose. By contrast, neither protein bound to dextran, a polysaccharide composed of α1,6- and α1,3-linked glucose, suggesting that both lectins are specific for mannose polysaccharides. Moreover, the inventors did not detect binding of either protein to mannose (FIG. 6), suggesting that RegIIIγ and HIP/PAP bind polymeric but not monomeric mannose.

Figure 6:
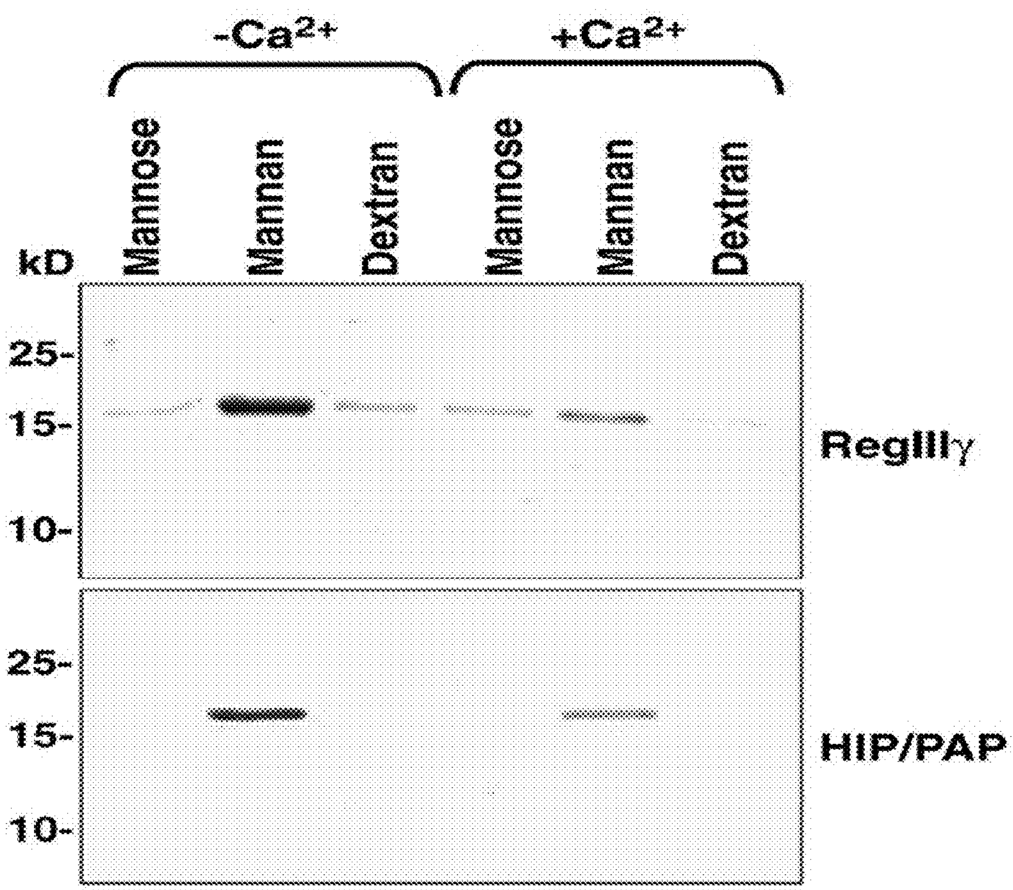
FIG. 6 shows RegIIIγ and HIP/PAP binding to immobilized saccharides. 50 μg of each protein was bound to 25 μl of immobilized mono- or polysaccharide for 2 hours at 4° C. After washing, bound proteins were released by boiling the Sepharose beads in SDS-PAGE sample buffer followed by electrophoresis through 15% polyacrylamide gels and Coomassie blue staining.

The C-type lectin family includes members whose ligand binding is calcium-dependent. However, previous studies have shown that at least one other Reg family member, RegIα, does not bind $Ca^{2+}$ (Bertrand et al., 1996). Furthermore, crystallographic analysis of RegIα revealed significant alterations in the polypeptide loop that binds $Ca^{2+}$ in other C-type lectins (Bertrand et al., 1996). The inventors therefore asked whether RegIIIγ and HIP/PAP binding to mannan is influenced by $Ca^{2+}$. Unexpectedly, these results revealed that 10 mM $CaCl_2$ reduces binding of both RegIIIγ and HIP/PAP to mannan (FIG. 6). These results thus suggest that carbohydrate ligand binding to RegIIIγ and HIP/PAP is indeed modulated by $Ca^{2+}$, but in a way that is distinct from other C-type lectins.

Figure 7:
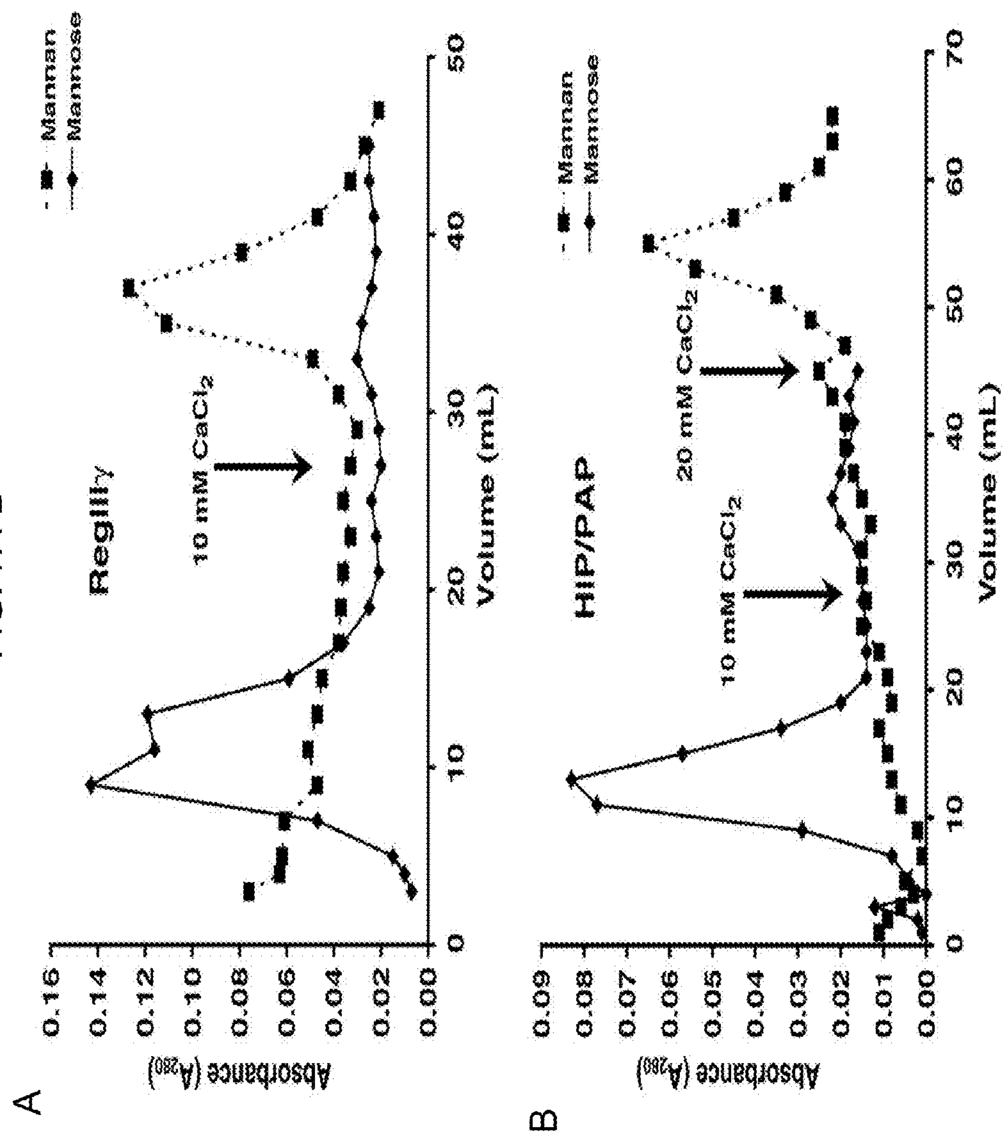
FIGS. 7A-B show chromatography of RegIIIγ (FIG. 7A) and HIP/PAP (FIG. 7B) on mannose- and mannan-Sepharose. 0.25 mg of each purified protein was applied to a 10 ml mannose- or mannan-Sepharose column. 2 ml fractions were collected and protein was detected by spectrophotometry at 280 nm. Protein bound to mannan-Sepharose was eluted with 10 mM or 20 mM $CaCl_2$ as indicated.

The inventors next wished to determine whether the entire purified RegIIIγ and HIP/PAP protein populations are capable of binding to mannan. The inventors therefore applied purified recombinant protein to a column of mannose- or mannan-conjugated Sepharose beads. As expected, both proteins passed through the mannose-Sepharose column (FIG. 7). In contrast, RegIIIγ and HIP/PAP bound quantitatively to the mannan-Sepharose column (FIG. 7), indicating that each purified protein population is refolded to a functionally active state in its entirety. Furthermore, the inventors eluted both mannan bound proteins with $CaCl_2$, confirming that both lectin-carbohydrate interactions are inhibited by $Ca^{2+}$.

EXAMPLE 5

Expression of RegIII and HIP/PAP

A. Materials and Methods

Reagents. Recombinant RegIIIγ and HIP/PAP were expressed and purified according to methods outlined in (Cash et al., 2006). Anti-RegIIIγ antiserum was generated as previously described (Cash et al., 2006). Goat anti-rabbit horseradish peroxidase was from Jackson Immuno-Research. Chitooligosaccharides were purchased from Seikagaku. Peptidoglycan purified from *Bacillus subtilis*, mannan from *Saccharomyces cerevisiae*, crab shell chitin, and cellulose were purchased from Sigma-Aldrich. SYBR Green was from Stratagene; other real-time PCR reagents were from Invitrogen.

Germ-free mice. Germ-free NMRI/KI mice (Hooper, 2001) were maintained in plastic gnotobiotic isolators on a 12 hour light cycle and given free access to an autoclaved chow diet. 8-12 week old males were inoculated with an unfractionated microbiota isolated from ileum/cecum of conventionally-raised NMRI/KI mice. The resulting mice were designated "conventionalized." Mice were killed 10 days later, and small intestinal tissues were prepared for laser capture microdissection as described below or snap frozen for RNA or protein extraction alongside age- and gender-matched germ-free controls. For monocolonization experiments, age-matched germ-free C57/b6 and RAG1-deficient mice were inoculated with stationary phase cultures of *Bacteroides thetaiotaomicron* (strain VPI-5482) and *Listeria innocua* (strain CLIP 11262) by spreading the organisms on fur as previously described (Hooper, 2001). Mice were killed 10 days later, and the distal 1 cm of intestine was used to determine CFU/ml ileal contents. All mice were colonized to ~$10_8$ CFU/ml.

Real-time PCR analysis. Total RNA was isolated from small intestinal tissues using the Qiagen RNeasy RNA isolation kit. RNAs were treated with deoxyribonuclease (Roche) prior to randomprimed cDNA synthesis and real-time PCR analysis. SYBR Green-based real-time PCR used RegIIIγ-specific primers (forward primer: SEQ ID NO:51: 5'-TTCCTGTCCTCCATGATCAAAA; reverse primer: SEQ ID NO:52: 5'-CATCCACCTCTGTTGGGTTCA). Control experiments established that amplicons were derived from cDNA and not from genomic DNA or primer-dimers. Signals were normalized to 18S rRNA (forward primer: SEQ ID NO:53: 5'-CATTCGAACGTCTGCCCTATC; reverse primer: SEQ ID NO:54: 5'-CCTGCTGCCTTCCTTGGA). Normalized data were used to quantitate relative levels of RegIIIγ using ΔΔCt analysis (S3).

Western Blot Analysis. Protein extracts for Western blot analysis were generated from small intestines of male age-matched germ-free or conventionalized NMRI/KI mice. A 2 cm piece of freshly isolated intestinal tissue was flushed, lyophilized overnight, and pulverized under liquid N2. The pulverized tissue was resuspended in 1 ml of Extraction Buffer (8 M urea, 1% SDS, 0.15 M Tris-HCl pH 7.5) and lysed by passing the suspension through an 18 gauge needle 3-5 times, followed by 3-5 passages through a 21 gauge needle. Total protein was quantitated with the Bio-Rad Detergent Compatible (DC) protein assay (Bio-Rad). Tissue protein and recombinant RegIIIγ were subjected to SDS-PAGE electrophoresis in a 15% gel and transferred to PVDF (Millipore). Membranes were blocked with 5% nonfat milk and incubated with polyclonal antiserum or preimmune serum followed horseradish peroxidase-conjugated goat anti-rabbit IgG (Jackson ImmunoResesarch). Immunoreactivity was detected using the Pierce SuperSignal West Pico Chemiluminescent detection kit.

Electron Microscopy. Paneth cell electron microscopy was performed as described (Hooper et al., 2003) with tissues isolated from a male C57/B6 mouse housed in a barrier facility. Freshly isolated intestine was divided into thirds, and the distal third was fixed overnight at 4° C. in 4% paraformaldehyde, 0.1% gluteraldehyde in 0.1 M phosphate buffer. Tissues were dehydrated in an ethanol gradient at decreasing temperatures (0 to −35° C.), then embedded in Lowicryl HW20 under UV illumination for two days. Embedded tissues were then sectioned using a microtome, floated onto grids, and visualized using the JEOL 1200 EX electron microscope. For electron microscopy of bacteria, mid-log phase cultures of *L. monocytogenes* (strain EGD-e) were washed and resuspended in 900 μl of 25 mM MES pH 6.0, 25 mM NaCl. 300 μl of resuspended bacteria were added to each of three reactions containing either buffer alone, 10 μM RegIIIγ, or 10 μM HIP/PAP. Reactions were incubated for 2 hours at 37° C. before the bacteria were pelleted. Bacteria were washed once with assay buffer, and each pellet was resuspended in 500 mL of 5% gluteraldehyde in 0.1M phosphate buffer. Bacterial pellets were cryo-embedded, sectioned, and positioned on grids as for the mouse tissues described above. Images were obtained using a JEOL 1200 EX electron microscope and AMT410 digital imaging equipment and software.

Flow Cytometry. Recombinant RegIIIγ was labeled with AlexaFluor555 using the Molecular Probes AlexaFluor555 MicroScale Protein Labeling kit. Intestinal bacteria were harvested from the small intestines of conventional C57/b6 mice. Sterile 25 mM MES pH 6, 25 mM NaCl was used to flush intestinal contents into the same buffer containing protease inhibitors (Roche) on ice. Large particulate matter was allowed to settle to the bottom of the tube, the cleared supernatant was removed to a fresh tube, and formaldehyde was added to each supernatant to a final concentration of 2%. After adding formaldehyde, the samples were incubated for fifteen minutes on ice. Additional particulate matter was separated by centrifugation at 500 rpm for 2 minutes, and the supernatant was retained. The supernatants were centrifuged at 4000 rpm for 5 minutes to pellet intestinal bacteria. The pellets were washed in 25 mM MES pH 6.0, 25 mM NaCl, 0.5% BSA and resuspended in 1 ml of the same buffer. 100 μl of resuspended bacteria were incubated with 30 μM RegIIIγ-AlexaFluor555 on ice for 40 minutes. Bacteria were washed twice with reaction buffer and subsequently incubated with or without WGAAlexaFluor488 (Molecular Probes). Bacteria were washed three times in buffer with no BSA, then resuspended in 2 ml of buffer without BSA and analyzed using a FACScalibur flow cytometer and CellQuest Pro analysis software. Mid-log phase cultures of *Enterococcus faecalis, Listeria innocua, Salmonella typhimurium* and *Pseudomonas aeruginosa* were pelleted at 4000 rpm for 5 minutes and fixed in 2% formaldehyde for 15 minutes. Following fixation, cells were washed in 25 mM MES pH 6.0, 25 mM NaCl, 0.5% BSA, and resuspended in 1 ml of the same buffer. 25 μl of each bacterial species was incubated with or without 30 μM RegIIIγ for 40 minutes on ice, followed by staining with rabbit anti-RegIIIγ and goat anti-rabbit-Cy3 (Biomeda). Bacterial pellets were then washed three times in buffer without BSA, resuspended in 2 ml of buffer without BSA, and analyzed as for intestinal bacteria.

B. Results

Figure 8:
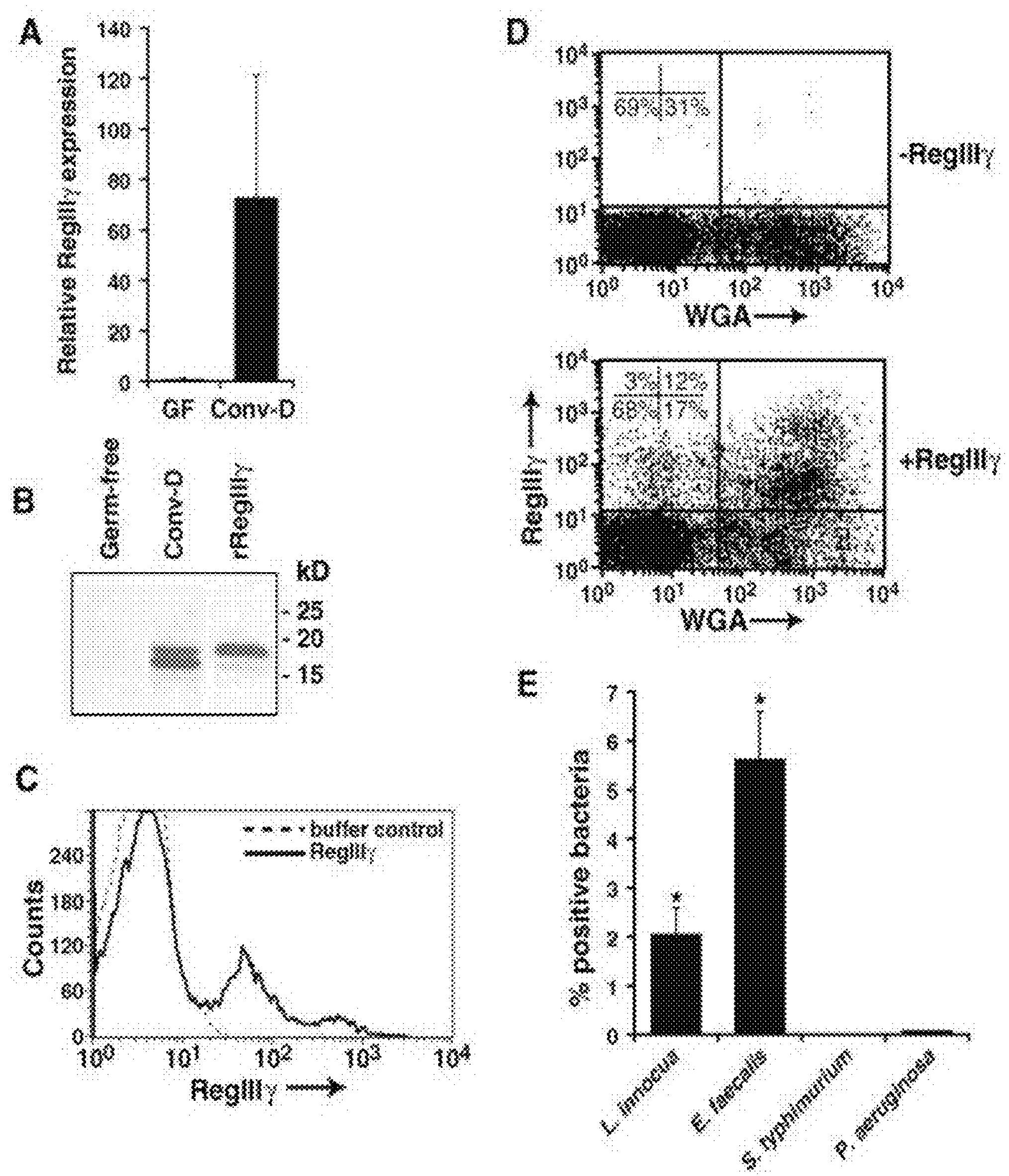
FIGS. 8A-8E show RegIIIγ is induced by resident intestinal microbes and binds to Gram-positive bacteria.

The inventors discovered that there was a 31-fold increase in the abundance of RegIIIγ transcripts in Paneth cells from conventionalized as compared to germ-free mice. Increased expression of RegIIIγ mRNA is shown by real-time PCR (FIG. 8A), and correlated with increased protein expression (FIG. 8B).

Figure 9:
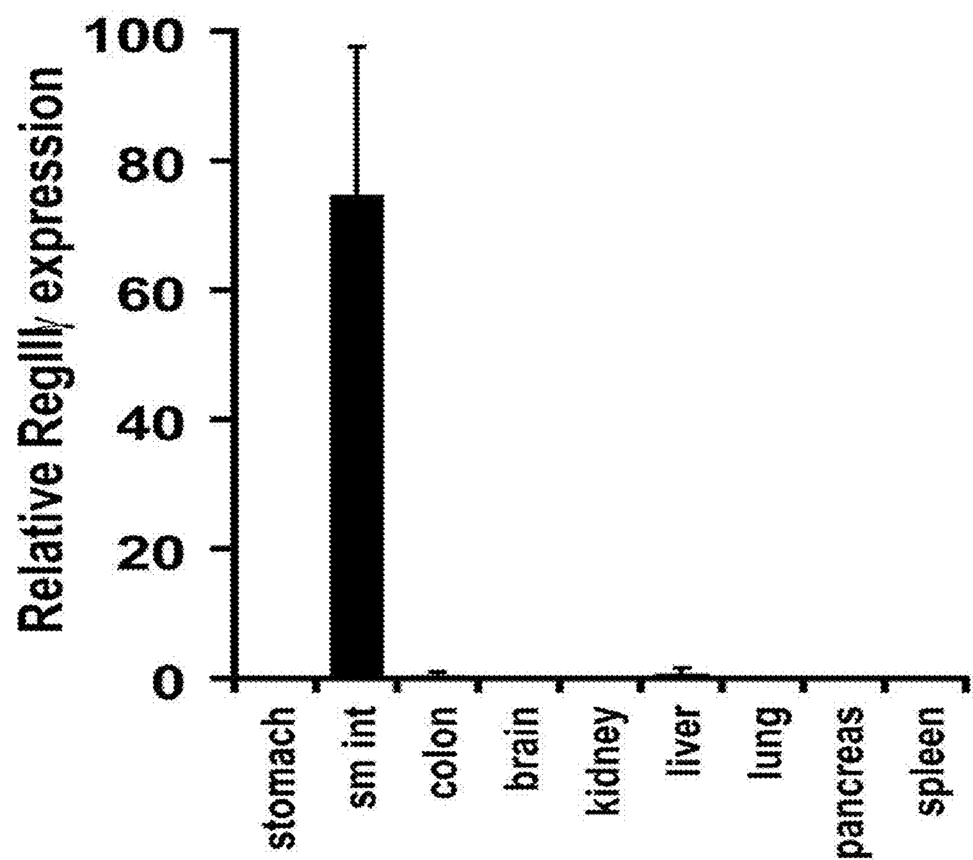
FIG. 9 shows RegIIIγ mRNA is expressed predominantly in mouse small intestine. RegIIIγ mRNA expression was determined by Q-PCR analysis of tissue RNAs from conventionally raised NMRI mice. RegIIIγ transcripts were normalized to 18S rRNA, and are expressed relative to small intestine, which is set at 100. Mean±s.d. from triplicate determinations are plotted. Sm int=small intestine.

The Reg gene family encodes a diverse group of secreted proteins that contain conserved sequence motifs found in C-type lectin carbohydrate recognition domains (CRDs). The Reg family constitutes a distinct group of mammalian C-type lectins, with each member consisting solely of a ~16 kD CRD and N-terminal secretion signal. The family is further classified into subgroups (I, II, III, and IV) based on primary sequence. Several RegIII family members are expressed predominantly in small intestine, including mouse RegIIIγ (FIG. 9) and human HIP/PAP (Christa et al., 1996; Ogawa et al., 2003). Inflammatory stimuli such as bacteria (Ogawa et al., 2003; Syder et al., 2003) or mucosal damage (Pull et al., 2005) increase gastrointestinal expression of mouse RegIIIγ. Furthermore, HIP/PAP expression increases in the mucosa of patients with inflammatory bowel disease (Ogawa et al., 2003; Dieckgraefe et al., 2002), a disorder characterized by increased mucosal adherence of resident bacteria and chronic intestinal inflammation (Swidsinski et al., 2002). Although mitogenic functions have been suggested for Reg proteins in other tissues (Livesey et al., 1997), the biological functions of intestinal RegIII proteins and their role in IBD have remained poorly defined. The inventors show that RegIIIγ and human HIP/PAP are peptidoglycan-binding proteins with direct antibacterial activity.

Figure 10:
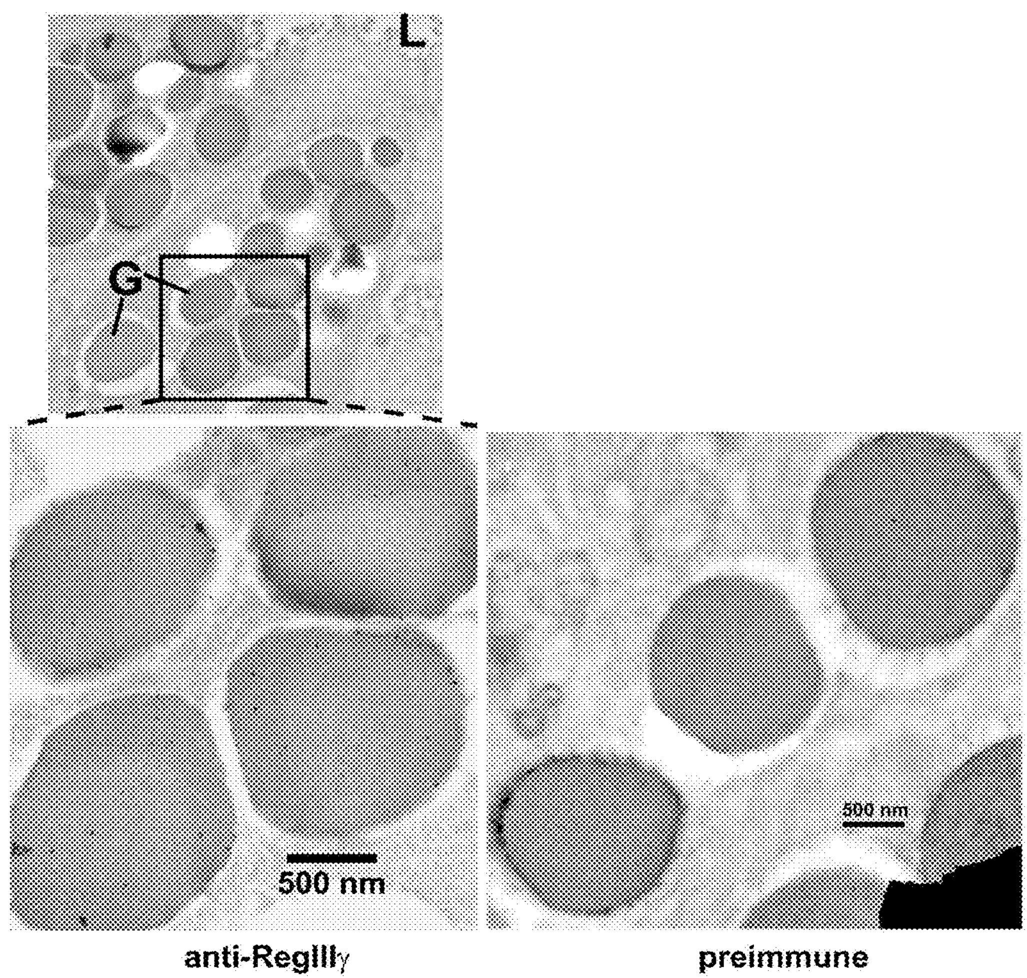
FIG. 10 shows RegIIIγ localizes to Paneth cell secretory granules. Sections were cut from blocks and incubated with anti-RegIIIγ and gold-labeled goat anti-rabbit IgG, and visualized by electron microscopy. G, granule; L, gut lumen. Bar=500 nm. Controls were incubated with pre-immune serum and goldlabeled goat anti-rabbit IgG. Representative photos of Paneth cell granules are shown here.

Immunogold electron microscopy revealed that RegIIIγ is present in Paneth cell secretory granules (FIG. 10). Since granule contents are released apically (Ayabe et al., 2000), this indicates that RegIIIγ is targeted to the gut lumen which harbors large resident bacterial populations. Other members of the C-type lectin family, such as the mannose binding lectin (MBL), bind to microbial surface carbohydrates and trigger innate immune responses (Ezekowitz, 2003). Therefore the inventors hypothesized that RegIIIγ might similarly bind intestinal bacteria. Previously, the inventors established a procedure for purification of recombinant mouse RegIIIγ and human HIP/PAP (Cash et al., 2006). The inventors used fluorochrome-conjugated recombinant RegIIIγ to look for binding to a mixed microbial population harvested from the small intestines of conventionally-raised mice. Flow cytometry revealed that RegIIIγ bound to a sub-population of intestinal bacteria (FIG. 8C).

Given that intestinal microbial communities consist of both Gram-positive and Gram-negative species (Eckburg et al., 2005), the inventors asked whether RegIIIγ bound preferentially to one of these groups. Wheat germ agglutinin binds to surface peptidoglycan on Gram-positive bacteria, thus distinguishing between Gram-positive and Gram-negative populations (Holm et al., 2003). Dual staining with fluorochrome-conjugated RegIIIγ and WGA revealed that RegIIIγ preferentially bound to the WGA-positive bacterial population (FIG. 8D). The inventors furthermore found that RegIIIγ bound to pure preparations of cultured Gram-positive bacteria, including *Listeria innocua* and *Enterococcus faecalis*, with comparatively little binding to preparations of cultured Gram-negative bacteria, including *Salmonella typhimurium* and *Pseudomonas aeruginosa* (FIG. 8E).

EXAMPLE 6

Binding Studies

A. Materials and Methods

Peptidoglycan Binding Assays. Peptidoglycan from *Bacillus subtilis* (Sigma) was pelleted and washed in Wash Buffer (25 mM MES pH 6.0, 25 mM NaCl). 10 μg of recombinant RegIIIγ or HIP/PAP were added to 50 μg of peptidoglycan in a final volume of 200 μl. Reactions were incubated for 2 hours at 4° C., then the peptidoglycan was pelleted at 6000 g for 5 minutes and washed 2× in Wash Buffer. Bound protein was eluted by boiling the peptidoglycan in 2×SDS-PAGE buffer (10% glycerol, 5% β-mercaptoethanol, 2% SDS, 62.5 mM Tris-HCl, 0.003% bromophenol blue, pH 6.8) and resolved by SDS-PAGE through 15% SDS-acrylamide gels. Gels were stained with Coomassie Blue. For inhibition experiments, soluble peptidoglycan was generated by sonication of insoluble peptidoglycan as described (S5). Ten μg of recombinant RegIIIγ or HIP/PAP was pre-incubated for 2 hours at 4° C. with 100 μM soluble peptidoglycan fragments from *Bacillus subtilis*. The entire pre-incubation mixture was then applied to 2 μg of pelleted, washed insoluble peptidoglycan. Reactions containing protein, insoluble, and soluble peptidoglycan were incubated for 30 minutes at 4° C., then the peptidoglycan was pelleted at 6000 g for 5 minutes and washed 3× in Wash buffer. Bound protein was eluted by boiling the peptidoglycan in 2×SDS-PAGE buffer (10% glycerol, 5% β-mercaptoethanol, 2% SDS, 62.5 mM Tris-HCl, 0.003% bromophenol blue, pH 6.8) and resolved by SDS-PAGE through 15% acrylamide gels. Bound recombinant RegIIIγ and HIP/PAP were detected using Western blotting as described above.

Determination of dissociation constants ($K_d$). Purified recombinant RegIIIγ or HIP/PAP (200 mg) was labeled with 1 mCi of $^{125}$I (GE Healthcare) using Iodobeads (Pierce). Incorporated and free counts were separated by passage over a D-Salt Excellulose desalting column (Pierce). For the binding assay, increasing amounts of labeled protein were added to 10 μg of *Bacillus subtilis* peptidoglycan (Sigma), and were incubated for 1 hour at room temperature. The peptidoglycan was pelleted at 6000 g for 5 minutes, the supernatant was removed and the unbound (free) counts were quantitated. The pellet was washed 2× in Wash Buffer (25 mM MES pH 6.0, 25 mM NaCl), and the bound counts were quantitated. Nonspecific binding was determined by performing the assay in the presence of 50 μg of unlabeled RegIIIγ or 25 μg of unlabeled HIP/PAP. Specific binding was the difference between total binding and nonspecific binding. The apparent dissociation constant, Kd, was determined by nonlinear regression analysis using GraphPad Prism software.

Carbohydrate Binding Assays. *Saccharomyces cerevisiae* mannan (Sigma), crab shell chitin (Sigma), or dextran (Sigma) were coupled to Sepharose 6B using a previously published protocol (S6). 25 μl of each resin was washed extensively in Binding Buffer (25 mM MES pH 6.0, 25 mM NaCl, 1% BSA), and 50 μg recombinant protein was added to each resin in a total volume of 1 ml of Binding Buffer. After a 2 hour incubation at 4° C., the beads were washed twice with 1 ml of Wash Buffer (25 mM MES pH 6.0, 25 mM NaCl). Bound protein was eluted by boiling the beads in SDS-PAGE buffer (10% glycerol, 5% β-mercaptoethanol, 2% SDS, 62.5 mM Tris-HCl, 0.003% bromophenol blue, pH 6.8) and resolved by SDS-PAGE through 15% acrylamide gels. Gels were stained with Coomassie Blue.

B. Results

Figure 11:
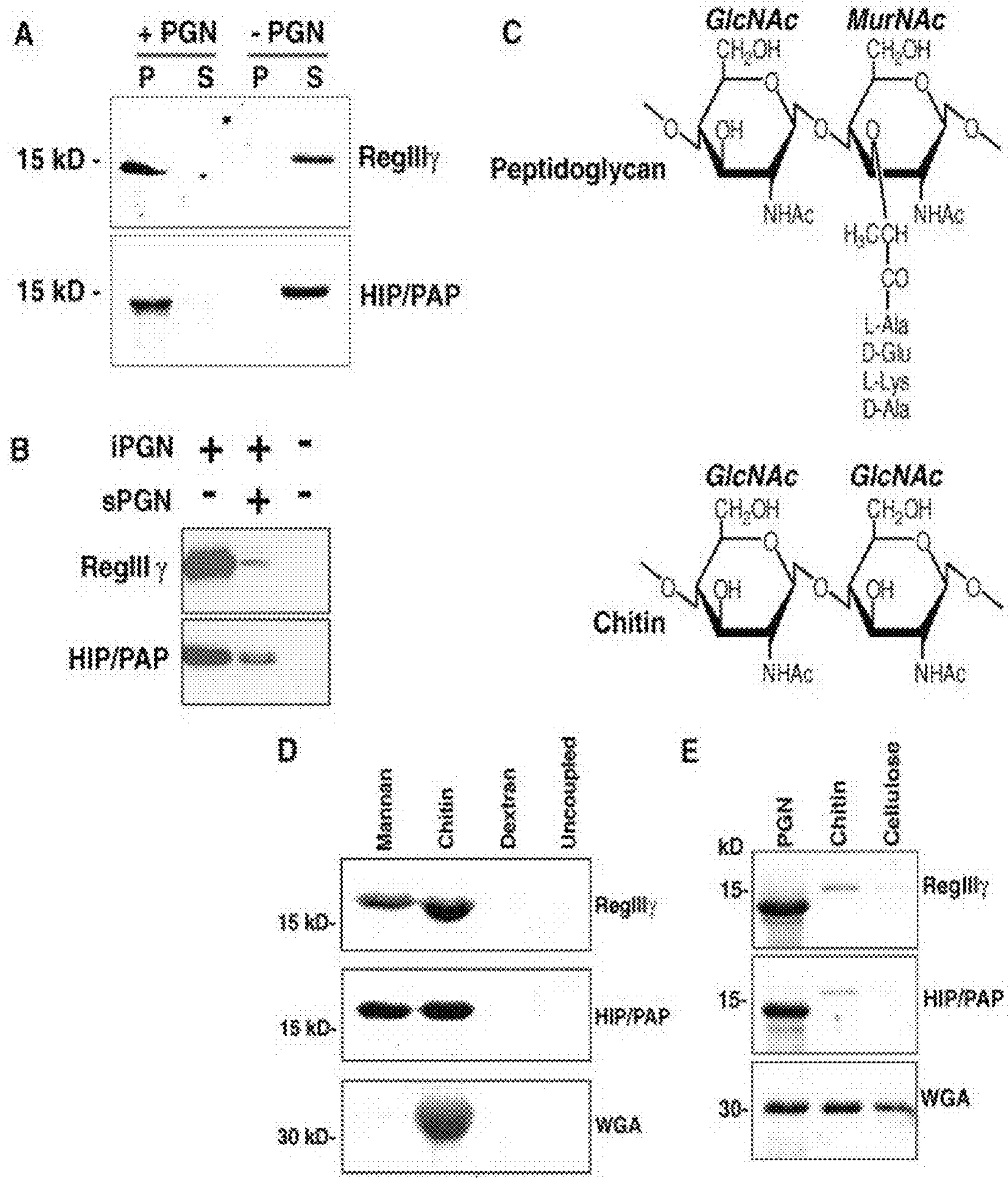
FIGS. 11A-11E show mouse RegIIIγ and human HIP/PAP bind peptidoglycan.
Figure 12:
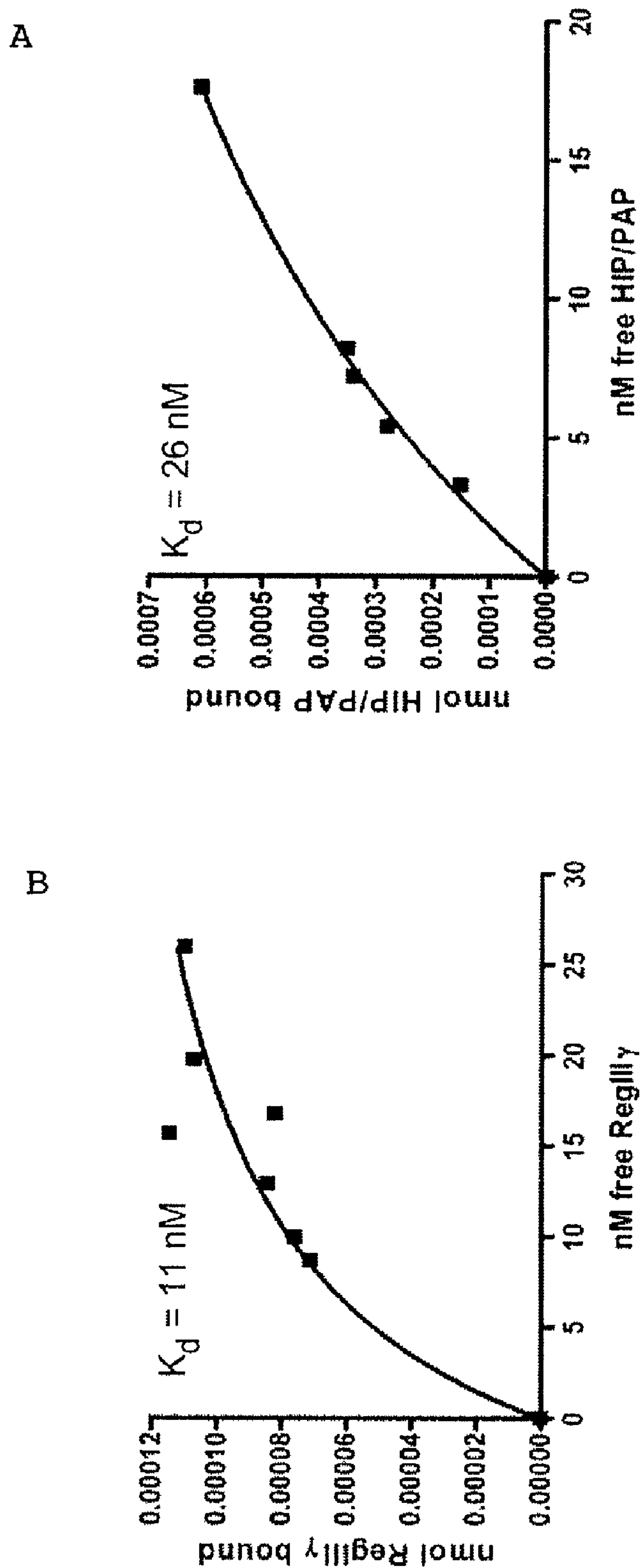
FIGS. 12A and 12B show RegIIIγ and HIP/PAP bind to peptidoglycan with nanomolar affinities. Increasing concentrations of $^{125}$I-RegIIIγ (FIG. 12) and $^{125}$I-HIP/PAP (FIG. 12B) were incubated with 10 μg of *Bacillus subtilis* peptidoglycan. The amounts of labeled protein bound to peptidoglycan or remaining unbound were measured by gamma counting. Specific binding was calculated by subtracting the amount of protein bound in the presence of 50 μg (RegIIIγ) or 25 μg (HIP/PAP) of unlabeled protein from the total protein bound in the absence of unlabeled protein. The inventors consistently observed evidence of cooperative binding at free lectin concentrations of >30 nM (RegIIIγ) and >25 nM (HIP/PAP), which is similar to the behavior of mammalian PGRP (S7). Therefore, dissociation constants ($K_d$) were determined by non-linear regression of data points corresponding to free lectin concentrations of <30 nM (RegIIIγ) and <25 nM (HIP/PAP).

These findings suggested that RegIIIγ binds peptidoglycan, a molecule that is exposed on the Gram-positive bacterial surface but buried in the periplasmic space of Gram-negative bacteria. To test this idea, the inventors performed pull-down assays using insoluble cell wall peptidoglycan (Werner et al., 2000). Purified RegIIIγ was completely removed from solution by incubation with peptidoglycan, and was retained in the peptidoglycan-bound fraction after extensive washing (FIG. 11A). Human HIP/PAP is 65% identical to RegIIIγ and exhibited a similar peptidoglycan binding activity (FIG. 11A). The specificity of both interactions was confirmed by using soluble peptidoglycan (sPGN) to compete for binding to insoluble peptidoglycan (iPGN; FIG. 11B). Furthermore, the inventors calculated a dissociation constant ($K_d$) of 11 nM for RegIIIγ and 26 nM for HIP/PAP (FIG. 12). These results indicate high affinity binding to peptidoglycan, and are in good agreement with the dissociation constants determined for other known peptidoglycan binding proteins, including CD14 (Dziarski et al., 1998) and members of the peptidoglycan recognition protein (PGRP) family (Liu et al., 2000).

Peptidoglycan consists of extended glycan chains composed of alternating N-acetylglucosamine (GlcNAc) and N-acetylmuramic acid (MurNAc) residues cross-linked by short peptides (FIG. 11C). Because RegIIIγ and HIP/PAP contain predicted CRDs, the inventors determined whether they recognize the carbohydrate moiety of peptidoglycan. Chitin is composed of β1,4-linked GlcNAc chains that are virtually identical to the peptidoglycan carbohydrate backbone (FIG. 11C). As shown in FIG. 11D, purified recombinant RegIIIγ and HIP/PAP bound to chitin immobilized on Sepharose beads. Both lectins also bound to mannan, a polymer of mannose residues (FIG. 11D). This is consistent with the fact that C-type lectins that bind GlcNAc-containing saccharides frequently also bind mannose-containing saccharides (Drickamer, 1992) due to the similar arrangements of the 3- and 4-hydroxyls of these sugars. In contrast, neither lectin bound dextran-Sepharose or uncoupled Sepharose (FIG. 11D). No binding was detected to monomeric GlcNAc-Sepharose or mannose-Sepharose (data not shown), indicating that both lectins show specificity for polymeric carbohydrates. Although the C-type lectin family includes members that bind their ligands in a calcium-dependent manner, the inventors found that RegIIIγ and HIP/PAP do not require calcium for binding to peptidoglycan and chitin. Taken together, these results suggest that RegIIIγ and HIP/PAP are pattern recognition proteins that recognize the microbe-associated molecular pattern represented by the extended glycan chains of peptidoglycan.

Chitin binding activity was also detected in pull-down assays in which the inventors assessed RegIIIγ and HIP/PAP binding to equivalent masses of peptidoglycan and chitin (FIG. 11E). Peptidoglycan bound more RegIIIγ and HIP/PAP as compared to chitin, suggesting that both lectins bind more avidly to peptidoglycan than to chitin. Neither lectin bound to cellulose, a β1,4-linked glucose polymer.

EXAMPLE 7

Assays for Microbicidal Activity

A. Method

Target microorganisms were grown to mid-log phase in brain-heart infusion (BHI) broth and resuspended in 25 mM MES pH 6, 25 mM NaCl. Initial bacterial concentrations ranged from $10^5$ to $10^6$ CFU/ml. After incubation for 2 hours at 37° C., viable bacteria were quantitated by dilution plating on BHI agar plates. Inhibition assays were performed by pre-incubating lectin for 10 min with chitooligosaccharides or sPGN prior to addition of bacteria. To assay microbicidal activity under native intestinal conditions, recombinant purified RegIIIγ was infused into isolated intestinal segments from FVB/n mice singly colonized with *Listeria innocua* (strain CLIP 11262). Two 1 cm adjacent ileal segments in each mouse were clamped off using hemostats. One segment was infused with 100 μl of sterile buffer alone (25 mM MES pH 6, 25 mM NaCl) and the other was infused with 100 μl of purified recombinant RegIIIγ in the same buffer (protein concentrations were 4-7 mg/ml). After 30 minutes, luminal contents from each segment were sampled in triplicate and numbers of *Listeria innocua* were quantitated by dilution plating on Brain-Heart-Infusion agar plates.

B. Results

Figure 13:
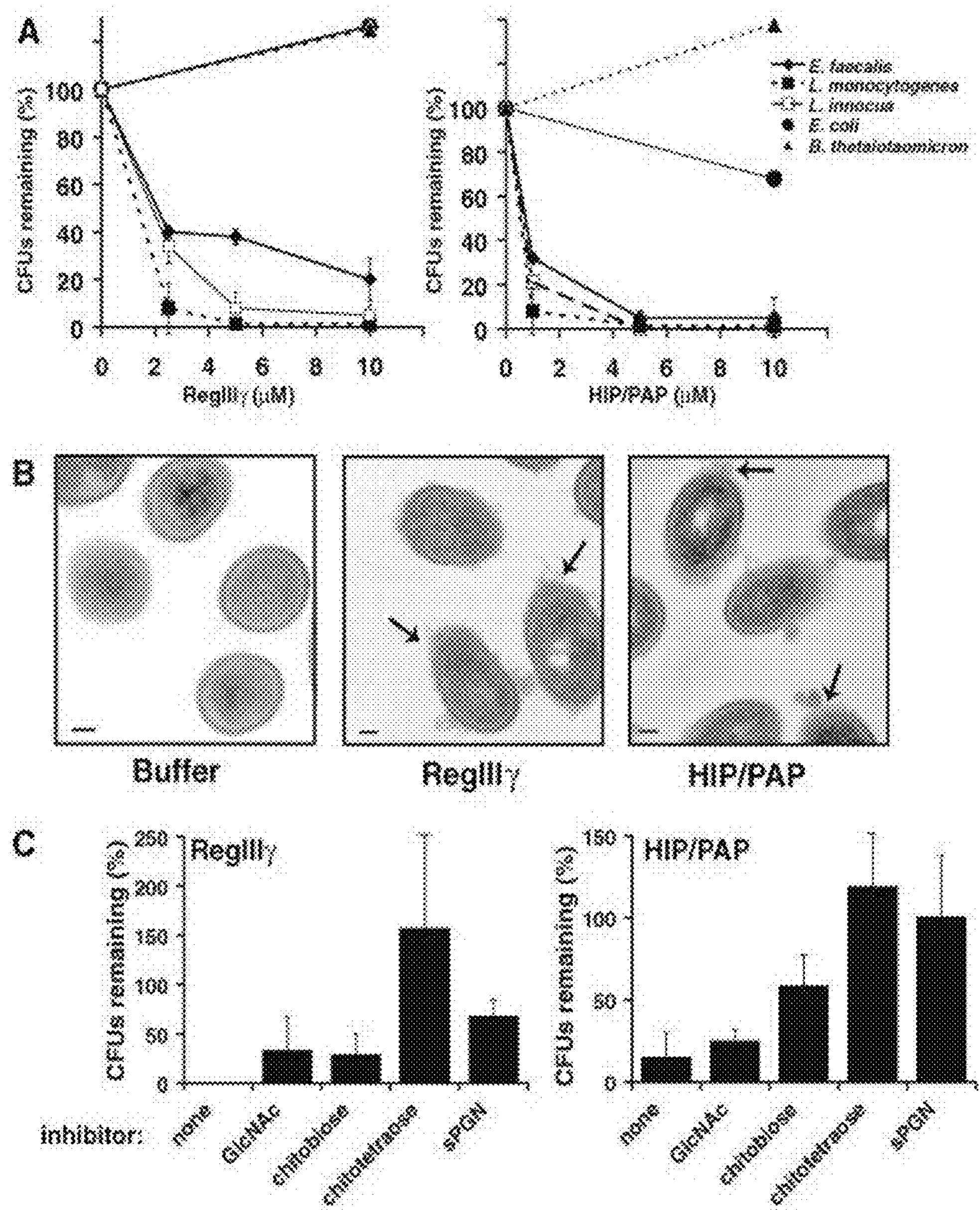
FIGS. 13A-13C show mouse RegIIIγ and human HIP/PAP have antibacterial activity against Gram-positive bacteria.
Figure 14:
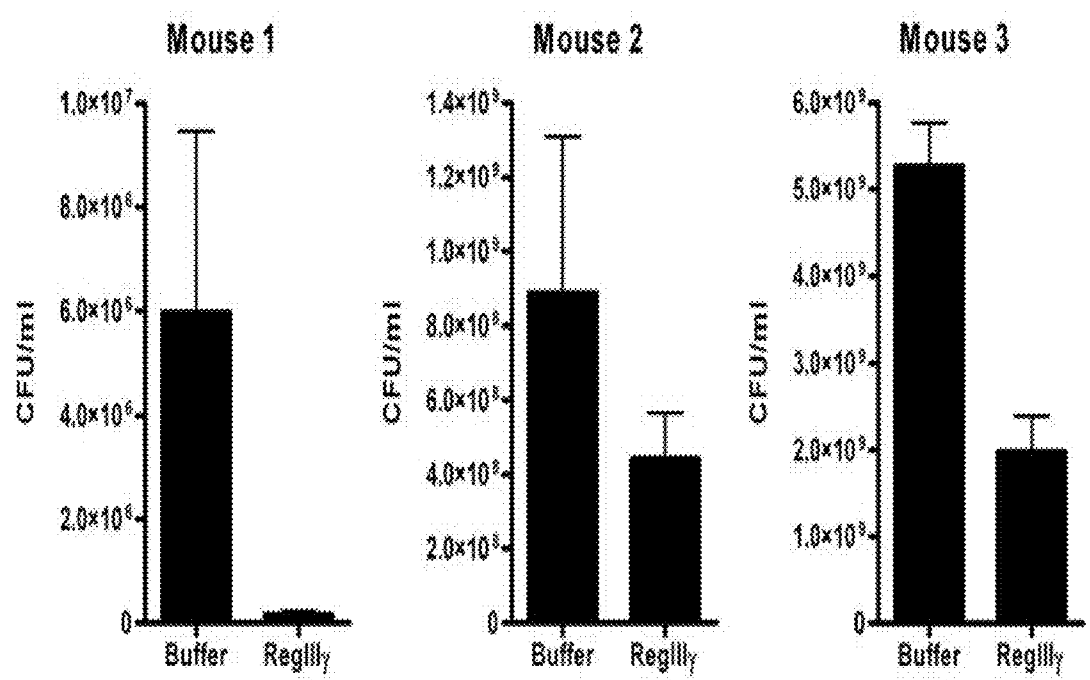
FIG. 14 shows RegIIIγ is bactericidal under native intestinal conditions. The inventors chose *Listeria innocua* monocolonized mice as the model system for this experiment since this organism does not trigger endogenous RegIIIγ expression in wild-type mice (FIG. 15C). Recombinant purified RegIIIγ or buffer was infused into isolated adjacent 1 cm intestinal segments from *Listeria innocua* mice. After 30 minutes, luminal contents from each segment were sampled in triplicate and *Listeria innocua* numbers were quantitated by dilution plating.

The results reveal a carbohydrate ligand preference similar to that of mannose binding lectin (MBL), a C-type lectin with an established role in innate immunity. As a serum protein, MBL recognizes invading microbes by binding to surface mannose residues (Ezekowitz, 2003) or to peptidoglycan (Nadesalingam et al., 2005). This binding triggers the lectin-activated complement pathway, which is initiated by recruitment of the serine proteases MASP1 and 2 via interactions with the MBL collagenous domain. In contrast to MBL, RegIIIγ and HIP/PAP consist of secreted CRDs that lack collagenous domains required for complement recruitment. The inventors therefore postulated that RegIIIγ and HIP/PAP might be directly antimicrobial, without requiring additional factors to kill targeted microbes. The inventors tested this idea by adding purified RegIIIγ and HIP/PAP to Gram-positive enteric microbes including *Listeria monocytogenes, Listeria innocua*, and *Enterococcus faecalis*, and observed a dose-dependent reduction in the viability of each organism (FIG. 13A). The number of colony forming units (CFU) of each microbe declined by 99% after a 2 hour exposure to 5 μM HIP/PAP (FIG. 13A). A similar decline in the viability of *L. monocytogenes* and *L. innocua* was observed after a 2 hour exposure to 5 μM RegIIIγ (FIG. 13A). The viability of *E. faecalis* declined by ~80% after a 2 hour exposure to 10 μM RegIIIγ (FIG. 13A). Thus, the effective antibacterial concentrations of both lectins are similar to those of other intestinal antimicrobial proteins (Harder et al., 2001; Porter et al., 1997). Furthermore, the inventors found that infusion of RegIIIγ into isolated small intestinal segments from *Listeria innocua* monocolonized mice resulted in a decline in bacterial numbers relative to a buffer infusion (FIG. 14), indicating that RegIIIγ is active under native intestinal conditions.

As expected, neither RegIIIγ nor HIP/PAP was bactericidal toward the Gram-negative enteric organisms *Escherichia coli* or *Bacteroides thetaiotaomicron* (FIG. 13A). This is consistent with the observation of preferential binding to Gram-positive bacteria and the fact that peptidoglycan is buried in the periplasmic space of Gram-negative bacteria. Additionally, neither lectin reduced the viability of fungal microorganisms, including *Saccharomyces cerevisiae* and *Candida albicans*.

The inventors used transmission electron microscopy to visualize morphological changes in *Listeria monocytogenes* cells following exposure to RegIIIγ and HIP/PAP. The images revealed evidence of cell wall damage and cytoplasmic leakage (FIG. 13B). These results are remarkably similar to those obtained with cationic antimicrobial peptides such as human β-defensin-3 (Harder et al., 2001), which kill bacteria by cell wall permeabilization. These findings indicate that lectin-mediated bacterial killing also involves cell wall damage.

RegIIIγ and HIP/PAP bactericidal activities were inhibited with soluble peptidoglycan and chitin fragments, linking peptidoglycan binding to antibacterial function. Addition of 35 μM soluble peptidoglycan (sPGN) to antibacterial assays inhibited the bactericidal activity of both lectins (FIG. 13C). 10 mM chitotetraose, a 4-sugar acid hydrolysis fragment of chitin, also fully inhibited the antibacterial activity of both RegIIIγ and HIP/PAP (FIG. 13C). Consistent with the preference of RegIIIγ and HIP/PAP for polymeric sugars, 10 mM monomeric GlcNAc or chitobiose ($GlcNAc_2$) were less inhibitory. These results demonstrate that a soluble oligosaccharide that mimics the peptidoglycan saccharide backbone is sufficient to inhibit lectin antimicrobial activity. These findings are consistent with a model in which lectin binding to surface peptidoglycan carbohydrate precedes microbial killing.

EXAMPLE 8

RegIII Expression

Given RegIIIγ's bactericidal activity, the inventors predicted that its expression patterns would reflect microbial colonization levels in the mouse small intestine. Q-PCR analysis of RegIIIγ mRNA levels along the cephalocaudal axis of conventionalized small intestines revealed increasing expression toward the distal region (ileum; FIG. 15A), concomitant with increasing microbial densities. In contrast, germ-free mice showed minimal RegIIIγ expression throughout the small intestine (FIG. 15A). The inventors also assayed for changes in RegIIIγ mRNA expression during postnatal intestinal development. RegIIIγ mRNA levels rose dramatically during the weaning period (postnatal days 17-22) and remained high into adulthood (>P28) in conventionally-raised but not germ-free mice (FIG. 15B). Weaning is associated with dramatic changes in gut microflora composition as well as withdrawal of maternal IgA antibodies. The antibacterial activity of RegIIIγ suggests that its expression is elicited as part of a compensatory response to maintain mucosal homeostasis in the face of changing microbial ecology and withdrawal of passive immunity.

Because conventional microflora are composed of diverse microbial societies, the inventors asked whether single enteric bacterial species are sufficient to drive small intestinal RegIIIγ expression. As expected, a mixed microbial community recovered from a conventional mouse elicited a ~20-fold increase in RegIIIγ expression when introduced into germ-free wild-type C57/b6 mice. In contrast, colonization with the Gram-negative symbiont *Bacteroides thetaiotaomicron* elicited only a 2.5-fold increase in expression, while the non-invasive Gram-positive *Listeria innocua* had no effect on RegIIIγ mRNA levels (FIG. 15C). These results indicate that neither organism alone was sufficient to stimulate RegIIIγ expression to conventional levels in wild-type mice. However, bacteria that are normally strictly compartmentalized in the intestinal lumen show increased mucosal adherence and invasion in mice that lack mucosal IgA (Macpherson et al., 2000). The inventors therefore postulated that mucosal defenses such as secretory IgA might be sufficient to sequester *B. thetaiotaomicron* and *L. innocua* in the gut lumen, accounting for the inability of these single species to stimulate RegIIIγ expression. Indeed, the inventors found that *B. thetaiotaomicron* and *L. innocua* trigger a 52- and 41-fold increase, respectively, in RegIIIγ mRNA expression following colonization of germ-free RAG1-deficient mice, which lack mature lymphocytes and are therefore IgA-deficient (Mombaerts et al., 1992). Wild-type and RAG1-deficient mice were colonized to virtually identical levels (~$10^8$ cfu/ml ileal contents), indicating that differences in RegIIIγ mRNA expression did not result from differences in total microbial numbers. These findings thus support a model in which increased bacterial-epithelial contact drives RegIIIγ expression as a mechanism to limit potential microbial penetration and maintain mucosal surface integrity.

EXAMPLE 9

N-Terminal Cleavage

Purified recombinant HIP/PAP was cleaved by the addition of bovine trypsin (Sigma) in a 1:200 molar ratio (trypsin:HIP/PAP). After 2 hours incubation at 37° C., 5 μM trypsin-treated HIP/PAP or uncleaved recombinant HIP/PAP was added to *Listeria monocytogenes* that had been grown to mid-log phase in brain-heart infusion (BHI) broth and resuspended in 25 mM MES pH 6, 25 mM NaCl. Initial bacterial concentrations ranged from $10^5$ to $10^6$ CFU/ml. After incubation for 2 hours at 37° C., viable bacteria were quantitated by dilution plating on BHI agar plates.

FIG. 17 shows that without truncation there is little or no bactericidal activity and with truncation, there is bactericidal activity. Thus, it was determined that cleavage of 11 amino acids from the N-terminus of HIP/PAP resulted in increased bactericidal activity as shown in FIG. 17.

EXAMPLE 10

Microbial Danger Sensing in the Gut

A. Methods

Conventionally-raised mice. Conventionally-raised wild-type C57/b6 mice, MyD88$_{-/-}$ mice were maintained in the barrier facility at the University of Texas Southwestern Medical Center at Dallas. NOD2-deficient mice were obtained from Jackson Laboratories and were bred in the barrier facility at UT Southwestern. TRIF-deficient mice were provided by Dr. Eric Pamer at Memorial Sloan Kettering. RICK-deficient mice were from Dr. Gabriel Nunez at the University of Michigan. TLR2-, TLR4-, TLR5-, TLR9-, TLR2/4-, and Tirap-deficient mice were from Dr. Felix Yarovinsky and Dr. Alan Sher at the National Institutes of Health. Mice harboring an epithelial cell-specific IKKβ deletion (IKKb$_{\Delta IEC}$) and littermate controls harboring a floxed IKKβ allele (IKKb$_{F/F}$) were from Dr. Lars Eckmann and Dr. Michael Karin at the University of California at San Diego.

Gnotobiotic mice. Germ-free C57/b6 mice were maintained in plastic gnotobiotic isolators as previously described. For monocolonization experiments, age-matched germ-free C57/b6 mice were orally gavaged with $10^8$ cfu of stationary phase bacterial culture. Mice were killed after the indicated times and intestinal tissues were snap frozen for RNA extraction. Small intestinal colonization levels were measured by dilution plating of luminal contents. Bacterial levels in spleen were determined by dilution plating of homogenized tissue.

Bacterial strains. The following bacterial strains were used to colonize germ-free mice: *Bacteroides thetaiotaomicron* strain VPI-5482, *Salmonella typhimurium* strain SL1433, ΔSPI-1 (a *S. typhimurium* mutant isogenic to the SL1433 background).

Quantitative PCR (Q-PCR). Total RNA was isolated from small intestinal tissues using the Qiagen RNeasy RNA isolation kit and was used to synthesize cDNA. SYBR green-based Q-PCR used gene-specific primers (Table 4) and Stratagene Brilliant Q-PCR master mix. Signals were normalized to 18S rRNA levels within each sample, and normalized data were used to quantitate relative levels of gene expression using ΔΔCt analysis.

TABLE 4

| Target Gene | Forward Primer | Reverse Primer |
|---|---|---|
| RegIIIγ | 5'-TTCCTGTCCTCCATGATCAAAA (SEQ ID NO: 51) | 5'-CATCCACCTCTGTTGGGTTCA (SEQ ID NO: 52) |
| Defer-rs-10 | 5'-ATCATCCAGGTGATTCCCAGCCAT (SEQ ID NO: 55) | 5'-TTCCGGGTCTCCAAAGGAAACAGA (SEQ ID NO: 56) |
| 18S rRNA | 5'-CATTCGAACGTCTGCCCTATC (SEQ ID NO: 53) | 5'-CCTGCTGCCTTCCTTGGA (SEQ ID NO: 54) |

Immunohistochemistry. Bouins-fixed, paraffin-embedded tissue sections were stained with anti-RegIIIγ antiserum 30 or preimmune serum, and detected using a Goat anti-Rabbit IgG Cy3 conjugate (Biomeda). Tissues were counterstained with Hoescht dye.

Bone marrow reconstitution. Recipient mice (wt or MyD88-deficient) were γ-irradiated twice with 5 Gy and were reconstituted with 5×$10^6$ bone-marrow cells from Ly5.1 wt donor mice (6-8 weeks of age). At 6 weeks after reconstitution, mice were tested for chimerism and analyzed for RegIIIγ expression.

B. Results

The inventors first delineated the host factors that govern RegIIIγ expression in response to bacterial cues. A major class of host receptors that recognize conserved molecular patterns on bacteria are the membrane bound Toll-like receptors (TLRs). RegIIIγ expression was diminished in the small intestines of conventionally-raised mice that lack MyD88, an adaptor molecule essential for signaling downstream of multiple TLRs. RegIIIγ mRNA levels were reduced 36-fold in MyD88$_{-/-}$ mice compared to wild-type conventionally-raised mice and were similar to levels detected in germ-free mice (FIGS. 18A-B). The inventors furthermore detected these differences in RegIIIγ mRNA levels in laser capture microdissected Paneth cells (FIG. 18C), a specialized small intestinal epithelial lineage that plays a key role in antimicrobial defense. In contrast, RegIIIγ was expressed at or above wild-type levels in mice lacking TRIF (FIG. 18A), an adaptor molecule required for MyD88-independent TLR signaling13, suggesting that MyD88-independent TLR signaling pathways do not govern RegIIIγ expression. Similarly, RegIIIγ was expressed at wild-type levels in mice lacking the kinase RICK (RIP2) (FIG. 18A), which transduces signals from members of the Nod family of intracellular pattern recognition receptors.

MyD88 is involved in both TLR and IL-1 receptor signaling12. To determine whether TLRs direct RegIIIγ expression in gut epithelia, the inventors analyzed conventionally raised mice lacking specific TLRs that are involved in the recognition of bacterial products. RegIIIγ expression was at or above wild-type levels in TLR5- and TLR9-deficient mice, but was reduced in mice lacking either TLR2 or TLR4 (FIG. 18D). Consistent with these findings, RegIIIγ expression was lower in TLR2/4 doubly deficient mice, as well as in mice lacking TIRAP (FIG. 18D), an adaptor molecule specifically involved in MyD88-dependent signaling through TLR2 and TLR4.

The inventors next sought to determine the cellular origin of the MyD88-dependent signals that govern RegIIIγ expression. Previous studies have shown that microbe-TLR interactions are crucial for driving epithelial regeneration following mucosal injury. In this case, microbial products are detected by TLRs on bone marrow-derived lineages, which then transmit regenerative signals to epithelial progenitor cells. The inventors therefore assessed whether bone marrow-derived cells are also required for microbial induction of RegIIIγ expression by examining chimeric animals. Adoptive transfer of wild-type bone marrow into lethally irradiated MyD88-deficient mice did not restore RegIIIγ expression, as would be expected if commensal microflora signals were detected by a hematopoietic cell lineage (FIG. 19A). Instead, RegIIIγ expression in the chimeric mice was similar to that observed in MyD88-deficient mice, indicating that non-hematopoietic cells recognize the bacterial ligands that induce RegIIIIγ expression.

These findings suggested the possibility that RegIIIγ expression is governed by epithelial cell-intrinsic innate immune signals. MyD88 signals are transduced through the IKK complex (IKKα, β, and γ), resulting in activation of NFκB expression12. To determine whether epithelial cell-specific signals drive RegIIIγ expression the inventors analyzed mice that harbor an intestinal epithelial cell-specific deletion of IKKβ. The inventors found that RegIIIγ expression in these mice is reduced ~20-fold relative to littermates that harbor a floxed IKKβ allele, indicating that epithelial cell-intrinsic innate signaling drives RegIIIγ expression. These findings thus support a model in which commensal bacteria elicit epithelial antimicrobial responses through epithelial cell-intrinsic MyD88-dependent Toll-like receptor (TLR) signaling.

To gain insight into how bacteria are "perceived" by TLRs on epithelial cells, the inventors sought to define the bacterial characteristics that are required to trigger RegIIIγ expression. Germ-free mice provide a powerful tool for these analyses as the inventors can define in vivo host responses to single bacterial species without interference from the diverse microbial societies normally present in the intestine. *Bacteroides thetaiotaomicron* is a prototypical non-invasive gram-negative commensal species that is a numerically prominent inhabitant of the human intestine-18. Colonization of wild-type germ-free mice with *B. thetaiotaomicron* elicited an 8-fold increase in RegIIIγ expression (FIG. 20A). However, when introduced into germ-free immunodeficient ($RAG1_{-/-}$) hosts, *B. thetaiotaomicron* triggered a ~100-fold increase in RegIIIγ expression relative to germ-free levels, similar to the inventors' previous results8. Wild-type and RAG1-deficient mice were colonized to virtually identical levels (~$10^8$ CFU/ml ileal contents; FIG. 20B), indicating that differences in RegIIIγ mRNA expression between hosts did not arise from differences in total microbial numbers. Instead, as RAG1-deficient mice lack adaptive immune system components that limit bacterial penetration of gut epithelia, the inventors postulated that bacterial adherence and/or invasion is a key trigger for RegIIIγ expression.

The inventors chose *Salmonella typhimurium* as a model to test this idea as it invades through intestinal epithelia and its invasive mechanisms have been genetically characterized. Despite its invasive potential, *S. typhimurium* can be used to colonize germ-free mice with little morbidity or mortality before ~8 days post-inoculation. A time course established that colonization of germ-free mice with wild-type *S. typhimurium* induced RegIIIγ expression by 9 hours and that expression was sustained for up to 48 hours (FIG. 22). The inventors therefore compared RegIIIγ expression in mice colonized for 48 hours with wild-type *Salmonella typhimurium* or the isogenic mutant strain ΔSPI-1, which lacks pathogenicity island SPI-1. As SPI-1 harbors genes that are required for *S. typhimurium* invasion of epithelial cells, the mutant is invasion defective24. Luminal colonization levels for the wild-type and mutant strains were virtually identical (~$10_7$; FIG. 20C). However, higher numbers of wild-type *Salmonella* were detected in spleen as compared to the ΔSPI-1 mutant (FIG. 20C). Consistent with the differences in bacterial translocation to spleen, RegIIIγ expression levels elicted by wild-type *Salmonella* were 17-fold higher than those elicited by the ΔSPI-1 mutant (FIGS. 20D-E). These results support the idea that RegIIIγ expression is triggered by adherent or invasive bacterial stimuli.

Taken together, these findings demonstrate that that RegIIIγ expression can be activated by either a host immunologic defect that leads to increased gut epithelial penetration by non-invasive commensal bacteria, or by pathogenic bacteria that harbor intrinsic mechanisms for gut epithelial invasion. This suggests that differences in the way that commensals and pathogens are perceived by the innate immune system are based not on intrinsic differences in their molecular patterns, but on their proximity to the mucosal surface. Further studies will be required to determine whether the actual trigger of the TLR/RegIIIγ system is bacterial adherence to epithelia, or whether invasion of the mucosal barrier is required to activate this detection/response system.

NOD proteins are cytosolic microbial sensors that detect bacterial peptidoglycan motifs (Girardin et al., 2003; Inohara et al., 2003). The intracellular localization of NODs points to the idea that they are poised to detect bacterial invasion of host cells in vivo. Furthermore, the fact that NOD2 is found in small intestinal Paneth cells has led to the proposal that it plays a key role in detecting bacterial invasion of the intestinal mucosa. To assess the role of NOD2 in the in vivo response to invasive bacterial stimuli, the inventors tested for activation of NOD2-driven antimicrobial responses in the inventors' gnotobiotic models. Previous studies have revealed NOD2-dependent expression of key members of the Paneth cell α-defensin family in mice, including Defer-rs-10.

Comparison Defer-rs-10 expression levels in germ-free and conventionally-raised mice revealed that it is activated by microbial signals (FIG. 21A), consistent with their regulation through NOD2. However, in contrast to RegIIIγ, Defer-rs-10 expression was induced by *B. thetaiotaomicron* in wild-type mice, with no significant difference in expression between wild-type and immunodeficient mice (FIG. 21B). Consistent with this finding, Defer-rs-10 expression was modestly induced in mice that were colonized with either wild-type *S. typhimurium* or with the invasion-defective ΔSPI-1 mutant (FIG. 21C). Thus, colonization of the gastrointestinal tract triggers NOD2-driven antimicrobial responses. In contrast to TLR-driven RegIIIγ expression, there is no significant difference in the response to invasive and non-invasive bacterial stimuli, suggesting that activation of defensin expression by NOD2 may represent a generic response to bacterial colonization of the gut.

The inventors have thus found that gut epithelia harbor an epithelial cell-intrinsic mechanism for sensing intestinal bacteria that is activated in response to microbial threats. As this sensing mechanism activates production of an antimicrobial protein, RegIIIγ, it likely functions to restore homeostatic interactions between intestinal microbes and the mucosal surface. These results suggest that although TLRs detect extracellular bacterial products, they play an essential role in detecting the presence of adherent or invasive intestinal bacteria. In contrast, antimicrobial responses governed by the cytoplasmic receptor NOD2 are elicited by intestinal bacteria independently of invasive potential. Given the ubiquitous presence of bacterial ligands in the gut, the inventors envision at least two mechanisms by which epithelial surface TLRs could fulfill a microbial danger-sensing function. First, positioning of TLRs on the basolateral side of epithelial tight junctions would require microbial invasion of epithelia in order to activate TLR signaling pathways. A second possibility is that the receptors are positioned on the apical surface of gut epithelia but signal only when their bacterial ligands exceed a certain concentration threshold, which could allow detection of adherent (but not necessarily invasive) bacteria.

The results presented here suggest that antimicrobial defenses in the gastrointestinal tract operate as a "multi-tiered" system. The inventors propose that antimicrobial responses governed by NOD2 act as a primary shield that maintains homeostasis by compartmentalizing microbes in the gut lumen. In this model, TLR-driven RegIIIγ production represents a secondary antimicrobial response that is activated only when the NOD2-driven primary response fails to maintain microbial compartmentalization, either because of microbe-intrinsic mucosal invasion mechanisms or because of host immunodeficiency. This idea is consistent with observations in inflammatory bowel disease patients. NOD2 mutations are associated with familial Crohn's disease and have been linked to reduced expression of α-defensins. At the same time, members of the Reg lectin family show increased expression in IBD mucosa. These findings point to a model of disease in which immunodeficiencies, such as NOD2 mutations, lead to primary barrier defects that result in increased bacterial invasion of intestinal mucosa with consequent activation of Reg expression. The identification of Reg expression as an indicator of microbial danger suggests its use as an early indicator of the need for therapeutic intervention prior to the onset of inflammation in patients predisposed to inflammatory bowel disease.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,642,104
U.S. Pat. No. 5,110,795
U.S. Pat. No. 5,112,856
U.S. Pat. No. 5,216,002
U.S. Pat. No. 5,220,007
U.S. Pat. No. 5,238,931
U.S. Pat. No. 5,284,760
U.S. Pat. No. 5,292,771
U.S. Pat. No. 5,312,818
U.S. Pat. No. 5,324,738
U.S. Pat. No. 5,331,013
U.S. Pat. No. 5,340,801
U.S. Pat. No. 5,354,670
U.S. Pat. No. 5,366,878
U.S. Pat. No. 5,368,854
U.S. Pat. No. 5,389,514
U.S. Pat. No. 5,391,555
U.S. Pat. No. 5,399,363
U.S. Pat. No. 5,440,013
U.S. Pat. No. 5,446,128
U.S. Pat. No. 5,466,468
U.S. Pat. No. 5,466,468
U.S. Pat. No. 5,475,085
U.S. Pat. No. 5,543,158
U.S. Pat. No. 5,552,439
U.S. Pat. No. 5,569,680
U.S. Pat. No. 5,580,579
U.S. Pat. No. 5,599,795
U.S. Pat. No. 5,604,231
U.S. Pat. No. 5,618,914
U.S. Pat. No. 5,629,001
U.S. Pat. No. 5,635,377
U.S. Pat. No. 5,641,515
U.S. Pat. No. 5,641,515
U.S. Pat. No. 5,670,155
U.S. Pat. No. 5,672,681
U.S. Pat. No. 5,674,976
U.S. Pat. No. 5,691,343
U.S. Pat. No. 5,693,645
U.S. Pat. No. 5,710,245
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 5,840,833
U.S. Pat. No. 5,859,184
U.S. Pat. No. 5,929,237
U.S. Pat. No. 6,297,015
U.S. Pat. No. 6,348,452

U.S. Pat. No. 6,613,308
U.S. Pat. No. 6,753,514
Abergel et al., *D Biol. Crystallogr.,* 55(Pt 8):1487-1489, 1999.
Ayabe et al., *Nat. Immunol.,* 1:113, 2000.
Bertrand et al., *Embo J.,* 15:2678-2684, 1996.
Bohm et al., Protein Eng., 5:191-195, 1992.
Bradford, Anal. Biochem., 72:248-254, 1976.
Capaldi et al., *Biochem. Biophys. Res. Comm.,* 76:425, 1977.
Cash et al., Protein Expr. Purif., 48(1):151-159, 2006.
Cecil Textbook of Medicine, 19th Edition, Wyngaarden et al., ed., 1992.
Christa et al., *Am. J. Physiol.,* 271:G993-1002, 1996.
Christa et al., *Eur. J. Biochem.,* 267:1665-1671, 2000.
Christa et al., *FEBS Lett.* 337:114-118, 1994.
Dieckgraefe et al., *J Investig. Med.,* 50:421-434, 2002.
Drickamer et al., *Annu. Rev. Cell Biol.,* 9:237-264, 1993.
Drickamer et al., *Biochem. Soc. Symp.,* 59-72, 2002.
Drickamer et al., *Glycobiology,* 9:1357, 1999.
Drickamer, *Curr. Opin. Struct. Biol.,* 9:585-590, 1999.
Drickamer, *Nature,* 360:183, 1992.
Dziarski et al., *J. Biol. Chem.,* 273:8680, 1998.
Eckburg et al., *Science,* 308 :1635, 2005.
Ezekowitz, *J. Infect. Dis.,* 187(2):S335-339, 2003.
Girardin et al., *Science* 300, 1584-7, 2003.
Harder et al., *J. Biol. Chem.,* 276:5707, 2001.
Harlow and Lane, In: *Antibodies: A Laboratory Manual,* Cold Spring Harbor Laboratory, 1988.
Holloway et al., *Protein Expr. Purif.,* 22:307-317, 2001.
Holm et al., *Appl. Environ. Microbiol.,* 69:2857, 2003.
Hooper et al., *Annu. Rev. Nutr.,* 22:283, 2002.
Hwang et al., *Crit. Rev. Ther. Drug Carrier Syst.,* 15(3):243-284, 1998.
Inohara et al., *J. Biol. Chem.* 278, 5509-12, 2004.
Johannesson et al., *J. Med. Chem.,* 42:601-608, 1999.
Johnson et al., In: *Biotechnology and Pharmacy,* Pezzuto et al., eds., Chapman and Hall, New York, 1993.
Julenius et al., *Glycobiology,* 15:153-164, 2005.
Keilbaugh et al., *Gut,* 54:623-629, 2005.
Kyte and Doolittle, *J. Mol. Biol.,* 157(1):105-132, 1982.
Liu et al., *J. Biol. Chem.,* 275:24490, 2000.
Livesey et al., *Nature,* 390:614, 1997.
Lobley et al., *Bioinformatics,* 18:211-212, 2002.
Macpherson et al., *Science,* 288:2222, 2000.
Mandel and Higa, *J. Mol. Biol.,* 53(1):159-162, 1970.
Mathiowitz et al., *Nature,* 386(6623):410-414, 1997.
Mombaerts et al., *Cell,* 68:869, 1992.
Nadesalingam et al., *J. Immunol.,* 175:1785, 2005.
Narushima et al., *Gene,* 185:159-168, 1997.
Ogawa et al., *Am. J. Physiol. Gastrointest. Liver Physiol.,* 279:G492-499, 2000.
Ogawa et al., *Inflamm. Bowel Dis.,* 9:162-170, 2003.
Porter et al., *Infect. Immun.,* 65 :2396, 1997.
Pull et al., *Proc. Natl. Acad. Sci. USA,* 102:99, 2005.
Remington's Pharmaceutical Sciences" 15th Edition, pages 1035-1038 and 1570-1580, 1990.
Remington's Pharmaceutical Sciences, 18th Ed. Mack Printing Company, pp. 1289-1329, 1990.
Shigekawa and Dower, *Biotechniques,* 6(8):742-751, 1988.
Sreerama et al., *J. Mol. Biol.,* 242:497-507, 1994.
Stambach et al., *Glycobiology,* 13:401-410, 2003.
Swidsinski et al., *Gastroenterology,* 122:44, 2002.
Syder et al., *Proc. Natl. Acad. Sci. USA,* 100:3467, 2003.
Takenaga et al., *J. Control Release,* 52(1-2):81-87 1998
Taneva et al., *Biochemistry,* 36:8173-8179, 1997.
Taylor et al., *Methods Enzymol.,* 363:3-16, 2003.
Terazono et al., *J. Biol. Chem.,* 263:2111-2114, 1988.
Vita et al., *Biopolymers,* 47:93-100, 1998.
Wehkamp et al., *Gut,* 53:1658, 2004.
Wehkamp et al., *Proc. Natl. Acad. Sci. USA,* 102:18129, 2005.
Weis et al., *Nature,* 360 :127-134, 1992.
Weis et al., *Structure,* 2:1227-1240, 1994.
Weisshoff et al., *Eur. I Biochem.,* 259:776-788, 1999.
Werner et al., *Proc. Natl. Acad. Sci. USA,* 97:13772, 2000.
Wu and Wu, *Biochemistry,* 27: 887-892, 1988.

What is claimed is:

1. A method of treating an inflammatory bowel disease comprising administering to a subject an effective amount of an antimicrobial composition comprising a pharmaceutical carrier admixed with an fragment of SEQ ID NO: 11, wherein said fragment lacks residues 1-37 of SEQ ID NO: 11.

2. The method of claim 1, wherein said fragment consists of SEQ ID NO: 21.

* * * * *